US006329157B1

(12) United States Patent
Maine et al.

(10) Patent No.: US 6,329,157 B1
(45) Date of Patent: Dec. 11, 2001

(54) ANTIGEN COCKTAILS AND USES THEREOF

(75) Inventors: Gregory T. Maine, Gurnee; Jeffrey C. Hunt, Mundelein, both of IL (US); Susan Brojanac, Brookfield, WI (US); Michael Jyh-Tsing Sheu, Gurnee, IL (US); Linda E. Chovan, Kenosha, WI (US); Joan D. Tyner, Beach Park; Lawrence V. Howard, Libertyville, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/086,503

(22) Filed: May 28, 1998

(51) Int. Cl.$^7$ .................................................... G01N 33/53

(52) U.S. Cl. .......................... 435/7.22; 435/7.1; 435/7.92

(58) Field of Search .................................. 435/7.22, 7.1, 435/7.92, 975

(56) References Cited

U.S. PATENT DOCUMENTS

| 4,877,726 | * | 10/1989 | Suzuki et al. ............................ 435/7 |
| 5,578,453 | * | 11/1996 | MacDonald et al. ................ 435/7.22 |
| 6,221,619 | * | 4/2001 | Maine et al. ......................... 435/7.22 |

FOREIGN PATENT DOCUMENTS

| 0 431 541 | 6/1991 | (EP) . |
| 0 472 207 | 2/1992 | (EP) . |
| 0 782 860 | 7/1997 | (EP) . |
| WO 93/08208 | 4/1993 | (WO) . |
| WO 96/02654 | 2/1996 | (WO) . |
| WO 97/27300 | 7/1997 | (WO) . |

OTHER PUBLICATIONS

Johnson et al. J. Med. Microbiol. 37: 404–409, 1992.*
Wee et al. Parasitology 104: 25–31, 1992.*
Potasman et al. J. Clin. Microbiol. 24: 1050–1054, abstract, 1986.*
Hackett et al. J. Clin. Microbiol. 36: 1277–1284 (Apr. 23, 1998).*
Ahn et al. Korean J. Parasitol. 35: 251–258, abstract (Dec. 1997).*
Yamamoto et al. Ann. Trop. Med. Parasitol. 92: 23–30, abstract (Jan. 1998).*
Shin et al. Korean J. Parasitol. 35: 55–62, abstract (Mar. 1997).*
Zhang et al. Exp. Parasitol. 80: 228–233 (abstract) 1995.*
Fisher et al. Mol. Biochem. Parasitol. 91: 251–262, abstract (Mar. 15, 1998).*
Achbarou et al. Parasitology 103.3: 321–329, abstract (Dec. 1991).*
Knapken et al. Antinie Leeuwenhoek J. Microbiol. 52: 5–14, abstract, 1986.*

Ambroise–Thomas et al. Parasitologia 28: 85–93, abstract, 1986.*

Verhofstede et al. J. Clin. Pathol. 42; 1285–1293, abstract, 1990.*

Fortier et al. Eur. J. Clin. Microbiol. Infect. Dis. 10: 38–40, abstract, 1991.*

Lindenschmidt EG. J. Clin. Microbiol. 24: 1045–1049, abstract, 1986.*

Couvreur et al. Parasitology 97.1: 1–10, abstract, 1988.*

Sharma et al. J. Immunol. 131: 977–983, abstract, 1983.*

Fischer: "Toxoplasma gondii DNA encoding a 29kd excretory dense granule protein" XP002122282 Accession No.: Y13863, ID: TG29EDGP Jun. 30, 1997.

Jacobs et al.: "Identification and heterologous expression of a new dense granule protein (GRA7) from Toxoplasma gondii" Molecular and Biochemical Parasitology, vol. 91, Mar. 15, 1998, pp. 237–249, X002127972.

Kohler et al.: "Continuous cultures of fused cells secreting antibody of predefined specificity" Nature, GB Macmillan Journals Ltd. London, vol. 256, pp. 495–497, XP002044294 ISSN: 0028–0836.

Sabin, A.B. and Feldman, H.A. (1948) Science 108: 660–663.

Naot, Y. and Remington, J.S. (1980) J. Infect. Dis. 142, 757–766.

Prince et al. (1990) Mol. Biochem, Parasitol 43, 97–106.

Cesbron–Delauw et al. (1989) Proc. Nat. Acad. Sci. 86, 7537–7541.

Johnson et al. (1991) Gene 99, 127–132.

Prince et al. (1989) Mol. Biochem. Parasitol. 34, 3–13.

Burg et al. (1988) J. Immunol. 141, 3584–3591.

Mevelec et al. (1992) Mol. Biochem. Parasitol 56, 227–238.

Saavendra et al. (1991) J. Immunol. 147, 1975–1982.

* cited by examiner

*Primary Examiner*—S. Devi
(74) *Attorney, Agent, or Firm*—Cheryl L. Becker

(57) ABSTRACT

The present invention relates to combinations or mixtures of antigens which may be used in the detection of IgM and/or IgG antibodies to *Toxoplasma gondii*. Furthermore, the present invention also relates to methods of using these combinations of antigens, antibodies raised against these combinations of antigens or against the novel P29 antigen thereof, as well as kits and vaccines containing the antigens present in the combinations.

17 Claims, 57 Drawing Sheets pGM613

```
          10         20         30         40
 1234567890 1234567890 1234567890 1234567890
 GAATTCGGCA CGAGGCGAAC TGGGGCAAAG CCGCCGCCAC    40
 AsnSerAla  ArgGlyGluL euGlyGlnSe rArgArgHis

CAGTTCGCTA CCGCGGCCAC CGCGTCAGAT GACGAACTGA    80
 GlnPheAlaT hrAlaAlaTh rAlaSerAsp AspGluLeuM

TGAGTCGAAT CCGAAATTCT GACTTTTTCG ATGGTCAAGC   120
 etSerArgIl EArgAsnSer AspPhePheA spGlyGlnAl

ACCCGTTGAC AGTCTCAGAC CGACGAACGC CGGTGTCGAC   160
 aProValAsp SerLeuArgp roThrAsnAl aGlyValAsp TCGAAAGGGA CCGACHAYCA CCTCACCACC AGCATGGATA   200
 SerLysGlyT hrAspAspHi sLeuThrThr SerMetAspL AGGCATCTGT AGAGAGTCAG CTTCCGAGAA GAGAGCCATT   240
 ysAlaSerVa lGluSerGln LeuProArgA rggluProLe GGAGACGGAG CCAGATGAAC AAGAAGAAGT TCATTTCAGG   280
 uGluThrGlu ProAspGluG lnGluGluVa lHisPheArg AAGCGAGGCG TCCGTTCCGA CGCTGAAGTG ACTGACGACA   320
 LysArgGlyV alArgSerAs pAlaGluVal ThrAspAspA ACATCTACGA GGAGCACACT GATCGTAAGG TGGTTCCGAG   360
 snIleTyrGl uGluHisThr AspArgLysV alValProAr GAAGTCGGAG GGCAAGCGAA GCTTCAAAGA CTTGCTGAAG   400
 gLysSerGlu GlyLysArgS erPheLysAs pLeuLeuLys AAGCTCGCGC TGCCGGCTGT TGGTATGGGT GCATCGTATT   440
 LysLeuAlaL euProAlaVa lGlyMetGly AlaSerTyrP TTGCCGCTGA TAGACTTGTG CCGGAACTAA CAGAGGAGCA   480
 heAlaAlaAs pArgLeuVal ProGluLeuT hrGluGluGl ACAGAGAGGC GACGAACCCC TAACCACCGG CCAGAATGTG   520
 nGluArgGly AspGluProL euThrThrGl yGlnAsnVal
```

FIG.1A pGM613

|  10        |  20        |  30        |  40        |      |
|------------|------------|------------|------------|------|
| 1234567890 | 1234567890 | 1234567890 | 1234567890 |      |
| GGCACTGTGT | TAGGCTTCGC | AGCGCTTGCT | GCTGCCGCAG | 560  |
| GlyThrValL | euGlyPheAl | aAlaLeuAla | AlaAlaAlaA |      |
| CGTTCCTTGG | CATGGGTCTC | ACGAGGACGT | ACCGACATTT | 600  |
| laPheLeuGl | yMetGlyLeu | ThrArgThrT | yrArgHisPh |      |
| TTCCCCACGC | AAAAACAGAT | CACGGCAGCC | TGCACTCGAG | 640  |
| eSerProArg | LysAsnArgS | erArgGlnPr | oAlaLeuGlu |      |
| CAAGAGGTGC | CTGAATCAGG | CGAAGATGGG | GAGGATGCCC | 680  |
| GlnGluValP | roGluSerGl | yGluAspGly | GluAspAlaA |      |
| GCCAGTAGGA | TATGGGGGCT | AATAAAAGTG | AGTAGGAGCT | 720  |
| rgGln      |            |            |            |      |
| CGAGGACAGT | GTCCCGAACG | CGCCTGAGAG | GCAGACAGAC | 760  |
| ACAGAAGAGT | GAAGAAAAAC | AACATGGTAT | TACGTGCGGT | 800  |
| GAGTGTTTGC | TGTCACGTGT | TTTTTGCGCC | ACAAAGACAG | 840  |
| CTTGTGTTGT | ATGCATGGGA | TCGACAGTTC | ATGGACGGCG | 880  |
| CTACCCAGAG | AGGCGGCATT | TGCGTACACC | GTGGGTCGTC | 920  |
| ATGAGTACCG | GGACATCGTG | TTCGTGTTTA | TTTGTTCATG | 960  |
| TCGAAGTGCA | CTAAGACACG | AGACGAAAGG | GTGGTTCCGC | 1000 |
| CCCTGGCAGC | ATCACGTAGT | GGTTTCTTTG | TCGAGAACAG | 1040 |

FIG. 1B pGM613

|  10        |  20        |  30        |  40        |      |
|------------|------------|------------|------------|------|
| 1234567890 | 1234567890 | 1234567890 | 1234567890 |      |
| CGGCAGTCCG | AGGCCACTTG | AGACAGGATG | TTTGAGTGTA | 1080 |
| TACAGACAAC | GTGGTCACAG | CATGAGGCAA | AGCTGTCTAA | 1120 |
| GCAGCCATTT | GCGCGAGCGA | AGTCATCCAT | GCCGACTGTG | 1160 |
| TGAGCCTCTT | TCGTCACTTT | GAATGAGACA | GAAACTAAGA | 1200 |
| CTCGCAGCAG | GTCTGAATAT | TGCGAATAAT | CTACTTTTAA | 1240 |
| AACCAAAAAA | AAAAAAAAAA | AACTCGAG   |            | 1268 |

FIG.1C pTXG1-2

```
         10         20         30         40
 1234567890 1234567890 1234567890 1234567890
 AGACCCCGCC ACCGCCCGTG ACGAACCACG AACCGCGGCG    40

AACGGCGAGC TCACCGGGTT TTCAGAGACG CGCGAGATCC    80

CTGATTTCGT TTACCATTGA CGCCCGCCGC CGTCGACGTC   120

TTTGGAACGT GTTTCACGTT TGAGTTGCAC TGTTACTTTC   160

TTCGGATTAC ATTCTTCCAC TAAAAGCTGG TTTTGTCCAG   200

TATCCATTCG TCGCTACCGT TGCGCAGTCA CGTTGAATTT   240

TGCAGCGGCA AAACATCTTG TGTAAAATTC GAGTTTTGTT   280

GATGATTGAA GTACCCTATA TTGGGGCTTG CTAACGTTTT   320

GTATTAAAAG GGATTACTGC GGCGTCTCAT TTCCAAAATG   360

GCCCGACACG CAATTTTTTC CGCGCTTTGT GTTTTAGGCC   400

TGGTGGCGGC GGCTTTGCCC CAGTTCGCTA CCGCGGCCAC   440

CGCGTCAGAT GACGAACTGA TGAGTCGAAT CCGAAAT      477
```

FIG.2

Composite P29 Gene Sequence

```
         10         20         30         40
1234567890 1234567890 1234567890 1234567890
AGACCCCGCC ACCGCCCGTG ACGAACCACG AACCGCGGCG      40

AACGGCGAGC TCACCGGGTT TTCAGAGACG CGCGAGATCC      80

CTGATTTCGT TTACCATTGA CGCCCGCCGC CGTCGACGTC     120

TTTGGAACGT GTTTCACGTT TGAGTTGCAC TGTTACTTTC     160

TTCGGATTAC ATTCTTCCAC TAAAAGCTGG TTTTGTCCAG     200

TATCCATTCG TCGCTACCGT TGCGCAGTCA CGTTGAATTT     240

TGCAGCGGCA AAACATCTTG TGTAAAATTC GAGTTTTGTT     280

GATGATTGAA GTACCCTATA TTGGGGCTTG CTAACGTTTT     320

GTATTAAAAG GGATTACTGC GGCGTCTCAT TTCCAAAATG     360
                                         Met

GCCCGACACG CAATTTTTTC CGCGCTTTGT GTTTTAGGCC     400
AlaArgHisA laIlePheSe rAlaLeuCys ValLeuGlyL

TGGTGGCGGC GGCTTTGCCC CAGTTCGCTA CCGCGGCCAC     440
euValAlaAl aAlaLeuPro GlnPheAlaT hrAlaAlaTh

CGCGTCAGAT GACGAACTGA TGAGTCGAAT CCGAAATTCT     480
rAlaSerAsp AspGluLeuM etSerArgIl eArgAsnSer

GACTTTTTCG ATGGTCAAGC ACCCGTTGAC AGTCTCAGAC     520
AspPhePheA spGlyGlnAl aProValAsp SerLeuArgP
```

FIG.3A

Composite P29 Gene Sequence

```
         10         20         30         40
1234567890 1234567890 1234567890 1234567890
CGACGAACGC CGGTGTCGAC TCGAAAGGGA CCGACGATCA    560
roThrAsnAl aGlyValAsp SerLysGlyT hrAspAspHi

CCTCACCACC AGCATGGATA AGGCATCTGT AGAGAGTCAG    600
sLeuThrThr SerMetAspL ysAlaSerVa lGluSerGln

CTTCCGAGAA GAGAGCCATT GGAGACGGAG CCAGATGAAC    640
LeuProArgA rgGluProLe uGluThrGlu ProAspGluG

AAGAAGAAGT TCATTTCAGG AAGCGAGGCG TCCGTTCCGA    680
lnGluGluVa lHisPheArg LysArgGlyV alArgSerAs

CGCTGAAGTG ACTGACGACA ACATCTACGA GGAGCACACT    720
pAlaGluVal ThrAspAspA snIleTyrGl uGluHisThr

GATCGTAAGG TGGTTCCGAG GAAGTCGGAG GGCAAGCGAA    760
AspArgLysV alValProAr gLysSerGlu GlyLysArgS

GCTTCAAAGA CTTGCTGAAG AAGCTCGCGC TGCCGGCTGT    800
erPheLysAs pLeuLeuLys LysLeuAlaL euProAlaVa

TGGTATGGGT GCATCGTATT TTGCCGCTGA TAGACTTGTG    840
lGlyMetGly AlaSerTyrP heAlaAlaAs pArgLeuVal

CCGGAACTAA CAGAGGAGCA ACAGAGAGGC GACGAACCCC    880
ProGluLeuT hrGluGluGl nGlnArgGly AspGluProL

TAACCACCGG CCAGAATGTG GGCACTGTGT TAGGCTTCGC    920
euThrThrGl yGlnAsnVal GlyThrValL euGlyPheAl

AGCGCTTGCT GCTGCCGCAG CGTTCCTTGG CATGGGTCTC    960
aAlaLeuAla AlaAlaAlaA laPheLeuGl yMetGlyLeu

ACGAGGACGT ACCGACATTT TTCCCCACGC AAAAACAGAT   1000
ThrArgThrT yrArgHisPh eSerProArg LysAsnArgS

CACGGCAGCC TGCACTCGAG CAAGAGGTGC CTGAATCAGG   1040
erArgGlnPr oAlaLeuGlu GlnGluValP roGluSerGl
```

FIG.3B

Composite p29 Gene Sequence

```
          10          20          30          40
  1234567890  1234567890  1234567890  1234567890
  CGAAGATGGG  GAGGATGCCC  GCCAGTAGGA  TATGGGGGCT    1080
  yGluAspGly  GluAspAlaA  rgGln

AATAAAAGTG  AGTAGGAGCT  CGAGGACAGT  GTCCCGAACG    1120

CGCCTGAGAG  GCAGACAGAC  ACAGAAGAGT  GAAGAAAAAC    1160

AACATGGTAT  TACGTGCGGT  GAGTGTTTGC  TGTCACGTGT    1200

TTTTTGCGCC  ACAAAGACAG  CTTGTGTTGT  ATGCATGGGA    1240

TCGACAGTTC  ATGGACGGCG  CTACCCAGAG  AGGCGGCATT    1280

TGCGTACACC  GTGGGTCGTC  ATGAGTACCG  GGACATCGTG    1320

TTCGTGTTTA  TTTGTTCATG  TCGAAGTGCA  CTAAGACACG    1360

AGACGAAAGG  GTGGTTCCGC  CCCTGGCAGC  ATCACGTAGT    1400

GGTTTCTTTG  TCGAGAACAG  CGGCAGTCCG  AGGCCACTTG    1440

AGACAGGATG  TTTGAGTGTA  TACAGACAAC  GTGGTCACAG    1480

CATGAGGCAA  AGCTGTCTAA  GCAGCCATTT  GCGCGAGCGA    1520

AGTCATCCAT  GCCGACTGTG  TGAGCCTCTT  TCGTCACTTT    1560
```

FIG.3C

Composite P29 Gene Sequence

```
         10         20         30         40
 1234567890 1234567890 1234567890 1234567890
 GAATGAGACA GAAACTAAGA CTCGCAGCAG GTCTGAATAT    1600

TGCGAATAAT CTACTTTTAA AACCAAAAAA AAAAAAAAAA    1640

AACTCGAG                                      1648
```

FIG.3D

Old Polylinker Sequence

```
          10          20          30          40
 1234567890  1234567890  1234567890  1234567890
```

```
                                          SmaI
  BglII       SalI   EcoRI      SacI    KpnI
    ▼           ▼      ▼          ▼      ▼▼
AGATCTCGAC CCGTCGACGA AATCGAGCTC GGTACCCGGG    40
AspLeuAsp  ProSerThrA snSerSerSe rValProGly
```

```
BamHI XbaI      PstI    SphI            BglII
  ▼    ▼         ▼        ▼               ▼
GATCCTCTAG ACTGCAGGCA TGCTAAGTAA GTAGATCT     78
AspProLeuA spCysArgHi sAlaLys
```

FIG.4B

New Sequence

```
          10          20          30          40
 1234567890  1234567890  1234567890  1234567890
```

BstYI
BglII                   BbsI
▼                       ▼
AGATCTCGAC  CCATCTACCA  ATTCGTCTTC  TGTTCCGGGT    40
AspLeuAsp   ProSerThrA  snSerSerSe  rValProGly

BstyI
                                    BglII
                                    ▼
GATCCGCTAG  ACTGCCGTCA  CGCTAAGTAA  GTAGATCT      78
AspProLeuA  spCysArgHi  sAlaLys

FIG. 4C

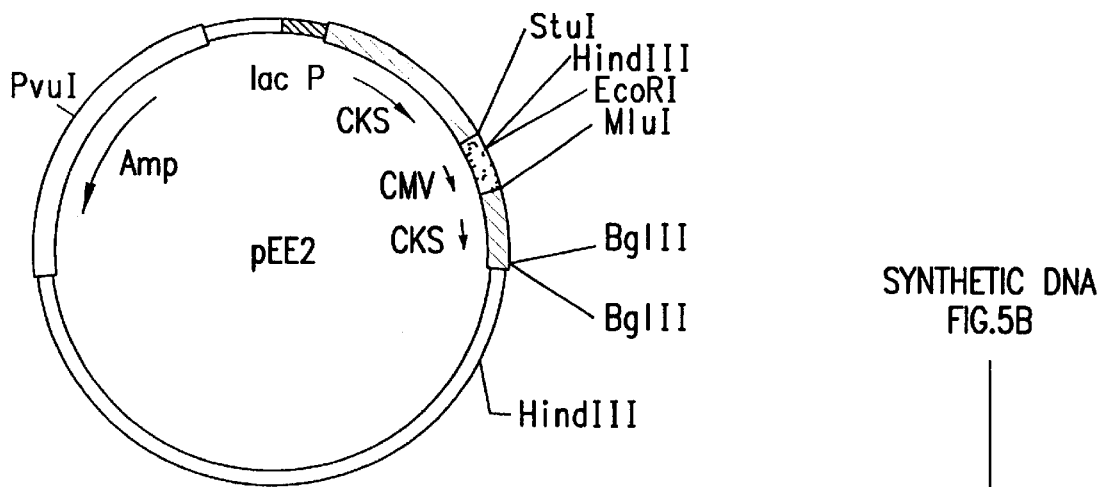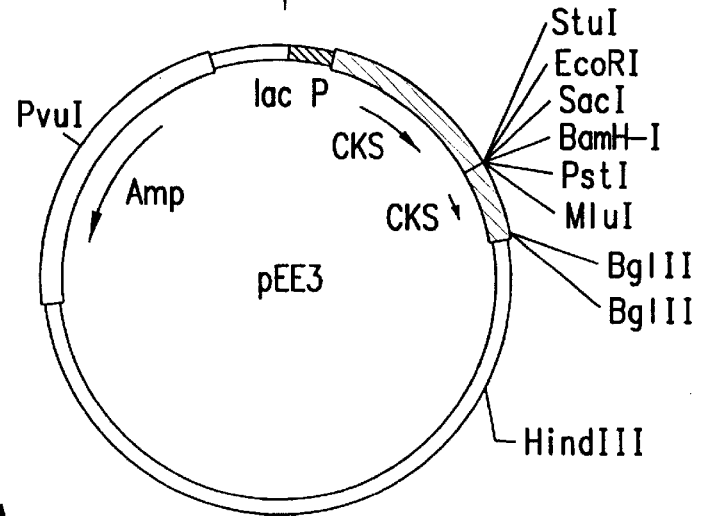
FIG.5A pEE3 Polylinker Sequence

```
          10          20          30          40
 1234567890  1234567890  1234567890  1234567890

EcoRI                           MluI
   StuI              SacI BamHI        PstI
    ▼  ▼              ▼    ▼            ▼  ▼
 AGGCCTGAAT  TCGAGCTCTG  GGATCCGTCT  GCAGACGCGT      40
 GlyLeuAsn   SerSerSerG  lyIleArgLe  uGlnThrArg
```

FIG. 5B pToxo-P29

```
          10         20         30         40
 1234567890 1234567890 1234567890 1234567890
 GAATTAATTC CCATTAATGT GAGTTAGCTC ACTCATTAGG      40

CACCCCAGGC TTTACACTTT ATGTTCCGGC TCGTATTTTG      80

TGTGGAATTG TGAGCGGATA ACAATTGGGC ATCCAGTAAG     120

GAGGTTTAAA TGAGTTTTGT GGTCATTATT CCCGCGCGCT     160
          M etSerPheVa lValIleIle ProAlaArgT

ACGCGACGTC GCGTCTGCCC GGTAAACCAT TGGTTGATAT     200
 yrAlaThrSe rArgLeuPro GlyLysProL euValAspIl

TAACGGCAAA CCCATGATTG TTCATGTTCT TGAACGCGCG     240
 eAsnGlyLys ProMetIleV alHisValLe uGluArgAla

CGTGAATCAG GTGCCGAGCG CATCATCGTG GCAACCGATC     280
 ArgGluSerG lyAlaGluAr gIleIleVal AlaThrAspH

ATGAGGATGT TGCCCGCGCC GTTGAAGCCG CTGGCGGTGA     320
 isGluAspVa lAlaArgAla ValGluAlaA laGlyGlyGl

AGTATGTATG ACGCGCGCCG ATCATCAGTC AGGAACAGAA     360
 uValCysMet ThrArgAlaA spHisGlnSe rGlyThrGlu

CGTCTGGCGG AAGTTGTCGA AAAATGCGCA TTCAGCGACG     400
 ArgLeuAlaG luValValGl uLysCysAla PheSerAspA

ACACGGTGAT CGTTAATGTG CAGGGTGATG AACCGATGAT     440
 spThrValIl eValAsnVal GlnGlyAspG luProMetIl

CCCTGCGACA ATCATTCGTC AGGTTGCTGA TAACCTCGCT     480
 eProAlaThr IleIleArgG lnValAlaAs pAsnLeuAla

CAGCGTCAGG TGGGTATGAC GACTCTGGCG GTGCCAATCC     520
 GlnArgGlnV alGlyMetTh rThrLeuAla ValProIleH
```

FIG.7A pToxo-P29

|  | 10 | 20 | 30 | 40 |  |
|---|---|---|---|---|---|
|  | 1234567890 | 1234567890 | 1234567890 | 1234567890 |  |
|  | ACAATGCGGA | AGAAGCGTTT | AACCCGAATG | CGGTGAAAGT | 560 |
|  | isAsnAlaGl | uGluAlaPhe | AsnProAsnA | laValLysVa |  |
|  | GGTTCTCGAC | GCTGAAGGGT | ATGCACTGTA | CTTCTCTCGC | 600 |
|  | lValLeuAsp | AlaGluGlyT | yrAlaLeuTy | rPheSerArg |  |
|  | GCCACCATTC | CTTGGGATCG | TGATCGTTTT | GCAGAAGGCC | 640 |
|  | AlaThrIleP | roTrpAspAr | gAspArgPhe | AlaGluGlyL |  |
|  | TGAATTCGAT | GGCCCGACAC | GCAATTTTTT | CCGCGCTTTG | 680 |
|  | euAsnSerMe | tAlaArgHis | AlaIlePheS | erAlaLeuCy |  |
|  | TGTTTTAGGC | CTGGTGGCGG | CGGCTTTGCC | CCAGTTCGCT | 720 |
|  | sValLeuGly | LeuValAlaA | laAlaLeuPr | oGlnPheAla |  |
|  | ACCGCGGCCA | CCGCGTCAGA | TGACGAACTG | ATGAGTCGAA | 760 |
|  | ThrAlaAlaT | hrAlaSerAs | pAspGluLeu | MetSerArgI |  |
|  | TCCGAAATTC | TGACTTTTTC | GATGGTCAAG | CACCCGTTGA | 800 |
|  | leArgAsnSe | rAspPhePhe | AspGlyGlnA | laProValAs |  |
|  | CAGTCTCAGA | CCGACGAACG | CCGGTGTCGA | CTCGAAAGGG | 840 |
|  | pSerLeuArg | ProThrAsnA | laGlyValAs | pSerLysGly |  |
|  | ACCGACGATC | ACCTCACCAC | CAGCATGGAT | AAGGCATCTG | 880 |
|  | ThrAspAspH | isLeuThrTh | rSerMetAsp | LysAlaSerV |  |
|  | TAGAGAGTCA | GCTTCCGAGA | AGAGAGCCAT | GGAGACGGA | 920 |
|  | alGluSerGl | nLeuProArg | ArgGluProL | euGluThrGl |  |
|  | GCCAGATGAA | CAAGAAGAAG | TTCATTTCAG | GAAGCGAGGC | 960 |
|  | uProAspGlu | GlnGluGluV | alHisPheAr | gLysArgGly |  |
|  | GTCCGTTCCG | ACGCTGAAGT | GACTGACGAC | AACATCTACG | 1000 |
|  | ValArgSerA | spAlaGluVa | lThrAspAsp | AsnIleTyrG |  |
|  | AGGAGCACAC | TGATCGTAAG | GTGGTTCCGA | GGAAGTCGGA | 1040 |
|  | luGluHisTh | rAspArgLys | ValValProA | rgLysSerGl |  |

FIG.7B pToxo-P29

```
         10         20         30         40
1234567890 1234567890 1234567890 1234567890
GGGCAAGCGA AGCTTCAAAG ACTTGCTGAA GAAGCTCGCG   1080
uGlyLysArg SerPheLysA spLeuLeuLy sLysLeuAla

CTGCCGGCTG TTGGTATGGG TGCATCGTAT TTTGCCGCTG   1120
LeuProAlaV alGlyMetGl yAlaSerTyr PheAlaAlaA

ATAGACTTGT GCCGGAACTA ACAGAGGAGC AACAGAGAGG   1160
spArgLeuVa lProGluLeu ThrGluGluG lnGlnArgGl

CGACGAACCC CTAACCACCG GCCAGAATGT GGGCACTGTG   1200
yAspGluPro LeuThrThrG lyGlnAsnVa lGlyThrVal

TTAGGCTTCG CAGCGCTTGC TGCTGCCGCA GCGTTCCTTG   1240
LeuGlyPheA laAlaLeuAl aAlaAlaAla AlaPheLeuG

GCATGGGTCT CACGAGGACG TACCGACATT TTTCCCCACG   1280
lyMetGlyLe uThrArgThr TyrArgHisP heSerProAr

CAAAAACAGA TCACGGCAGC CTGCACTCGA GCAAGAGGTG   1320
gLysAsnArg SerArgGlnP roAlaLeuGl uGlnGluVal

CCTGAATCAG GCGAAGATGG GGAGGATGCC CGCCAGCGGA   1360
ProGluSerG lyGluAspGl yGluAspAla ArgGlnArgI

TCCGTCTGCA GACGCGTCTT GAAACCGTTG GCGATAACTT   1400
leArgLeuGl nThrArgLeu GluThrValG lyAspAsnPh

CCTGCGTCAT CTTGGTATTT ATGGCTACCG TGCAGGCTTT   1440
eLeuArgHis LeuGlyIleT yrGlyTyrAr gAlaGlyPhe

ATCCGTCGTT ACGTCAACTG GCAGCCAAGT CCGTTAGAAC   1480
IleArgArgT yrValAsnTr pGlnProSer ProLeuGluH

ACATCGAAAT GTTAGAGCAG CTTCGTGTTC TGTGGTACGG   1520
isIleGluMe tLeuGluGln LeuArgValL euTrpTyrGl

CGAAAAAATC CATGTTGCTG TTGCTCAGGA AGTTCCTGGC   1560
yGluLysIle HisValAlaV alAlaGlnGl uValProGly
```

FIG.7C pToxo-P29

```
          10         20         30         40
 1234567890 1234567890 1234567890 1234567890
ACAGGTGTGG ATACCCCTGA AGATCTCGAC CCATCTACCA    1600
ThrGlyValA spThrProGl uAspLeuAsp ProSerThrA

ATTCGTCTTC TGTTCCGGGT GATCCGCTAG ACTGCCGTCA    1640
snSerSerSe rValProGly AspProLeuA spCysArgHi

CGCTAAGTAA GTAGATCTTG AGCGCGTTCG CGCTGAAATG    1680
sAlaLys

CGCTAATTTC ACTTCACGAC ACTTCAGCCA ATTTTGGGAG    1720

GAGTGTCGTA CCGTTACGAT TTTCCTCAAT TTTTCTTTTC    1760

AACAATTGAT CTCATTCAGG TGACATCTTT TATATTGGCG    1800

CTCATTATGA AAGCAGTAGC TTTTATGAGG GTAATCTGAA    1840

TGGAACAGCT GCGTGCCGAA TTAAGCCATT TACTGGGCGA    1880

AAAACTCAGT CGTATTGAGT GCGTCAATGA AAAAGCGGAT    1920

ACGGCGTTGT GGGCTTTGTA TGACAGCCAG GGAAACCCAA    1960

TGCCGTTAAT GGCAAGAAGC TTAGCCCGCC TAATGAGCGG    2000

GCTTTTTTTT CGACGCGAGG CTGGATGGCC TTCCCCATTA    2040

TGATTCTTCT CGCTTCCGGC GGCATCGGGA TGCCCGCGTT    2080
```

FIG.7D pToxo-P29

```
         10         20         30         40
1234567890 1234567890 1234567890 1234567890
GCAGGCCATG CTGTCCAGGC AGGTAGATGA CGACCATCAG    2120

GGACAGCTTC AAGGATCGCT CGCGGCTCTT ACCAGCCTAA    2160

CTTCGATCAC TGGACCGCTG ATCGTCACGG CGATTTATGC    2200

CGCCTCGGCG AGCACATGGA ACGGGTTGGC ATGGATTGTA    2240

GGCGCCGCCC TATACCTTGT CTGCCTCCCC GCGTTGCGTC    2280

GCGGTGCATG GAGCCGGGCC ACCTCGACCT GAATGGAAGC    2320

CGGCGGCACC TCGCTAACGG ATTCACCACT CCAAGAATTG    2360

GAGCCAATCA ATTCTTGCGG AGAACTGTGA ATGCGCAAAC    2400

CAACCCTTGG CAGAACATAT CCATCGCGTC CGCCATCTCC    2440

AGCAGCCGCA CGCGGCGCAT CTCGGGCAGC GTTGGGTCCT    2480

GGCCACGGGT GCGCATGATC GTGCTCCTGT CGTTGAGGAC    2520

CCGGCTAGGC TGGCGGGGTT GCCTTACTGG TTAGCAGAAT    2560

GAATCACCGA TACGCGAGCG AACGTGAAGC GACTGCTGCT    2600
```

FIG. 7E pToxo-P29

```
         10         20         30         40
1234567890 1234567890 1234567890 1234567890
GCAAAACGTC TGCGACCTGA GCAACAACAT GAATGGTCTT     2640

CGGTTTCCGT GTTTCGTAAA GTCTGGAAAC GCGGAAGTCA     2680

GCGCCCTGCA CCATTATGTT CCGGATCTGC ATCGCAGGAT     2720

GCTGCTGGCT ACCCTGTGGA ACACCTACAT CTGTATTAAC     2760

GAAGCGCTTC TTCCGCTTCC TCGCTCACTG ACTCGCTGCG     2800

CTCGGTCGTT CGGCTGCGGC GAGCGGTATC AGCTCACTCA     2840

AAGGCGGTAA TACGGTTATC CACAGAATCA GGGGATAACG     2880

CAGGAAAGAA CATGTGAGCA AAAGGCCAGC AAAAGGCCAG     2920

GAACCGTAAA AAGGCCGCGT TGCTGGCGTT TTTCCATAGG     2960

CTCCGCCCCC CTGACGAGCA TCACAAAAAT CGACGCTCAA     3000

GTCAGAGGTG GCGAAACCCG ACAGGACTAT AAAGATACCA     3040

GGCGTTTCCC CCTGGAAGCT CCCTCGTGCG CTCTCCTGTT     3080

CCGACCCTGC CGCTTACCGG ATACCTGTCC GCCTTTCTCC     3120
```

FIG. 7F pToxo-P29

```
         10         20         30         40
1234567890 1234567890 1234567890 1234567890
CTTCGGGAAG CGTGGCGCTT TCTCAATGCT CACGCTGTAG    3160

GTATCTCAGT TCGGTGTAGG TCGTTCGCTC CAAGCTGGGC    3200

TGTGTGCACG AACCCCCCGT TCAGCCCGAC CGCTGCGCCT    3240

TATCCGGTAA CTATCGTCTT GAGTCCAACC CGGTAAGACA    3280

CGACTTATCG CCACTGGCAG CAGCCACTGG TAACAGGATT    3320

AGCAGAGCGA GGTATGTAGG CGGTGCTACA GAGTTCTTGA    3360

AGTGGTGGCC TAACTACGGC TACACTAGAA GGACAGTATT    3400

TGGTATCTGC GCTCTGCTGA AGCCAGTTAC CTTCGGAAAA    3440

AGAGTTGGTA GCTCTTGATC CGGCAAACAA ACCACCGCTG    3480

GTAGCGGTGG TTTTTTTGTT TGCAAGCAGC AGATTACGCG    3520

CAGAAAAAAA GGATCTCAAG AAGATCCTTT GATCTTTTCT    3560

ACGGGGTCTG ACGCTCAGTG GAACGAAAAC TCACGTTAAG    3600

GGATTTTGGT CATGAGATTA TCAAAAAGGA TCTTCACCTA    3640
```

FIG. 7G pToxo-P29

```
         10          20          30          40
1234567890  1234567890  1234567890  1234567890
GATCCTTTTA  AATTAAAAAT  GAAGTTTTAA  ATCAATCTAA    3680

AGTATATATG  AGTAAACTTG  GTCTGACAGT  TACCAATGCT    3720

TAATCAGTGA  GGCACCTATC  TCAGCGATCT  GTCTATTTCG    3760

TTCATCCATA  GTTGCCTGAC  TCCCCGTCGT  GTAGATAACT    3800

ACGATACGGG  AGGGCTTACC  ATCTGGCCCC  AGTGCTGCAA    3840

TGATACCGCG  AGACCCACGC  TCACCGGCTC  CAGATTTATC    3880

AGCAATAAAC  CAGCCAGCCG  GAAGGGCCGA  GCGCAGAAGT    3920

GGTCCTGCAA  CTTTATCCGC  CTCCATCCAG  TCTATTAATT    3960

GTTGCCGGGA  AGCTAGAGTA  AGTAGTTGCG  CAGTTAATAG    4000

TTTGCGCAAC  GTTGTTGCCA  TTGCTACAGG  CATCGTGGTG    4040

TCACGCTCGT  CGTTTGGTAT  GGCTTCATTC  AGCTCCGGTT    4080

CCCAACGATC  AAGGCGAGTT  ACATGATCCC  CCATGTTGTG    4120

CAAAAAAGCG  GTTAGCTCCT  TCGGTCCTCC  GATCGTTGTC    4160
```

FIG.7H pToxo-P29

```
          10          20          30          40
 1234567890  1234567890  1234567890  1234567890
 AGAAGTAAGT  TGGCCGCAGT  GTTATCACTC  ATGGTTATGG   4200

CAGCACTGCA  TAATTCTCTT  ACTGTCATGC  CATCCGTAAG   4240

ATGCTTTTCT  GTGACTGGTG  AGTACTCAAC  CAAGTCATTC   4280

TGAGAATAGT  GTATGCGGCG  ACCGAGTTGC  TCTTGCCCGG   4320

CGTCAACACG  GGATAATACC  GCGCCACATA  GCAGAACTTT   4360

AAAAGTGCTC  ATCATTGGAA  AACGTTCTTC  GGGGCGAAAA   4400

CTCTCAAGGA  TCTTACCGCT  GTTGAGATCC  AGTTCGATGT   4440

AACCCACTCG  TGCACCCAAC  TGATCTTCAG  CATCTTTTAC   4480

TTTCACCAGC  GTTTCTGGGT  GAGCAAAAAC  AGGAAGGCAA   4520

AATGCCGCAA  AAAAGGGAAT  AAGGGCGACA  CGGAAATGTT   4560

GAATACTCAT  ACTCTTCCTT  TTTCAATATT  ATTGAAGCAT   4600

TTATCAGGGT  TATTGTCTCA  TGAGCGGATA  CATATTTGAA   4640

TGTATTTAGA  AAAATAAACA  AATAGGGGTT  CCGCGCACAT   4680
```

FIG. 71

```
          10         20         30         40
 1234567890 1234567890 1234567890 1234567890
TTCCCCGAAA AGTGCCACCT GACGTCTAAG AAACCATTAT    4720

TATCATGACA TTAACCTATA AAAATAGGCG TATCACGAGG    4760

CCCTTTCGTC TTCAA                              4775
```

FIG.7J pToxo-P30

| 10<br>1234567890 | 20<br>1234567890 | 30<br>1234567890 | 40<br>1234567890 | |
|---|---|---|---|---|
| GAATTAATTC | CCATTAATGT | GAGTTAGCTC | ACTCATTAGG | 40 |
| CACCCCAGGC | TTTACACTTT | ATGTTCCGGC | TCGTATTTTG | 80 |
| TGTGGAATTG | TGAGCGGATA | ACAATTGGGC | ATCCAGTAAG | 120 |
| GAGGTTTAAA<br> | TGAGTTTTGT<br>M etSerPheVa | GGTCATTATT<br>lValIleIle | CCCGCGCGCT<br>ProAlaArgT | 160 |
| ACGCGACGTC<br>yrAlaThrSe | GCGTCTGCCC<br>rArgLeuPro | GGTAAACCAT<br>GlyLysProL | TGGTTGATAT<br>euValAspIl | 200 |
| TAACGGCAAA<br>eAsnGlyLys | CCCATGATTG<br>ProMetIleV | TTCATGTTCT<br>alHisValLe | TGAACGCGCG<br>uGluArgAla | 240 |
| CGTGAATCAG<br>ArgGluSerG | GTGCCGAGCG<br>lyAlaGluAr | CATCATCGTG<br>gIleIleVal | GCAACCGATC<br>AlaThrAspH | 280 |
| ATGAGGATGT<br>isGluAspVa | TGCCCGCGCC<br>lAlaArgAla | GTTGAAGCCG<br>ValGluAlaA | CTGGCGGTGA<br>laGlyGlyGl | 320 |
| AGTATGTATG<br>uValCysMet | ACGCGCGCCG<br>ThrArgAlaA | ATCATCAGTC<br>spHisGlnSe | AGGAACAGAA<br>rGlyThrGlu | 360 |
| CGTCTGGCGG<br>ArgLeuAlaG | AAGTTGTCGA<br>luValValGl | AAAATGCGCA<br>uLysCysAla | TTCAGCGACG<br>PheSerAspA | 400 |
| ACACGGTGAT<br>spThrValIl | CGTTAATGTG<br>eValAsnVal | CAGGGTGATG<br>GlnGlyAspG | AACCGATGAT<br>luProMetIl | 440 |
| CCCTGCGACA<br>eProAlaThr | ATCATTCGTC<br>IleIleArgG | AGGTTGCTGA<br>lnValAlaAs | TAACCTCGCT<br>pAsnLeuAla | 480 |
| CAGCGTCAGG<br>GlnArgGlnV | TGGGTATGAC<br>alGlyMetTh | GACTCTGGCG<br>rThrLeuAla | GTGCCAATCC<br>ValProIleH | 520 |

FIG.9A pToxo-P30

```
         10         20         30         40
1234567890 1234567890 1234567890 1234567890
ACAATGCGGA AGAAGCGTTT AACCCGAATG CGGTGAAAGT    560
isAsnAlaGl uGluAlaPhe AsnProAsnA laValLysVa

GGTTCTCGAC GCTGAAGGGT ATGCACTGTA CTTCTCTCGC    600
lValLeuAsp AlaGluGlyT yrAlaLeuTy rPheSerArg

GCCACCATTC CTTGGGATCG TGATCGTTTT GCAGAAGGCC    640
AlaThrIleP roTrpAspAr gAspArgPhe AlaGluGlyL

TTAATTCGAT GCTTGTTGCC AATCAAGTTG TCACCTGCCC    680
euAsnSerMe tLeuValAla AsnGlnValV alThrCysPr

AGATAAAAAA TCGACAGCCG CGGTCATTCT CACACCGACG    720
oAspLysLys SerThrAlaA laValIleLe uThrproThr GAGAACCACT TCACTCTCAA GTGCCCTAAA ACAGCGCTCA    760
GlnAsnHisP heThrLeuLy sCysProLys ThrAlaLeuT CAGAGCCTCC CACTCTTGCG TACTCACCCA ACAGGCAAAT    800
hrGluProPr oThrLeuAla TyrSerProA snArgGlnIl CTGCCCAGCG GGTACTACAA GTAGCTGTAC ATCAAAGGCT    840
eCysProAla GlyThrThrS erSerCysTh rSerLysAla GTAACATTGA GCTCCTTGAT TCCTGAAGCA GAAGATAGCT    880
ValThrLeuS erSerLeuIl eProGluAla GluAspSerT GGTGGACGGG GGATTCTGCT AGTCTCGACA CGGCAGGCAT    920
rpTrpThrGl yAspSerAla SerLeuAspT hrAlaGlyIl CAAACTCACA GTTCCAATCG AGAAGTTCCC CGTGACAACG    960
eLysLeuThr ValProIleG luLysPhePr oValThrThr CAGACGTTTG TGGTCGGTTG CATCAAGGGA GACGACGCAC   1000
GlnThrPheV alValGlyCy sIleLysGly AspAspAlaG AGAGTTGTAT GGTCACGGTG ACAGTACAAG CCAGAGCCTC   1040
lnSerCysMe tValThrVal ThrValGlnA laArgAlaSe
```

FIG.9B pToxo-P30

```
         10         20         30         40
1234567890 1234567890 1234567890 1234567890
ATCGGTCGTC AATAATGTCG CAAGGTGCTC CTACGGTGCA    1080
rSerValVal AsnAsnValA laArgCysSe rTyrGlyAla

GACAGCACTC TTGGTCCTGT CAAGTTGTCT GCGGAAGGAC    1120
AspSerThrL euGlyProVa lLysLeuSer AlaGluGLyP

CCACTACAAT GACCCTCGTG TGCGGGAAAG ATGGAGTCAA    1160
roThrThrMe tThrLeuVal CysGlyLysA spGlyValLy

AGTTCCTCAA GACAACAATC AGTACTGTTC CGGGACGACG    1200
sValProGln AspAsnAsnG lnTyrCysSe rGlyThrThr

CTGACTGGTT GCAACGAGAA ATCGTTCAAA GATATTTTGC    1240
LeuThrGlyC ysAsnGluLy sSerPheLys AspIleLeuP

CAAAATTAAC TGAGAACCCG TGGCAGGGTA ACGCTTCGAG    1280
roLysLeuTh rGluAsnPro TrpGlnGlyA snAlaSerSe

TGATAAGGGT GCCACGCTAA CGATCAAGAA GGAAGCATTT    1320
rAspLysGly AlaThrLeuT hrIleLysLy sGluAlaPhe

CCAGCCGAGT CAAAAAGCGT CATTATTGGA TGCACAGGGG    1360
ProAlaGluS erLysSerVa lIleIleGly CysThrGlyG

GATCGCCTGA GAAGCATCAC TGTACCGTGA AACTGGAGTT    1400
lySerProGl uLysHisHis CysThrValL ysLeuGluPh

TGCCGGGGCT GCAGGGTCAG CAAAATCGGC TGCGGGAACA    1440
eAlaGlyAla AlaGlySerA laLysSerAl aALaGlyThr

GCCAGTCACG TTTCCATTTT TGCCATGGTG ATCGGACTTA    1480
AlaSerHisV alSerIlePh eAlaMetVal IleGlyLeuI

TTGGCTCTAT CGCAGCTTGT GTCGCGACGC GTCTTGAAAC    1520
leGlySerIl eAlaAlaCys ValAlaThrA rgLeuGluTh

CGTTGGCGAT AACTTCCTGC GTCATCTTGG TATTTATGGC    1560
rValGlyAsp AsnPheLeuA rgHisLeuGl yIleTyrGly
```

FIG.9C pToxo-P30

```
            10         20         30         40
   1234567890 1234567890 1234567890 1234567890
   TACCGTGCAG GCTTTATCCG TCGTTACGTC AACTGGCAGC   1600
   TyrArgAlaG lyPheIleAr gArgTyrVal AsnTrpGlnP

CAAGTCCGTT AGAACACATC GAAATGTTAG AGCAGCTTCG   1640
   roSerProLe uGluHisIle GluMetLeuG luGlnLeuAr

TGTTCTGTGG TACGGCGAAA AAATCCATGT TGCTGTTGCT   1680
   gValLeuTrp TyrGlyGluL ysIleHisVa lAlaValAla

CAGGAAGTTC CTGGCACAGG TGTGGATACC CCTGAAGATC   1720
   GlnGluValP roGlyThrGl yValAspThr ProGluAspL

TCGACCCGTC GACGAATTCG AGCTCGGTAC CCGGGGATCC   1760
   euAspProSe rThrAsnSer SerSerValP roGlyAspPr

TCTAGACTGC AGGCATGCTA AGTAAGTAGA TCTTGAGCGC   1800
   oLeuAspCys ArgHisAlaL ys

GTTCGCGCTG AAATGCGCTA ATTCACTTC  ACGACACTTC    1840

AGCCAATTTT GGGAGGAGTG TCGTACCGTT ACGATTTTCC   1880

TCAATTTTTC TTTTCAACAA TTGATCTCAT TCAGGTGACA   1920

TCTTTTATAT TGGCGCTCAT TATGAAAGCA GTAGCTTTTA   1960

TGAGGGTAAT CTGAATGGAA CAGCTGCGTG CCGAATTAAG   2000

CCATTTACTG GGCGAAAAAC TCAGTCGTAT TGAGTGCGTC   2040

AATGAAAAAG CGGATACGGC GTTGTGGGCT TTGTATGACA   2080
```

FIG.9D pToxo-P30

```
         10         20         30         40
1234567890 1234567890 1234567890 1234567890
GCCAGGGAAA CCCAATGCCG TTAATGGCAA GAAGCTTAGC    2120

CCGCCTAATG AGCGGGCTTT TTTTTCGACG CGAGGCTGGA    2160

TGGCCTTCCC CATTATGATT CTTCTCGCTT CCGGCGGCAT    2200

CGGGATGCCC GCGTTGCAGG CCATGCTGTC CAGGCAGGTA    2240

GATGACGACC ATCAGGGACA GCTTCAAGGA TCGCTCGCGG    2280

CTCTTACCAG CCTAACTTCG ATCACTGGAC CGCTGATCGT    2320

CACGGCGATT TATGCCGCCT CGGCGAGCAC ATGGAACGGG    2360

TTGGCATGGA TTGTAGGCGC CGCCCTATAC CTTGTCTGCC    2400

TCCCCGCGTT GCGTCGCGGT GCATGGAGCC GGGCCACCTC    2440

GACCTGAATG GAAGCCGGCG GCACCTCGCT AACGGATTCA    2480

CCACTCCAAG AATTGGAGCC AATCAATTCT TGCGGAGAAC    2520

TGTGAATGCG CAAACCAACC CTTGGCAGAA CATATCCATC    2560

GCGTCCGCCA TCTCCAGCAG CCGCACGCGG CGCATCTCGG    2600
```

FIG.9E pToxo-P30

```
          10         20         30         40
 1234567890 1234567890 1234567890 1234567890
 GCAGCGTTGG GTCCTGGCCA CGGGTGCGCA TGATCGTGCT   2640

CCTGTCGTTG AGGACCCGGC TAGGCTGGCG GGGTTGCCTT   2680

ACTGGTTAGC AGAATGAATC ACCGATACGC GAGCGAACGT   2720

GAAGCGACTG CTGCTGCAAA ACGTCTGCGA CCTGAGCAAC   2760

AACATGAATG GTCTTCGGTT TCCGTGTTTC GTAAAGTCTG   2800

GAAACGCGGA AGTCAGCGCC CTGCACCATT ATGTTCCGGA   2840

TCTGCATCGC AGGATGCTGC TGGCTACCCT GTGGAACACC   2880

TACATCTGTA TTAACGAAGC GCTTCTTCCG CTTCCTCGCT   2920

CACTGACTCG CTGCGCTCGG TCGTTCGGCT GCGGCGAGCG   2960

GTATCAGCTC ACTCAAAGGC GGTAATACGG TTATCCACAG   3000

AATCAGGGGA TAACGCAGGA AAGAACATGT GAGCAAAAGG   3040

CCAGCAAAAG GCCAGGAACC GTAAAAAGGC CGCGTTGCTG   3080

GCGTTTTTCC ATAGGCTCCG CCCCCCTGAC GAGCATCACA   3120
```

FIG.9F pToxo-P30

```
          10         20         30         40
 1234567890 1234567890 1234567890 1234567890
 AAAATCGACG CTCAAGTCAG AGGTGGCGAA ACCCGACAGG  3160

ACTATAAAGA TACCAGGCGT TTCCCCCTGG AAGCTCCCTC  3200

GTGCGCTCTC CTGTTCCGAC CCTGCCGCTT ACCGGATACC  3240

TGTCCGCCTT TCTCCCTTCG GGAAGCGTGG CGCTTTCTCA  3280

ATGCTCACGC TGTAGGTATC TCAGTTCGGT GTAGGTCGTT  3320

CGCTCCAAGC TGGGCTGTGT GCACGAACCC CCCGTTCAGC  3360

CCGACCGCTG CGCCTTATCC GGTAACTATC GTCTTGAGTC  3400

CAACCCGGTA AGACACGACT TATCGCCACT GGCAGCAGCC  3440

ACTGGTAACA GGATTAGCAG AGCGAGGTAT GTAGGCGGTG  3480

CTACAGAGTT CTTGAAGTGG TGGCCTAACT ACGGCTACAC  3520

TAGAAGGACA GTATTTGGTA TCTGCGCTCT GCTGAAGCCA  3560

GTTACCTTCG GAAAAAGAGT TGGTAGCTCT TGATCCGGCA  3600

AACAAACCAC CGCTGGTAGC GGTGGTTTTT TTGTTTGCAA  3640
```

FIG.9G pToxo-P30

|  |  |  |  |  |
|---|---|---|---|---|
| GCAGCAGATT | ACGCGCAGAA | AAAAAGGATC | TCAAGAAGAT | 3680 |
| CCTTTGATCT | TTTCTACGGG | GTCTGACGCT | CAGTGGAACG | 3720 |
| AAAACTCACG | TTAAGGGATT | TTGGTCATGA | GATTATCAAA | 3760 |
| AAGGATCTTC | ACCTAGATCC | TTTTAAATTA | AAAATGAAGT | 3800 |
| TTTAAATCAA | TCTAAAGTAT | ATATGAGTAA | ACTTGGTCTG | 3840 |
| ACAGTTACCA | ATGCTTAATC | AGTGAGGCAC | CTATCTCAGC | 3880 |
| GATCTGTCTA | TTTCGTTCAT | CCATAGTTGC | CTGACTCCCC | 3920 |
| GTCGTGTAGA | TAACTACGAT | ACGGGAGGGC | TTACCATCTG | 3960 |
| GCCCCAGTGC | TGCAATGATA | CCGCGAGACC | CACGCTCACC | 4000 |
| GGCTCCAGAT | TTATCAGCAA | TAAACCAGCC | AGCCGGAAGG | 4040 |
| GCCGAGCGCA | GAAGTGGTCC | TGCAACTTTA | TCCGCCTCCA | 4080 |
| TCCAGTCTAT | TAATTGTTGC | CGGGAAGCTA | GAGTAAGTAG | 4120 |
| TTCGCCAGTT | AATAGTTTGC | GCAACGTTGT | TGCCATTGCT | 4160 |

FIG.9H pToxo-P30

```
          10         20         30         40
 1234567890 1234567890 1234567890 1234567890
 ACAGGCATCG TGGTGTCACG CTCGTCGTTT GGTATGGCTT   4200

CATTCAGCTC CGGTTCCCAA CGATCAAGGC GAGTTACATG   4240

ATCCCCCATG TTGTGCAAAA AAGCGGTTAG CTCCTTCGGT   4280

CCTCCGATCG TTGTCAGAAG TAAGTTGGCC GCAGTGTTAT   4320

CACTCATGGT TATGGCAGCA CTGCATAATT CTCTTACTGT   4360

CATGCCATCC GTAAGATGCT TTTCTGTGAC TGGTGAGTAC   4400

TCAACCAAGT CATTCTGAGA ATAGTGTATG CGGCGACCGA   4440

GTTGCTCTTG CCCGGCGTCA ACACGGGATA ATACCGCGCC   4480

ACATAGCAGA ACTTTAAAAG TGCTCATCAT TGGAAAACGT   4520

TCTTCGGGGC GAAAACTCTC AAGGATCTTA CCGCTGTTGA   4560

GATCCAGTTC GATGTAACCC ACTCGTGCAC CCAACTGATC   4600

TTCAGCATCT TTTACTTTCA CCAGCGTTTC TGGGTGAGCA   4640

AAAACAGGAA GGCAAAATGC CGCAAAAAAG GGAATAAGGG   4680
```

FIG. 91 pToxo-P30

|  | 10 | 20 | 30 | 40 | |
|---|---|---|---|---|---|
|  | 1234567890 | 1234567890 | 1234567890 | 1234567890 | |
| | CGACACGGAA | ATGTTGAATA | CTCATACTCT | TCCTTTTTCA | 4720 |
| | ATATTATTGA | AGCATTTATC | AGGGTTATTG | TCTCATGAGC | 4760 |
| | GGATACATAT | TTGAATGTAT | TTAGAAAAAT | AAACAAATAG | 4800 |
| | GGGTTCCGCG | CACATTTCCC | CGAAAAGTGC | CACCTGACGT | 4840 |
| | CTAAGAAACC | ATTATTATCA | TGACATTAAC | CTATAAAAAT | 4880 |
| | AGGCGTATCA | CGAGGCCCTT | TCGTCTTCAA | | 4910 |

FIG.9J pToxo-P35S

```
          10         20         30         40
 1234567890 1234567890 1234567890 1234567890
GAATTAATTC CCATTAATGT GAGTTAGCTC ACTCATTAGG    40

CACCCCAGGC TTTACACTTT ATGTTCCGGC TCGTATTTTG    80

TGTGGAATTG TGAGCGGATA ACAATTGGGC ATCCAGTAAG   120

GAGGTTTAAA TGAGTTTTGT GGTCATTATT CCCGCGCGCT   160
         M etSerPheVa lValIleIle ProAlaArgT

ACGCGTCGAC GCGTCTGCCC GGTAAACCAT TGGTTGATAT   200
yrAlaSerTh rArgLeuPro GlyLysProL euValAspIl

TAACGGCAAA CCCATGATTG TTCATGTTCT TGAACGCGCG   240
eAsnGlyLys ProMetIleV alHisValLe uGluArgAla

CGTGAATCAG GTGCCGAGCG CATCATCGTG GCAACCGATC   280
ArgGluSerG lyAlaGluAr gIleIleVal AlaThrAspH

ATGAGGATGT TGCCCGCGCC GTTGAAGCCG CTGGCGGTGA   320
isGluAspVa lAlaArgAla ValGluAlaA laGlyGlyGl

AGTATGTATG ACGCGCGCCG ATCATCAGTC AGGAACAGAA   360
uValCysMet ThrArgAlaA spHisGlnSe rGlyThrGlu

CGTCTGGCGG AAGTTGTCGA AAAATGCGCA TTCAGCGACG   400
ArgLeuAlaG luValValGl uLysCysAla PheSerAspA

ACACGGTGAT CGTTAATGTG CAGGGTGATG AACCGATGAT   440
spThrValIl eValAsnVal GlnGlyAspG luProMetIl

CCCTGCGACA ATCATTCGTC AGGTTGCTGA TAACCTCGCT   480
eProAlaThr IleIleArgG lnValAlaAs pAsnLeuAla

CAGCGTCAGG TGGGTATGAC GACTCTGGCG GTGCCAATCC   520
GlnArgGlnV alGlyMetTh rThrLeuAla ValProIleH
```

FIG.11A pToxo-P35S

```
           10          20          30          40
  1234567890  1234567890  1234567890  1234567890
  ACAATGCGGA  AGAAGCGTTT  AACCCGAATG  CGGTGAAAGT    560
  isAsnALaGl  uGluAlaPhe  AsnProAsnA  laValLysVa

GGTTCTCGAC  GCTGAAGGGT  ATGCACTGTA  CTTCTCTCGC    600
  lValLeuAsp  AlaGluGlyT  yrAlaLeuTy  rPheSerArg

GCCACCATTC  GTTGGGATCG  TGATCGTTTT  GCAGAAGGCC    640
  AlaThrIleP  roTrpAspAr  gAspArgPhe  AlaGluGlyI

TTATGAACGG  TCCTTTGAGT  TATCATCCAA  GCAGTTACGG    680
  euMetAsnGl  yProLeuSer  TyrHisProS  erSerTyrGl

AGCGTCGTAT  CCGAATCCGA  GTAATCCTCT  GCATGGAATG    720
  yAlaSerTyr  ProAsnProS  erAsnProLe  uHisGlyMet

CCCAAGCCAG  AGAACCCGGT  GAGACCGCCT  CCTCCCGGTT    760
  ProLysProG  luAsnProVa  lArgProPro  ProProGlyP

TCCATCCAAG  CGTTATTCCC  AATCCCCCGT  ACCCGCTGGG    800
  heHisProSe  rValIlePro  AsnProProT  yrProLeuGl

CACTCCAGCG  AGCATGCCAC  AGCCAGAGGT  TCCGCCACTT    840
  yThrProAla  SerMetProG  lnProGluVa  lProProLeu

CAGCATCCCC  CGCCAACGGG  TTCCCCTCCC  GCGGCCGCTC    880
  GlnHisProP  roProThrGl  ySerProPro  AlaAlaAlaP

CCCAGCCTCC  ATATCCAGTG  GGTACTCCAG  TAATGCCACA    920
  roGlnProPr  oTyrProVal  GlyThrProV  alMetProGl

GCCAGAGATA  CCGCCTGTTC  ATCGGCCGCC  GCCTCCGGGT    960
  nProGluIle  ProProValH  isArgProPr  oProProGly

TTCCGTCCCG  AAGTGGCTCC  CGTGCCCCCG  TATCCAGTGG   1000
  PheArgProG  luValAlaPr  oValProPro  TyrProValG

GCACTCCAAC  GGGCATGCCC  CAGCCGGAGA  TACCGGCAGT   1040
  lyThrProTh  rGlyMetPro  GlnProGluI  leProAlaVa
```

FIG.11B pToxo-P35S

| 10 | 20 | 30 | 40 | |
|---|---|---|---|---|
| 1234567890 | 1234567890 | 1234567890 | 1234567890 | |
| TCACCATACG | CGTCTTGAAA | CCGTTGGCGA | TAACTTCCTG | 1080 |
| lHisHisThr | ArgLeuGluT | hrValGlyAs | pAsnPheLeu | |
| | | | | |
| CGTCATCTTG | GTATTTATGG | CTACCGTGCA | GGCTTTATCC | 1120 |
| ArgHisLeuG | lyIleTyrGl | yTyrArgAla | GlyPheIleA | |
| | | | | |
| GTCGTTACGT | CAACTGGCAG | CCAAGTCCGT | TAGAACACAT | 1160 |
| rgArgTyrVa | lAsnTrpGln | ProSerProL | euGluHisIl | |
| | | | | |
| CGAAATGTTA | GAGCAGCTTC | GTGTTCTGTG | GTACGGCGAA | 1200 |
| eGluMetLeu | GluGlnLeuA | rgValLeuTr | pTyrGlyGlu | |
| | | | | |
| AAAATCCATG | TTGCTGTTGC | TCAGGAAGTT | CCTGGCACAG | 1240 |
| LysIleHisV | alAlaValAl | aGlnGluVal | ProGlyThrG | |
| | | | | |
| GTGTGGATAC | CCCTGAAGAT | CTCGACCCGT | CGACGAATTC | 1280 |
| lyValAspTh | rProGluAsp | LeuAspProS | erThrAsnSe | |
| | | | | |
| GAGCTCGGTA | CCCGGGGATC | CTCTAGACTG | CAGGCATGCT | 1320 |
| rSerSerVal | ProGlyAspP | roLeuAspCy | sArgHisAla | |
| | | | | |
| AAGTAAGTAG | ATCTTGAGCG | CGTTCGCGCT | GAAATGCGCT | 1360 |
| Lys | | | | |
| | | | | |
| AATTTCACTT | CACGACACTT | CAGCCAATTT | TGGGAGGAGT | 1400 |
| | | | | |
| GTCGTACCGT | TACGATTTTC | CTCAATTTTT | CTTTTCAACA | 1440 |
| | | | | |
| ATTGATCTCA | TTCAGGTGAC | ATCTTTTATA | TTGGCGCTCA | 1480 |
| | | | | |
| TTATGAAAGC | AGTAGCTTTT | ATGAGGGTAA | TCTGAATGGA | 1520 |
| | | | | |
| ACAGCTGCGT | GCCGAATTAA | GCCATTTACT | GGGCGAAAAA | 1560 |

FIG. 11C pToxo-P35S

```
         10         20         30         40
1234567890 1234567890 1234567890 1234567890
CTCAGTCGTA TTGAGTGCGT CAATGAAAAA GCGGATACGG    1600

CGTTGTGGGC TTTGTATGAC AGCCAGGGAA ACCCAATGCC    1640

GTTAATGGCA AGAAGCTTAG CCCGCCTAAT GAGCGGGCTT    1680

TTTTTTCGAC GCGAGGCTGG ATGGCCTTCC CCATTATGAT    1720

TCTTCTCGCT TCCGGCGGCA TCGGGATGCC CGCGTTGCAG    1760

GCCATGCTGT CCAGGCAGGT AGATGACGAC CATCAGGGAC    1800

AGCTTCAAGG ATCGCTCGCG GCTCTTACCA GCCTAACTTC    1840

GATCACTGGA CCGCTGATCG TCACGGCGAT TTATGCCGCC    1880

TCGGCGAGCA CATGGAACGG GTTGGCATGG ATTGTAGGCG    1920

CCGCCCTATA CCTTGTCTGC CTCCCCGCGT TGCGTCGCGG    1960

TGCATGGAGC CGGGCCACCT CGACCTGAAT GGAAGCCGGC    2000

GGCACCTCGC TAACGGATTC ACCACTCCAA GAATTGGAGC    2040

CAATCAATTC TTGCGGAGAA CTGTGAATGC GCAAACCAAC    2080
```

FIG. 11D pToxo-P35S

```
         10         20         30         40
1234567890 1234567890 1234567890 1234567890
CCTTGGCAGA ACATATCCAT CGCGTCCGCC ATCTCCAGCA    2120

GCCGCACGCG GCGCATCTCG GGCAGCGTTG GGTCCTGGCC    2160

ACGGGTGCGC ATGATCGTGC TCCTGTCGTT GAGGACCCGG    2200

CTAGGCTGGC GGGGTTGCCT TACTGGTTAG CAGAATGAAT    2240

CACCGATACG CGAGCGAACG TGAAGCGACT GCTGCTGCAA    2280

AACGTCTGCG ACCTGAGCAA CAACATGAAT GGTCTTCGGT    2320

TTCCGTGTTT CGTAAAGTCT GGAAACGCGG AAGTCAGCGC    2360

CCTGCACCAT TATGTTCCGG ATCTGCATCG CAGGATGCTG    2400

CTGGCTACCC TGTGGAACAC CTACATCTGT ATTAACGAAG    2440

CGCTTCTTCC GCTTCCTCGC TCACTGACTC GCTGCGCTCG    2480

GTCGTTCGGC TGCGGCGAGC GGTATCAGCT CACTCAAAGG    2520

CGGTAATACG GTTATCCACA GAATCAGGGG ATAACGCAGG    2560

AAAGAACATG TGAGCAAAAG GCCAGCAAAA GGCCAGGAAC    2600
```

FIG. 11E pToxo-P35S

|  | 10 | 20 | 30 | 40 | |
|---|---|---|---|---|---|
|  | 1234567890 | 1234567890 | 1234567890 | 1234567890 | |
| | CGTAAAAAGG | CCGCGTTGCT | GGCGTTTTTC | CATAGGCTCC | 2640 |
| | GCCCCCCTGA | CGAGCATCAC | AAAAATCGAC | GCTCAAGTCA | 2680 |
| | GAGGTGGCGA | AACCCGACAG | GACTATAAAG | ATACCAGGCG | 2720 |
| | TTTCCCCCTG | GAAGCTCCCT | CGTGCGCTCT | CCTGTTCCGA | 2760 |
| | CCCTGCCGCT | TACCGGATAC | CTGTCCGCCT | TTCTCCCTTC | 2800 |
| | GGGAAGCGTG | GCGCTTTCTC | AATGCTCACG | CTGTAGGTAT | 2840 |
| | CTCAGTTCGG | TGTAGGTCGT | TCGCTCCAAG | CTGGGCTGTG | 2880 |
| | TGCACGAACC | CCCCGTTCAG | CCCGACCGCT | GCGCCTTATC | 2920 |
| | CGGTAACTAT | CGTCTTGAGT | CCAACCCGGT | AAGACACGAC | 2960 |
| | TTATCGCCAC | TGGCAGCAGC | CACTGGTAAC | AGGATTAGCA | 3000 |
| | GAGCGAGGTA | TGTAGGCGGT | GCTACAGAGT | TCTTGAAGTG | 3040 |
| | GTGGCCTAAC | TACGGCTACA | CTAGAAGGAC | AGTATTTGGT | 3080 |
| | ATCTGCGCTC | TGCTGAAGCC | AGTTACCTTC | GGAAAAAGAG | 3120 |

FIG.11F pToxo-P35S

```
         10         20         30         40
1234567890 1234567890 1234567890 1234567890
TTGGTAGCTC TTGATCCGGC AAACAAACCA CCGCTGGTAG    3160

CGGTGGTTTT TTTGTTTGCA AGCAGCAGAT TACGCGCAGA    3200

AAAAAAGGAT CTCAAGAAGA TCCTTTGATC TTTTCTACGG    3240

GGTCTGACGC TCAGTGGAAC GAAAACTCAC GTTAAGGGAT    3280

TTTGGTCATG AGATTATCAA AAAGGATCTT CACCTAGATC    3320

CTTTTAAATT AAAAATGAAG TTTTAAATCA ATCTAAAGTA    3360

TATATGAGTA AACTTGGTCT GACAGTTACC AATGCTTAAT    3400

CAGTGAGGCA CCTATCTCAG CGATCTGTCT ATTTCGTTCA    3440

TCCATAGTTG CCTGACTCCC CGTCGTGTAG ATAACTACGA    3480

TACGGGAGGG CTTACCATCT GGCCCCAGTG CTGCAATGAT    3520

ACCGCGAGAC CCACGCTCAC CGGCTCCAGA TTTATCAGCA    3560

ATAAACCAGC CAGCCGGAAG GGCCGAGCGC AGAAGTGGTC    3600

CTGCAACTTT ATCCGCCTCC ATCCAGTCTA TTAATTGTTG    3640
```

FIG. 11G pToxo-P35S

```
         10         20         30         40
1234567890 1234567890 1234567890 1234567890
CCGGGAAGCT AGAGTAAGTA GTTCGCCAGT TAATAGTTTG   3680

CGCAACGTTG TTGCCATTGC TACAGGCATC GTGGTGTCAC   3720

GCTCGTCGTT TGGTATGGCT TCATTCAGCT CCGGTTCCCA   3760

ACGATCAAGG CGAGTTACAT GATCCCCCAT GTTGTGCAAA   3800

AAAGCGGTTA GCTCCTTCGG TCCTCCGATC GTTCTCAGAA   3840

GTAAGTTGGC CGCAGTGTTA TCACTCATGG TTATGGCAGC   3880

ACTGCATAAT TCTCTTACTG TCATGCCATC CGTAAGATGC   3920

TTTTCTGTGA CTGGTGAGTA CTCAACCAAG TCATTCTGAG   3960

AATAGTGTAT GCGGCGACCG AGTTGCTCTT GCCCGGCGTC   4000

AACACGGGAT AATACCGCGC CACATAGCAG AACTTTAAAA   4040

GTGCTCATCA TTGGAAAACG TTCTTCGGGG CGAAAACTCT   4080

CAAGGATCTT ACCGCTGTTG AGATCCAGTT CGATGTAACC   4120

CACTCGTGCA CCCAACTGAT CTTCAGCATC TTTTACTTTC   4160
```

FIG. 11H pToxo-P35S

| 10 | 20 | 30 | 40 | |
|---|---|---|---|---|
| 1234567890 | 1234567890 | 1234567890 | 1234567890 | |
| ACCAGCGTTT | CTGGGTGAGC | AAAAACAGGA | AGGCAAAATG | 4200 |
| CCGCAAAAAA | GGGAATAAGG | GCGACACGGA | AATGTTGAAT | 4240 |
| ACTCATACTC | TTCCTTTTTC | AATATTATTG | AAGCATTTAT | 4280 |
| CAGGGTTATT | GTCTCATGAG | CGGATACATA | TTTGAATGTA | 4320 |
| TTTAGAAAAA | TAAACAAATA | GGGGTTCCGC | GCACATTTCC | 4360 |
| CCGAAAAGTG | CCACCTGACG | TCTAAGAAAC | CATTATTATC | 4400 |
| ATGACATTAA | CCTATAAAAA | TAGGCGTATC | ACGAGGCCCT | 4440 |
| TTCGTCTTCA | A | | | 4451 |

FIG.11I pToxo-P66g

```
          10         20         30         40
 1234567890 1234567890 1234567890 1234567890
 GAATTAATTC CCATTAATGT GAGTTAGCTC ACTCATTAGG    40

CACCCCAGGC TTTACACTTT ATGTTCCGGC TCGTATTTTG    80

TGTGGAATTG TGAGCGGATA ACAATTGGGC ATCCAGTAAG   120

GAGGTTTAAA TGAGTTTTGT GGTCATTATT CCCGCGCGCT   160
          M etSerPheVa lValIleIle ProAlaArgT

ACGCGTCGAC GCGTCTGCCC GGTAAACCAT TGGTTGATAT   200
 yrAlaSerTh rArgLeuPro GlyLysProL euValAspIl

TAACGGCAAA CCCATGATTG TTCATGTTCT TGAACGCGCG   240
 eAsnGlyLys ProMetIleV alHisValLe uGluArgAla

CGTGAATCAG GTGCCGAGCG CATCATCGTG GCAACCGATC   280
 ArgGluSerG lyAlaGluAr gIleIleVal AlaThrAspH

ATGAGGATGT TGCCCGCGCC GTTGAAGCCG CTGGCGGTGA   320
 isGluAspVa lAlaArgAla ValGluAlaA laGlyGlyGl

AGTATGTATG ACGCGCGCCG ATCATCAGTC AGGAACAGAA   360
 uValCysMet ThrArgAlaA spHisGlnSe rGlyThrGlu

CGTCTGGCGG AAGTTGTCGA AAAATGCGCA TTCAGCGACG   400
 ArgLeuAlaG luValValGl uLysCysAla PheSerAspA

ACACGGTGAT CGTTAATGTG CAGGGTGATG AACCGATGAT   440
 spThrValIl eValAsnVal GlnGlyAspG luProMetIl

CCCTGCGACA ATCATTCGTC AGGTTGCTGA TAACCTCGCT   480
 eProAlaThr IleIleArgG lnValAlaAs pAsnLeuAla

CAGCGTCAGG TGGGTATGAC GACTCTGGCG GTGCCAATCC   520
 GlnArgGlnV alGlyMetTh rThrLeuAla ValProIleH
```

FIG.13A pToxo-P66g

```
          10         20         30         40
 1234567890 1234567890 1234567890 1234567890
ACAATGCGGA AGAAGCGTTT AACCCGAATG CGGTGAAAGT    560
isAsnAlaGl uGluAlaPhe AsnProAsnA laValLysVa

GGTTCTCGAC GCTGAAGGGT ATGCACTGTA CTTCTCTCGC    600
lValLeuAsp AlaGluGlyT yrAlaLeuTy rPheSerArg

GCCACCATTC CTTGGGATCG TGATCGTTTT GCAGAAGGCC    640
AlaThrIleP roTrpAspAr gAspArgPhe AlaGluGlyL

TTATGAGCCA CAATGGAGTC CCCGCTTATC CATCGTATGC    680
euMetSerHi sAsnGlyVal ProAlaTyrP roSerTyrAl

ACAGGTATCG CTCTCTTCCA ACGGCGAGCC ACGGCACAGG    720
aGlnValSer LeuSerSerA snGlyGluPr oArgHisArg

GGCATACGCG GCAGCTTCCT CATGTCCGTA AAGCCACACG    760
GlyIleArgG lySerPheLe uMetSerVal LysProHisA

CAAACGCTGA TGACTTCGCC TCCGACGACA ACTACGAACC    800
laAsnAlaAs pAspPheAla SerAspAspA snTyrGluPr

GCTGCCGAGT TTCGTGGAAG CTCCTGTCAG AGGCCCGGAC    840
oLeuProSer PheValGluA laProValAr gGlyProAsp

CAAGTCCCTG CCAGAGGAGA AGCTGCTCTT GTCACAGAGG    880
GlnValProA laArgGlyGl uAlaAlaLeu ValThrGluG

AGACTCCAGC GCAACAGCCG GCGGTGGCTC TAGGCAGTGC    920
aGluGlyGlu GlyThrSerT hrThrGluSe rAlaSerGlu

AATTCTGAAG ATGATGACAC GTTTCACGAT GCCCTCCAAG   1000
AsnSerGluA spAspAspTh rPheHisAsp AlaLeuGlnG

AGCTTCCAGA GGATGGCCTC GAAGTGCGCC CACCAAATGC   1040
luLeuProGl uAspGlyLeu GluValArgP roProAsnAl
```

FIG. 13B pToxo-P66g

```
         10         20         30         40
1234567890 1234567890 1234567890 1234567890
ACAGGAGCTG CCCCCACCAA ATGTACAGGA GCTGCCCCCA   1080
aGluGluLeu ProProProA snValGlnGl uLeuProPro

CCAAATGTAC AGGAGCTGCC CCCACCAACT GAACAGGAGC   1120
ProAsnValG lnGluLeuPr oProProThr GluGlnGluL

TGCCCCCACC AACTGAACAG GAGCTGCCCC CACCAACTGA   1160
euProProPr oThrGluGln GluLeuProP roProThrGl

ACAGGAGCTG CCCCCACCAA CTGAACAGGA GCTACCCCCA   1200
uGlnGluLeu ProProProT hrGluGlnGl uLeuProPro

TCAACTGAAC AGGAGCTGCC CCCACCAGTG GGCGAAGGTC   1240
SerThrGluG lnGluLeuPr oProProVal GlyGluGlyG

AACGTCTGCA AGTCCCTGGG GAACATGGGC CACAGGGGCC   1280
lnArgLeuGl nValProGly GluHisGlyP roGlnGlyPr

CCCATACGAT GATCAGCAGC TGCTTTTAGA GCCTACGGAA   1320
oProTyrAsp AspGlnGlnL euLeuLeuGl uProThrGlu

GAGCAACAGG AGGGCCCTCA GGAGCCGCTG CCACCGCCGC   1360
GluGlnGlnG luGlyProGl nGluProLeu ProProProP

CGCCCCCGAC TCGGGGCGAA CAACCCGAAG GACAGCAGCC   1400
roProProTh rArgGlyGlu GlnProGluG lyGlnGlnPr

GCAGGGACCA GTTCGTCAAA ATTTTTTTCG TCGGGCGTTG   1440
oGlnGlyPro ValArgGlnA snPhePheAr gArgAlaLeu

GGGGCCGCAA GAAGCCGATT CGGAGGTGCA CGACGCCATG   1480
GlyAlaAlaA rgSerArgPh eGlyGlyAla ArgArgHisV

TCAGTGGGGT GTTCCGAAGA GTCAGAGGTG GTTTGAACCG   1520
alSerGlyVa lPheArgArg ValArgGlyG lyLeuAsnAr

TATAGTAGGT GGAGTGAGGA GTGGTTTCAG GCGTGCAAGA   1560
gIleValGly GlyValArgS erGlyPheAr gArgAlaArg
```

FIG.13C pToxo-P66g

```
         10         20         30         40
1234567890 1234567890 1234567890 1234567890
GAAGGTGTCG TTGGGGGAGT CCGTCGTTTA ACAAGTGGTG    1600
GluGlyValV alGlyGlyVa lArgArgLeu ThrSerGlyA

CCAGTCTGGG TCTCCGTCGT GTAGGAGAAG GTTTACGTAG    1640
laSerLeuGl yLeuArgArg ValGlyGluG lyLeuArgAr

GAGTTTCTAT CGTGTAAGAG GAGCTGTCAG TAGCGGTCGT    1680
gSerPheTyr ArgValArgG lyAlaValSe rSerGlyArg

AGGCGTGCAG CAGATGGTGC CAGCAATGTA AGAGAAAGAT    1720
ArgArgAlaA laAspGlyAl aSerAsnVal ArgGluArgP

TCGTTGCCGC AGGCGGGAGA GTCAGAGACG CTTTCGGCGC    1760
heValAlaAl aGlyGlyArg ValArgAspA laPheGlyAl

GGGATTGACG CGCCTCCGCA GGCGCGGCAG AACTAATGGC    1800
aGlyLeuThr ArgLeuArgA rgArgGlyAr gThrAsnGly

GAGGAGGGCA GGCCCCTACT GGGCGAAGGA AGAGAGCAGG    1840
GluGluGlyA rgProLeuLe uGlyGluGly ArgGluGlnA

ATGATGGATC GCAAACGCGT CTTGAAACCG TTGGCGATAA    1880
spAspGlySe rGlnThrArg LeuGluThrV alGlyAspAs

CTTCCTGCGT CATCTTGGTA TTTATGGCTA CCGTGCAGGC    1920
nPheLeuArg HisLeuGlyI leTyrGlyTy rArgAlaGly

TTTATCCGTC GTTACGTCAA CTGGCAGCCA AGTCCGTTAG    1960
PheIleArgA rgTyrValAs nTrpGlnPro SerProLeuG

AACACATCGA AATGTTAGAG CAGCTTCGTG TTCTGTGGTA    2000
luHisIleGl uMetLeuGlu GlnLeuArgV alLeuTrpTy

CGGCGAAAAA ATCCATGTTG CTGTTGCTCA GGAAGTTCCT    2040
rGlyGluLys IleHisValA laValAlaGl nGluValPro

GGCACAGGTG TGGATACCCC TGAAGATCTC GACCCGTCGA    2080
GlyThrGlyV alAspThrPr oGluAspLeu AspProSerT
```

FIG. 13D pToxo-P66g

|  10 | 20 | 30 | 40 | |
|---|---|---|---|---|
| 1234567890 | 1234567890 | 1234567890 | 1234567890 | |
| CGAATTCGAG | CTCGGTACCC | GGGGATCCTC | TAGACTGCAG | 2120 |
| hrAsnSerSe | rSerValPro | GlyAspProL | euAspCysAr | |
| GCATGCTAAG | TAAGTAGATC | TTGAGCGCGT | TCGCGCTGAA | 2160 |
| gHisAlaLys | | | | |
| ATGCGCTAAT | TTCACTTCAC | GACACTTCAG | CCAATTTTGG | 2200 |
| GAGGAGTGTC | GTACCGTTAC | GATTTTCCTC | AATTTTTCTT | 2240 |
| TTCAACAATT | GATCTCATTC | AGGTGACATC | TTTTATATTG | 2280 |
| GCGCTCATTA | TGAAAGCAGT | AGCTTTTATG | AGGGTAATCT | 2320 |
| GAATGGAACA | GCTGCGTGCC | GAATTAAGCC | ATTTACTGGG | 2360 |
| CGAAAAACTC | AGTCGTATTG | AGTGCGTCAA | TGAAAAAGCG | 2400 |
| GATACGGCGT | TGTGGGCTTT | GTATGACAGC | CAGGGAAACC | 2440 |
| CAATGCCGTT | AATGGCAAGA | AGCTTAGCCC | GCCTAATGAG | 2480 |
| CGGGCTTTTT | TTTCGACGCG | AGGCTGGATG | GCCTTCCCCA | 2520 |
| TTATGATTCT | TCTCGCTTCC | GGCGGCATCG | GGATGCCCGC | 2560 |
| GTTGCAGGCC | ATGCTGTCCA | GGCAGGTAGA | TGACGACCAT | 2600 |

FIG.13E pToxo-P66g

```
          10         20         30         40
   1234567890 1234567890 1234567890 1234567890
   CAGGGACAGC TTCAAGGATC GCTCGCGGCT CTTACCAGCC    2640

TAACTTCGAT CACTGGACCG CTGATCGTCA CGGCGATTTA    2680

TGCCGCCTCG GCGAGCACAT GGAACGGGTT GGCATGGATT    2720

GTAGGCGCCG CCCTATACCT TGTCTGCCTC CCCGCGTTGC    2760

GTCGCGGTGC ATGGAGCCGG GCCACCTCGA CCTGAATGGA    2800

AGCCGGCGGC ACCTCGCTAA CGGATTCACC ACTCCAAGAA    2840

TTGGAGCCAA TCAATTCTTG CGGAGAACTG TGAATGCGCA    2880

AACCAACCCT TGGCAGAACA TATCCATCGC GTCCGCCATC    2920

TCCAGCAGCC GCACGCGGCG CATCTCGGGC AGCGTTGGGT    2960

CCTGGCCACG GGTGCGCATG ATCGTGCTCC TGTCGTTGAG    3000

GACCCGGCTA GGCTGGCGGG GTTGCCTTAC TGGTTAGCAG    3040

AATGAATCAC CGATACGCGA GCGAACGTGA AGCGACTGCT    3080

GCTGCAAAAC GTCTGCGACC TGAGCAACAA CATGAATGGT    3120
```

FIG. 13F pToxo-P66g

```
         10         20         30         40
1234567890 1234567890 1234567890 1234567890
CTTCGGTTTC CGTGTTTCGT AAAGTCTGGA AACGCGGAAG    3160

TCAGCGCCCT GCACCATTAT GTTCCGGATC TGCATCGCAG    3200

GATGCTGCTG GCTACCCTGT GGAACACCTA CATCTGTATT    3240

AACGAAGCGC TTCTTCCGCT TCCTCGCTCA CTGACTCGCT    3280

GCGCTCGGTC GTTCGGCTGC GGCGAGCGGT ATCAGCTCAC    3320

TCAAAGGCGG TAATACGGTT ATCCACAGAA TCAGGGGATA    3360

ACGCAGGAAA GAACATGTGA GCAAAAGGCC AGCAAAAGGC    3400

CAGGAACCGT AAAAAGGCCG CGTTGCTGGC GTTTTTCCAT    3440

AGGCTCCGCC CCCCTGACGA GCATCACAAA AATCGACGCT    3480

CAAGTCAGAG GTGGCGAAAC CCGACAGGAC TATAAAGATA    3520

CCAGGCGTTT CCCCCTGGAA GCTCCCTCGT GCGCTCTCCT    3560

GTTCCGACCC TGCCGCTTAC CGGATACCTG TCCGCCTTTC    3600

TCCCTTCGGG AAGCGTGGCG CTTTCTCAAT GCTCACGCTG    3640
```

FIG. 13G pToxo-P66g

```
         10         20         30         40
1234567890 1234567890 1234567890 1234567890
TAGGTATCTC AGTTCGGTGT AGGTCGTTCG CTCCAAGCTG   3680

GGCTGTGTGC ACGAACCCCC CGTTCAGCCC GACCGCTGCG   3720

CCTTATCCGG TAACTATCGT CTTGAGTCCA ACCCGGTAAG   3760

ACACGACTTA TCGCCACTGG CAGCAGCCAC TGGTAACAGG   3800

ATTAGCAGAG CGAGGTATGT AGGCGGTGCT ACAGAGTTCT   3840

TGAAGTGGTG GCCTAACTAC GGCTACACTA GAAGGACAGT   3880

ATTTGGTATC TGCGCTCTGC TGAAGCCAGT TACCTTCGGA   3920

AAAAGAGTTG GTAGCTCTTG ATCCGGCAAA CAAACCACCG   3960

CTGGTAGCGG TGGTTTTTTT GTTTGCAAGC AGCAGATTAC   4000

GCGCAGAAAA AAAGGATCTC AAGAAGATCC TTTGATCTTT   4040

TCTACGGGGT CTGACGCTCA GTGGAACGAA AACTCACGTT   4080

AAGGGATTTT GGTCATGAGA TTATCAAAAA GGATCTTCAC   4120

CTAGATCCTT TTAAATTAAA AATGAAGTTT TAAATCAATC   4160
```

FIG.13H pToxo-P66g

```
         10         20         30         40
1234567890 1234567890 1234567890 1234567890
TAAAGTATAT ATGAGTAAAC TTGGTCTGAC AGTTACCAAT    4200

GCTTAATCAG TGAGGCACCT ATCTCAGCGA TCTGTCTATT    4240

TCGTTCATCC ATAGTTGCCT GACTCCCCGT CGTGTAGATA    4280

ACTACGATAC GGGAGGGCTT ACCATCTGGC CCCAGTGCTG    4320

CAATGATACC GCGAGACCCA CGCTCACCGG CTCCAGATTT    4360

ATCAGCAATA AACCAGCCAG CCGGAAGGGC CGAGCGCAGA    4400

AGTGGTCCTG CAACTTTATC CGCCTCCATC CAGTCTATTA    4440

ATTGTTGCCG GGAAGCTAGA GTAAGTAGTT CGCCAGTTAA    4480

TAGTTTGCGC AACGTTGTTG CCATTGCTAC AGGCATCGTG    4520

GTGTCACGCT CGTCGTTTGG TATGGCTTCA TTCAGCTCCG    4560

GTTCCCAACG ATCAAGGCGA GTTACATGAT CCCCCATGTT    4600

GTGCAAAAAA GCGGTTAGCT CCTTCGGTCC TCCGATCGTT    4640

GTCAGAAGTA AGTTGGCCGC AGTGTTATCA CTCATGGTTA    4680
```

FIG. 13I pToxo-P66g

```
         10         20         30         40
1234567890 1234567890 1234567890 1234567890
TGGCAGCACT GCATAATTCT CTTACTGTCA TGCCATCCGT    4720

AAGATGCTTT TCTGTGACTG GTGAGTACTC AACCAAGTCA    4760

TTCTGAGAAT AGTGTATGCG GCGACCGAGT TGCTCTTGCC    4800

CGGCGTCAAC ACGGGATAAT ACCGCGCCAC ATAGCAGAAC    4840

TTTAAAAGTG CTCATCATTG GAAAACGTTC TTCGGGGCGA    4880

AAACTCTCAA GGATCTTACC GCTGTTGAGA TCCAGTTCGA    4920

TGTAACCCAC TCGTGCACCC AACTGATCTT CAGCATCTTT    4960

TACTTTCACC AGCGTTTCTG GGTGAGCAAA AACAGGAAGG    5000

CAAAATGCCG CAAAAAAGGG AATAAGGGCG ACACGGAAAT    5040

GTTGAATACT CATACTCTTC CTTTTTCAAT ATTATTGAAG    5080

CATTTATCAG GGTTATTGTC TCATGAGCGG ATACATATTT    5120

GAATGTATTT AGAAAAATAA ACAAATAGGG GTTCCGCGCA    5160

CATTTCCCCG AAAAGTGCCA CCTGACGTCT AAGAAACCAT    5200
```

FIG.13J pToxo-P66g

```
         10         20         30         40
1234567890 1234567890 1234567890 1234567890
TATTATCATG ACATTAACCT ATAAAAATAG GCGTATCACG              5240

AGGCCCTTTC GTCTTCAA                                     5258
```

FIG.13K

SEQUENCE LISTING

<160> NUMBER OF SEQ ID NOS: 55

<210> SEQ ID NO 1
<211> LENGTH: 43
<212> TYPE: DNA
<213> ORGANISM: Toxoplasma gondii

<400> SEQUENCE: 1
cgcagaattc gatgtccacc accgagacgc cagcgcccat tga          43

<210> SEQ ID NO 2
<211> LENGTH: 43
<212> TYPE: DNA
<213> ORGANISM: Toxoplasma gondii

<400> SEQUENCE: 2
cccgggatcc ttacacaaac gtgatcaaca aacctgcgag acc          43

<210> SEQ ID NO 3
<211> LENGTH: 36
<212> TYPE: DNA
<213> ORGANISM: Toxoplasma gondii

<400> SEQUENCE: 3
ggccgaattc gatggccgaa ggcggcgaca accagt                  36

<210> SEQ ID NO 4
<211> LENGTH: 38
<212> TYPE: DNA
<213> ORGANISM: Toxoplasma gondii

<400> SEQUENCE: 4
gcccggatcc ttactctctc tctcctgtta ggaaccca                38

<210> SEQ ID NO 5
<211> LENGTH: 39
<212> TYPE: DNA

-continued

<213> ORGANISM: Toxoplasma gondii

<400> SEQUENCE: 5
ggcgaattcg atgcaagagg aaatcaaaga agggtgga                              39

<210> SEQ ID NO 6
<211> LENGTH: 33
<212> TYPE: DNA
<213> ORGANISM: Toxoplasma gondii

<400> SEQUENCE: 6
cgcactctag atcacctcgg agtcgagccc aac                                   33

<210> SEQ ID NO 7
<211> LENGTH: 34
<212> TYPE: DNA
<213> ORGANISM: Toxoplasma gondii

<400> SEQUENCE: 7
ggcgaattcg atgagcggta aacctcttga tgag                                  34

<210> SEQ ID NO 8
<211> LENGTH: 32
<212> TYPE: DNA
<213> ORGANISM: Toxoplasma gondii

<400> SEQUENCE: 8
cgctaggatc cttactgcga aaagtctggg ac                                    32

<210> SEQ ID NO 9
<211> LENGTH: 37
<212> TYPE: DNA
<213> ORGANISM: Toxoplasma gondii

<400> SEQUENCE: 9
ggcgaattcg atgcttgttg ccaatcaagt tgtcacc                               37

<210> SEQ ID NO 10
<211> LENGTH: 31
<212> TYPE: DNA
<213> ORGANISM: Toxoplasma gondii

<400> SEQUENCE: 10
cgctaggatc ctcacgcgac acaagctgcg a                                     31

<210> SEQ ID NO 11
<211> LENGTH: 35
<212> TYPE: DNA
<213> ORGANISM: Toxoplasma gondii

<400> SEQUENCE: 11
gacggcgaat tcgatgaacg gtcctttgag ttatc                                 35

<210> SEQ ID NO 12
<211> LENGTH: 32
<212> TYPE: DNA
<213> ORGANISM: Toxoplasma gondii

<400> SEQUENCE: 12
cgctaggatc cttaattctg cgtcgttacg gt                                    32

<210> SEQ ID NO 13
<211> LENGTH: 35

```
<212> TYPE: DNA
<213> ORGANISM: Toxoplasma gondii

<400> SEQUENCE: 13
gacggcgaat tcgatgaacg gtcctttgag ttatc                              35

<210> SEQ ID NO 14
<211> LENGTH: 36
<212> TYPE: DNA
<213> ORGANISM: Toxoplasma gondii

<400> SEQUENCE: 14
cgctaggatc ctcaatggtg aactgccggt atctcc                             36

<210> SEQ ID NO 15
<211> LENGTH: 34
<212> TYPE: DNA
<213> ORGANISM: Toxoplasma gondii

<400> SEQUENCE: 15
ggcgaattcg atgggtgagt gcagctttgg ttct                               34

<210> SEQ ID NO 16
<211> LENGTH: 34
<212> TYPE: DNA
<213> ORGANISM: Toxoplasma gondii

<400> SEQUENCE: 16
cgcactctag atcactcttt gcgcattctt tcca                               34

<210> SEQ ID NO 17
<211> LENGTH: 40
<212> TYPE: DNA
<213> ORGANISM: Toxoplasma gondii

<400> SEQUENCE: 17
gcctgaattc gatgcacgta cagcaaggcg ctggcgttgt                         40

<210> SEQ ID NO 18
<211> LENGTH: 42
<212> TYPE: DNA
<213> ORGANISM: Toxoplasma gondii

<400> SEQUENCE: 18
cgctaggatc ctcagaagtc tccatggctt gcaatgggag ga                      42

<210> SEQ ID NO 19
<211> LENGTH: 40
<212> TYPE: DNA
<213> ORGANISM: Toxoplasma gondii

<400> SEQUENCE: 19
ggcgaattcg atgagccaca atggagtccc cgcttatcca                         40

<210> SEQ ID NO 20
<211> LENGTH: 40
<212> TYPE: DNA
<213> ORGANISM: Toxoplasma gondii

<400> SEQUENCE: 20
cgctaggatc cttattgcga tccatcatcc tgctctcttc                         40

<210> SEQ ID NO 21
```

<210> SEQ ID NO 21
<211> LENGTH: 38
<212> TYPE: DNA
<213> ORGANISM: Toxoplasma gondii

<400> SEQUENCE: 21
acccgaattc gatgacagca accgtaggat tgagccaa                                38

<210> SEQ ID NO 22
<211> LENGTH: 34
<212> TYPE: DNA
<213> ORGANISM: Toxoplasma gondii

<400> SEQUENCE: 22
cgctggatcc tcaagctgcc tgttccgcta agat                                    34

<210> SEQ ID NO 23
<211> LENGTH: 1268
<212> TYPE: DNA
<213> ORGANISM: Toxoplasma gondii

<400> SEQUENCE: 23
gaattcggca cgaggcgaac tggggcaaag ccgccgccac cagttcgcta ccgcggccac        60
cgcgtcagat gacgaactga tgagtcgaat ccgaaattct gacttttcg atggtcaagc        120 acccgttgac agtctcagac cgacgaacgc cggtgtcgac tcgaaaggga ccgacgatca       180
cctcaccacc agcatggata aggcatctgt agagagtcag cttccgagaa gagagccatt       240
ggagacggag ccagatgaac aagaagaagt tcatttcagg aagcgaggcg tccgttccga       300
cgctgaagtg actgacgaca acatctacga ggagcacact gatcgtaagg tggttccgag       360
gaagtcggag ggcaagcgaa gcttcaaaga cttgctgaag aagctcgcgc tgccggctgt       420
tggtatgggt gcatcgtatt ttgccgctga tagacttgtg ccggaactaa cagaggagca       480
acagagaggc gacgaacccc taaccaccgg ccagaatgtg ggcactgtgt taggcttcgc       540
agcgcttgct gctgccgcag cgttccttgg catgggtctc acgaggacgt accgacattt       600
ttccccacgc aaaaacagat cacggcagcc tgcactcgag caagaggtgc ctgaatcagg       660
cgaagatggg gaggatgccc gccagtagga tatgggggct aataaaagtg agtaggagct       720
cgaggacagt gtcccgaacg cgcctgagag gcagacagac acagaagagt gaagaaaaac       780
aacatggtat tacgtgcggt gagtgtttgc tgtcacgtgt tttttgcgcc acaaagacag       840
cttgtgttgt atgcatggga tcgacagttc atggacggcg ctacccagag aggcggcatt       900
tgcgtacacc gtgggtcgtc atgagtaccg ggacatcgtg ttcgtgttta tttgttcatg       960
tcgaagtgca ctaagacacg agacgaaagg gtggttccgc ccctggcagc atcacgtagt      1020
ggtttctttg tcgagaacag cggcagtccg aggccacttg agacaggatg tttgagtgta      1080
tacagacaac gtggtcacag catgaggcaa agctgtctaa gcagccattt gcgcgagcga      1140
agtcatccat gccgactgtg tgagcctctt tcgtcacttt gaatgagaca gaaactaaga      1200
ctcgcagcag gtctgaatat tgcgaataat ctacttttaa aaccaaaaaa aaaaaaaaa       1260 aactcgag                                                              1268

<210> SEQ ID NO 24
<211> LENGTH: 228
<212> TYPE: PRT
<213> ORGANISM: Toxoplasma gondii

<400> SEQUENCE: 24

Asn Ser Ala Arg Gly Glu Leu Gly Gln Ser Arg Arg His Gln Phe Ala

-continued

```
          1               5               10              15
        Thr Ala Ala Thr Ala Ser Asp Asp Glu Leu Met Ser Arg Ile Arg Asn
                         20              25              30
        Ser Asp Phe Phe Asp Gly Gln Ala Pro Val Asp Ser Leu Arg Pro Thr
                     35              40              45
        Asn Ala Gly Val Asp Ser Lys Gly Thr Asp His Leu Thr Thr Ser
             50              55              60
        Met Asp Lys Ala Ser Val Glu Ser Gln Leu Pro Arg Arg Glu Pro Leu
        65              70              75              80
        Glu Thr Glu Pro Asp Glu Gln Glu Val His Phe Arg Lys Arg Gly
                         85              90              95
        Val Arg Ser Asp Ala Glu Val Thr Asp Asp Asn Ile Tyr Glu Glu His
                     100             105             110
        Thr Asp Arg Lys Val Val Pro Arg Lys Ser Glu Gly Lys Arg Ser Phe
                     115             120             125
        Lys Asp Leu Leu Lys Lys Leu Ala Leu Pro Ala Val Gly Met Gly Ala
             130             135             140
        Ser Tyr Phe Ala Ala Asp Arg Leu Val Pro Glu Leu Thr Glu Glu Gln
        145             150             155             160
        Gln Arg Gly Asp Glu Pro Leu Thr Thr Gly Gln Asn Val Gly Thr Val
                         165             170             175
        Leu Gly Phe Ala Ala Leu Ala Ala Ala Ala Phe Leu Gly Met Gly
                     180             185             190
        Leu Thr Arg Thr Tyr Arg His Phe Ser Pro Arg Lys Asn Arg Ser Arg
                     195             200             205
        Gln Pro Ala Leu Glu Gln Glu Val Pro Glu Ser Gly Glu Asp Gly Glu
             210             215             220
        Asp Ala Arg Gln
        225
```

<210> SEQ ID NO 25
<211> LENGTH: 477
<212> TYPE: DNA
<213> ORGANISM: Toxoplasma gondii

<400> SEQUENCE: 25

| | | | | | |
|---|---|---|---|---|---|
| agaccccgcc | accgcccgtg | acgaaccacg | aaccgcggcg | aacggcgagc | tcaccgggtt | 60 |
| ttcagagacg | cgcgagatcc | ctgatttcgt | ttaccattga | cgcccgccgc | cgtcgacgtc | 120 |
| tttggaacgt | gtttcacgtt | tgagttgcac | tgttactttc | ttcggattac | attcttccac | 180 |
| taaaagctgg | ttttgtccag | tatccattcg | tcgctaccgt | tgcgcagtca | cgttgaattt | 240 |
| tgcagcggca | aaacatcttg | tgtaaaattc | gagttttgtt | gatgattgaa | gtaccctata | 300 |
| ttggggcttg | ctaacgtttt | gtattaaaag | ggattactgc | ggcgtctcat | ttccaaaatg | 360 |
| gcccgacacg | caattttttc | cgcgctttgt | gttttaggcc | tggtggcggc | ggctttgccc | 420 |
| cagttcgcta | ccgcggccac | cgcgtcagat | gacgaactga | tgagtcgaat | ccgaaat | 477 |

<210> SEQ ID NO 26
<211> LENGTH: 1648
<212> TYPE: DNA
<213> ORGANISM: Toxoplasma gondii

<400> SEQUENCE: 26

| | | | | | |
|---|---|---|---|---|---|
| agaccccgcc | accgcccgtg | acgaaccacg | aaccgcggcg | aacggcgagc | tcaccgggtt | 60 |
| ttcagagacg | cgcgagatcc | ctgatttcgt | ttaccattga | cgcccgccgc | cgtcgacgtc | 120 |

```
tttggaacgt gtttcacgtt tgagttgcac tgttactttc ttcggattac attcttccac    180
taaaagctgg ttttgtccag tatccattcg tcgctaccgt tgcgcagtca cgttgaattt    240
tgcagcggca aaacatcttg tgtaaaattc gagttttgtt gatgattgaa gtaccctata    300
ttggggcttg ctaacgtttt gtattaaaag ggattactgc ggcgtctcat ttccaaaatg    360
gcccgacacg caatttttc cgcgctttgt gttttaggcc tggtggcggc ggctttgccc     420
cagttcgcta ccgcgccac cgcgtcagat gacgaactga tgagtcgaat ccgaaattct     480
gacttttcg atggtcaagc acccgttgac agtctcagac cgacgaacgc cggtgtcgac     540
tcgaaaggga ccgacgatca cctcaccacc agcatggata aggcatctgt agagagtcag    600
cttccgagaa gagagccatt ggagacggag ccagatgaac aagaagaagt tcatttcagg    660
aagcgaggcg tccgttccga cgctgaagtg actgacgaca acatctacga ggagcacact    720
gatcgtaagg tggttccgag gaagtcggag ggcaagcgaa gcttcaaaga cttgctgaag    780
aagctcgcgc tgccggctgt tggtatgggt gcatcgtatt ttgccgctga tagacttgtg    840
ccggaactaa cagaggagca acagagaggc gacgaacccc taaccaccgg ccagaatgtg    900
ggcactgtgt taggcttcgc agcgcttgct gctgccgcag cgttccttgg catgggtctc    960
acgaggacgt accgacattt tccccacgc aaaaacagat cacggcagcc tgcactcgag     1020
caagaggtgc ctgaatcagg cgaagatggg gaggatgccc gccagtagga tatggggct     1080
aataaaagtg agtaggagct cgaggacagt gtcccgaacg cgcctgagag cagacagac     1140
acagaagagt gaagaaaaac aacatggtat tacgtgcggt gagtgtttgc tgtcacgtgt    1200
ttttttgcgcc acaaagacag cttgtgttgt atgcatggga tcgacagttc atggacggcg   1260
ctacccagag aggcggcatt tgcgtacacc gtgggtcgtc atgagtaccg ggacatcgtg    1320
ttcgtgttta tttgttcatg tcgaagtgca ctaagcacg agacgaaagg gtggttccgc     1380
ccctggcagc atcacgtagt ggtttctttg tcgagaacag cggcagtccg aggccacttg    1440
agacaggatg tttgagtgta tacagacaac gtggtcacag catgaggcaa agctgtctaa    1500
gcagccattt gcgcgagcga agtcatccat gccgactgtg tgagcctctt tcgtcacttt    1560
gaatgagaca gaaactaaga ctcgcagcag gtctgaatat tgcgaataat ctactttaa    1620
aaccaaaaaa aaaaaaaaaa aactcgag                                       1648
```

<210> SEQ ID NO 27
<211> LENGTH: 236
<212> TYPE: PRT
<213> ORGANISM: Toxoplasma gondii

<400> SEQUENCE: 27

```
Met Ala Arg His Ala Ile Phe Ser Ala Leu Cys Val Leu Gly Leu Val
 1               5                  10                  15

Ala Ala Ala Leu Pro Gln Phe Ala Thr Ala Ala Thr Ala Ser Asp Asp
            20                  25                  30

Glu Leu Met Ser Arg Ile Arg Asn Ser Asp Phe Phe Asp Gly Gln Ala
        35                  40                  45

Pro Val Asp Ser Leu Arg Pro Thr Asn Ala Gly Val Asp Ser Lys Gly
    50                  55                  60

Thr Asp Asp His Leu Thr Thr Ser Met Asp Lys Ala Ser Val Glu Ser
65                  70                  75                  80

Gln Leu Pro Arg Arg Glu Pro Leu Glu Thr Glu Pro Asp Glu Gln Glu
                85                  90                  95
```

```
Glu Val His Phe Arg Lys Arg Gly Val Arg Ser Asp Ala Glu Val Thr
            100                 105                 110

Asp Asp Asn Ile Tyr Glu Glu His Thr Asp Arg Lys Val Val Pro Arg
            115                 120                 125

Lys Ser Glu Gly Lys Arg Ser Phe Lys Asp Leu Leu Lys Lys Leu Ala
        130                 135                 140

Leu Pro Ala Val Gly Met Gly Ala Ser Tyr Phe Ala Ala Asp Arg Leu
145                 150                 155                 160

Val Pro Glu Leu Thr Glu Glu Gln Gln Arg Gly Asp Glu Pro Leu Thr
                165                 170                 175

Thr Gly Gln Asn Val Gly Thr Val Leu Gly Phe Ala Ala Leu Ala Ala
            180                 185                 190

Ala Ala Ala Phe Leu Gly Met Gly Leu Thr Arg Thr Tyr Arg His Phe
        195                 200                 205

Ser Pro Arg Lys Asn Arg Ser Arg Gln Pro Ala Leu Glu Gln Glu Val
            210                 215                 220

Pro Glu Ser Gly Glu Asp Gly Glu Asp Ala Arg Gln
225                 230                 235

<210> SEQ ID NO 28
<211> LENGTH: 78
<212> TYPE: DNA
<213> ORGANISM: Toxoplasma gondii

<400> SEQUENCE: 28
agatctcgac ccgtcgacga attcgagctc ggtacccggg gatcctctag actgcaggca    60
tgctaagtaa gtagatct                                                 78

<210> SEQ ID NO 29
<211> LENGTH: 78
<212> TYPE: DNA
<213> ORGANISM: Toxoplasma gondii

<400> SEQUENCE: 29
agatctcgac ccatctacca attcgtcttc tgttccgggt gatccgctag actgccgtca    60
cgctaagtaa gtagatct                                                 78

<210> SEQ ID NO 30
<211> LENGTH: 88
<212> TYPE: DNA
<213> ORGANISM: Toxoplasma gondii

<400> SEQUENCE: 30
cctgaagatc tcgacccatc taccaattcg tcttctgttc cgggtgatcc gctagactgc    60
cgtcacgcta gtaagtaga tcttgact                                       88

<210> SEQ ID NO 31
<211> LENGTH: 88
<212> TYPE: DNA
<213> ORGANISM: Toxoplasma gondii

<400> SEQUENCE: 31
agtcaagatc tacttactta gcgtgacggc agtctagcgg atcacccgga acagaagacg    60
aattggtaga tgggtcgaga tcttcagg                                      88

<210> SEQ ID NO 32
<211> LENGTH: 40
<212> TYPE: DNA
```

<210> SEQ ID NO 33
<211> LENGTH: 32
<212> TYPE: DNA
<213> ORGANISM: Toxoplasma gondii

<400> SEQUENCE: 32
aggcctgaat tcgagctctg ggatccgtct gcagacgcgt    40

<210> SEQ ID NO 33
<211> LENGTH: 32
<212> TYPE: DNA
<213> ORGANISM: Toxoplasma gondii

<400> SEQUENCE: 33
cctgaattcg agctctggga tccgtctgca ga    32

<210> SEQ ID NO 34
<211> LENGTH: 36
<212> TYPE: DNA
<213> ORGANISM: Toxoplasma gondii

<400> SEQUENCE: 34
cgcgtctgca gacggatccc agagctcgaa ttcagg    36

<210> SEQ ID NO 35
<211> LENGTH: 36
<212> TYPE: DNA
<213> ORGANISM: Toxoplasma gondii

<400> SEQUENCE: 35
acttagaatt cgatggcccg acacgcaatt ttttcc    36

<210> SEQ ID NO 36
<211> LENGTH: 35
<212> TYPE: DNA
<213> ORGANISM: Toxoplasma gondii

<400> SEQUENCE: 36
acatggatcc gctggcgggc atcctcccca tcttc    35

<210> SEQ ID NO 37
<211> LENGTH: 4775
<212> TYPE: DNA
<213> ORGANISM: Toxoplasma gondii

<400> SEQUENCE: 37
gaattaattc ccattaatgt gagttagctc actcattagg cacccaggc tttacacttt    60 atgttccggc tcgtattttg tgtggaattg tgagcggata caattgggc atccagtaag    120 gaggtttaaa tgagttttgt ggtcattatt cccgcgcgct acgcgacgtc gcgtctgccc    180
ggtaaaccat tggttgatat taacggcaaa cccatgattg ttcatgttct tgaacgcgcg    240
cgtgaatcag gtgccgagcg catcatcgtg gcaaccgatc atgaggatgt tgcccgcgcc    300
gttgaagccg ctggcggtga agtatgtatg acgcgcgccg atcatcagtc aggaacagaa    360
cgtctggcgg aagttgtcga aaatgcgca ttcagcgacg acacggtgat cgttaatgtg    420
cagggtgatg aaccgatgat ccctgcgaca atcattcgtc aggttgctga taacctcgct    480
cagcgtcagg tgggtatgac gactctggcg gtgccaatcc acaatgcgga agaagcgttt    540
aacccgaatg cggtgaaagt ggttctcgac gctgaagggt atgcactgta cttctctcgc    600
gccaccattc cttgggatcg tgatcgtttt gcagaaggcc tgaattcgat ggcccgacac    660
gcaatttttt ccgcgctttg tgtttaggc ctggtggcg cggctttgcc ccagttcgct    720
accgcggcca ccgcgtcaga tgacgaactg atgagtcgaa tccgaaattc tgacttttc    780

```
gatggtcaag cacccgttga cagtctcaga ccgacgaacg ccggtgtcga ctcgaaaggg    840
accgacgatc acctcaccac cagcatggat aaggcatctg tagagagtca gcttccgaga    900
agagagccat tggagacgga gccagatgaa caagaagaag ttcatttcag gaagcgaggc    960
gtccgttccg acgctgaagt gactgacgac aacatctacg aggagcacac tgatcgtaag   1020
gtggttccga ggaagtcgga gggcaagcga agcttcaaag acttgctgaa gaagctcgcg   1080
ctgccggctg ttggtatggg tgcatcgtat tttgccgctg atagacttgt gccggaacta   1140
acagaggagc aacagagagg cgacgaaccc ctaaccaccg gccagaatgt gggcactgtg   1200
ttaggcttcg cagcgcttgc tgctgccgca gcgttccttg gcatgggtct cacgaggacg   1260
taccgacatt tttccccacg caaaaacaga tcacggcagc ctgcactcga gcaagaggtg   1320
cctgaatcag gcgaagatgg ggaggatgcc cgccagcgga tccgtctgca gacgcgtctt   1380
gaaaccgttg gcgataactt cctgcgtcat cttggtattt atggctaccg tgcaggcttt   1440
atccgtcgtt acgtcaactg gcagccaagt ccgttagaac acatcgaaat gttagagcag   1500
cttcgtgttc tgtggtacgg cgaaaaaatc catgttgctg ttgctcagga agttcctggc   1560
acaggtgtgg atacccctga agatctcgac ccatctacca attcgtcttc tgttccgggt   1620
gatccgctag actgccgtca cgctaagtaa gtagatcttg agcgcgttcg cgctgaaatg   1680
cgctaatttc acttcacgac acttcagcca attttgggag gagtgtcgta ccgttacgat   1740
tttcctcaat ttttcttttc aacaattgat ctcattcagg tgacatcttt tatattggcg   1800
ctcattatga aagcagtagc ttttatgagg gtaatctgaa tggaacagct gcgtgccgaa   1860
ttaagccatt tactgggcga aaaactcagt cgtattgagt gcgtcaatga aaaagcggat   1920
acggcgttgt gggctttgta tgacagccag ggaaacccaa tgccgttaat ggcaagaagc   1980
ttagcccgcc taatgagcgg gctttttttt cgacgcgagg ctggatggcc ttccccatta   2040
tgattcttct cgcttccggc ggcatcggga tgcccgcgtt gcaggccatg ctgtccaggc   2100
aggtagatga cgaccatcag ggacagcttc aaggatcgct cgcggctctt accagcctaa   2160
cttcgatcac tggaccgctg atcgtcacgg cgatttatgc cgcctcggcg agcacatgga   2220
acgggttggc atggattgta ggcgccgccc tataccttgt ctgcctcccc gcgttgcgtc   2280
gcggtgcatg gagccgggcc acctcgacct gaatggaagc cggcggcacc tcgctaacgg   2340
attcaccact ccaagaattg gagccaatca attcttgcgg agaactgtga atgcgcaaac   2400 caaccccttgg cagaacatat ccatcgcgtc cgccatctcc agcagccgca cgcggcgcat   2460
ctcgggcagc gttgggtcct ggccacgggt gcgcatgatc gtgctcctgt cgttgaggac   2520
ccggctaggc tggcggggtt gccttactgg ttagcagaat gaatcaccga tacgcgagcg   2580
aacgtgaagc gactgctgct gcaaaacgtc tgcgacctga gcaacaacat gaatggtctt   2640
cggtttccgt gtttcgtaaa gtctggaaac gcggaagtca gcgccctgca ccattatgtt   2700
ccggatctgc atcgcaggat gctgctggct accctgtgga acacctacat ctgtattaac   2760
gaagcgcttc ttccgcttcc tcgctcactg actcgctgcg ctcggtcgtt cggctgcggc   2820
gagcggtatc agctcactca aaggcggtaa tacggttatc cacagaatca ggggataacg   2880
caggaaagaa catgtgagca aaaggccagc aaaaggccag gaaccgtaaa aaggccgcgt   2940
tgctggcgtt tttccatagg ctccgccccc ctgacgagca tcacaaaaat cgacgctcaa   3000
gtcagaggtg gcgaaacccg acaggactat aaagatacca ggcgtttccc cctggaagct   3060
ccctcgtgcg ctctcctgtt ccgaccctgc cgcttaccgg atacctgtcc gcctttctcc   3120
```

-continued

| | | |
|---|---|---|
| cttcgggaag cgtggcgctt tctcaatgct cacgctgtag gtatctcagt tcggtgtagg | 3180 |
| tcgttcgctc caagctgggc tgtgtgcacg aaccccccgt tcagcccgac cgctgcgcct | 3240 |
| tatccggtaa ctatcgtctt gagtccaacc cggtaagaca cgacttatcg ccactggcag | 3300 |
| cagccactgg taacaggatt agcagagcga ggtatgtagg cggtgctaca gagttcttga | 3360 |
| agtggtggcc taactacggc tacactagaa ggacagtatt tggtatctgc gctctgctga | 3420 |
| agccagttac cttcggaaaa agagttggta gctcttgatc cggcaaacaa accaccgctg | 3480 |
| gtagcggtgg ttttttttgtt tgcaagcagc agattacgcg cagaaaaaaa ggatctcaag | 3540 |
| aagatccttt gatcttttct acggggtctg acgctcagtg gaacgaaaac tcacgttaag | 3600 |
| ggattttggt catgagatta tcaaaaagga tcttcaccta gatccttttta aattaaaaat | 3660 |
| gaagttttaa atcaatctaa agtatatatg agtaaacttg gtctgacagt taccaatgct | 3720 |
| taatcagtga ggcacctatc tcagcgatct gtctatttcg ttcatccata gttgcctgac | 3780 |
| tccccgtcgt gtagataact acgatacggg agggcttacc atctggcccc agtgctgcaa | 3840 |
| tgataccgcg agacccacgc tcaccggctc cagatttatc agcaataaac cagccagccg | 3900 |
| gaagggccga gcgcagaagt ggtcctgcaa ctttatccgc ctccatccag tctattaatt | 3960 |
| gttgccggga agctagagta agtagttcgc cagttaatag tttgcgcaac gttgttgcca | 4020 |
| ttgctacagg catcgtggtg tcacgctcgt cgtttggtat ggcttcattc agctccggtt | 4080 |
| cccaacgatc aaggcgagtt acatgatccc ccatgttgtg caaaaaagcg gttagctcct | 4140 |
| tcggtcctcc gatcgttgtc agaagtaagt tggccgcagt gttatcactc atggttatgg | 4200 |
| cagcactgca taattctctt actgtcatgc catccgtaag atgcttttct gtgactggtg | 4260 |
| agtactcaac caagtcattc tgagaatagt gtatgcggcg accgagttgc tcttgcccgg | 4320 |
| cgtcaacacg ggataatacc gcgccacata gcagaacttt aaaagtgctc atcattggaa | 4380 |
| aacgttcttc ggggcgaaaa ctctcaagga tcttaccgct gttgagatcc agttcgatgt | 4440 |
| aacccactcg tgcacccaac tgatcttcag catcttttac tttcaccagc gtttctgggt | 4500 |
| gagcaaaaac aggaaggcaa aatgccgcaa aaagggaat aagggcgaca cggaaatgtt | 4560 |
| gaatactcat actcttcctt tttcaatatt attgaagcat ttatcagggt tattgtctca | 4620 |
| tgagcggata catatttgaa tgtatttaga aaaataaaca aatagggggtt ccgcgcacat | 4680 |
| ttccccgaaa agtgccacct gacgtctaag aaaccattat tatcatgaca ttaacctata | 4740 |
| aaaataggcg tatcacgagg ccctttcgtc ttcaa | 4775 |

<210> SEQ ID NO 38
<211> LENGTH: 36
<212> TYPE: DNA
<213> ORGANISM: Toxoplasma gondii

<400> SEQUENCE: 38

| | |
|---|---|
| tcctaggcct taattcgatg cttgttgcca atcaag | 36 |

<210> SEQ ID NO 39
<211> LENGTH: 32
<212> TYPE: DNA
<213> ORGANISM: Toxoplasma gondii

<400> SEQUENCE: 39

| | |
|---|---|
| acatacgcgt cgcgacacaa gctgcgatag ag | 32 |

<210> SEQ ID NO 40
<211> LENGTH: 4910

<212> TYPE: DNA
<213> ORGANISM: Toxoplasma gondii

<400> SEQUENCE: 40

| | | | | | |
|---|---|---|---|---|---|
| gaattaattc | ccattaatgt | gagttagctc | actcattagg | cacccccaggc | tttacactttt 60 |
| atgttccggc | tcgtatttttg | tgtggaattg | tgagcggata | acaattgggc | atccagtaag 120 |
| gaggtttaaa | tgagttttgt | ggtcattatt | cccgcgcgct | acgcgacgtc | gcgtctgccc 180 |
| ggtaaaccat | tggttgatat | taacggcaaa | cccatgattg | ttcatgttct | tgaacgcgcg 240 |
| cgtgaatcag | gtgccgagcg | catcatcgtg | gcaaccgatc | atgaggatgt | tgcccgcgcc 300 |
| gttgaagccg | ctggcggtga | agtatgtatg | acgcgcgccg | atcatcagtc | aggaacagaa 360 |
| cgtctggcgg | aagttgtcga | aaaatgcgca | ttcagcgacg | cacggtgat | cgttaatgtg 420 |
| cagggtgatg | aaccgatgat | ccctgcgaca | atcattcgtc | aggttgctga | taacctcgct 480 |
| cagcgtcagg | tgggtatgac | gactctggcg | gtgccaatcc | acaatgcgga | agaagcgttt 540 |
| aacccgaatg | cggtgaaagt | ggttctcgac | gctgaagggt | atgcactgta | cttctctcgc 600 |
| gccaccattc | cttgggatcg | tgatcgtttt | gcagaaggcc | ttaattcgat | gcttgttgcc 660 |
| aatcaagttg | tcacctgccc | agataaaaaa | tcgacagccg | cggtcattct | cacaccgacg 720 |
| gagaaccact | tcactctcaa | gtgccctaaa | acagcgctca | cagagcctcc | cactcttgcg 780 |
| tactcaccca | acaggcaaat | ctgcccagcg | ggtactacaa | gtagctgtac | atcaaaggct 840 |
| gtaacattga | gctccttgat | tcctgaagca | gaagatagct | ggtggacggg | ggattctgct 900 |
| agtctcgaca | cggcaggcat | caaactcaca | gttccaatcg | agaagttccc | cgtgacaacg 960 |
| cagacgtttg | tggtcggttg | catcaaggga | gacgacgcac | agagttgtat | ggtcacggtg 1020 |
| acagtacaag | ccagagcctc | atcggtcgtc | aataatgtcg | caaggtgctc | ctacggtgca 1080 |
| gacagcactc | ttggtcctgt | caagttgtct | gcggaaggac | ccactacaat | gaccctcgtg 1140 |
| tgcgggaaag | atggagtcaa | agttcctcaa | gacaacaatc | agtactgttc | cgggacgacg 1200 |
| ctgactggtt | gcaacgagaa | atcgttcaaa | gatattttgc | caaaattaac | tgagaacccg 1260 |
| tggcagggta | acgcttcgag | tgataagggt | gccacgctaa | cgatcaagaa | ggaagcatttt 1320 |
| ccagccgagt | caaaaagcgt | cattattgga | tgcacagggg | gatcgcctga | gaagcatcac 1380 |
| tgtaccgtga | aactggagtt | tgccgggct | gcagggtcag | caaaatcggc | tgcgggaaca 1440 |
| gccagtcacg | tttccattt | tgccatggtg | atcggactta | ttggctctat | cgcagcttgt 1500 |
| gtcgcgacgc | gtcttgaaac | cgttggcgat | aacttcctgc | gtcatcttgg | tatttatggc 1560 |
| taccgtgcag | gctttatccg | tcgttacgtc | aactggcagc | caagtccgtt | agaacacatc 1620 |
| gaaatgttag | agcagcttcg | tgttctgtgg | tacggcgaaa | aaatccatgt | tgctgttgct 1680 |
| caggaagttc | ctggcacagg | tgtggatacc | cctgaagatc | tcgacccgtc | gacgaattcg 1740 |
| agctcggtac | ccggggatcc | tctagactgc | aggcatgcta | agtaagtaga | tcttgagcgc 1800 |
| gttcgcgctg | aaatgcgcta | atttcacttc | acgacacttc | agccaatttt | gggaggagtg 1860 |
| tcgtaccgtt | acgattttcc | tcaatttttc | ttttcaacaa | ttgatctcat | tcaggtgaca 1920 |
| tcttttatat | tggcgctcat | tatgaaagca | gtagctttta | tgagggtaat | ctgaatggaa 1980 |
| cagctgcgtg | ccgaattaag | ccatttactg | ggcgaaaaac | tcagtcgtat | tgagtgcgtc 2040 |
| aatgaaaaag | cggatacggc | gttgtgggct | ttgtatgaca | gccagggaaa | cccaatgccg 2100 |
| ttaatggcaa | gaagcttagc | ccgcctaatg | agcgggcttt | tttttcgacg | cgaggctgga 2160 |
| tggccttccc | cattatgatt | cttctcgctt | ccggcggcat | cgggatgccc | gcgttgcagg 2220 |

-continued

```
ccatgctgtc caggcaggta gatgacgacc atcagggaca gcttcaagga tcgctcgcgg      2280
ctcttaccag cctaacttcg atcactggac cgctgatcgt cacggcgatt tatgccgcct      2340
cggcgagcac atgaacggg ttggcatgga ttgtaggcgc cgccctatac cttgtctgcc       2400
tccccgcgtt gcgtcgcggt gcatggagcc gggccacctc gacctgaatg gaagccggcg      2460
gcacctcgct aacggattca ccactccaag aattggagcc aatcaattct tgcggagaac      2520
tgtgaatgcg caaaccaacc cttggcagaa catatccatc gcgtccgcca tctccagcag      2580
ccgcacgcgg cgcatctcgg gcagcgttgg gtcctggcca cgggtgcgca tgatcgtgct      2640
cctgtcgttg aggacccggc taggctggcg gggttgcctt actggttagc agaatgaatc      2700
accgatacgc gagcgaacgt gaagcgactg ctgctgcaaa cgtctgcga cctgagcaac       2760 aacatgaatg gtcttcggtt ccgtgtttc gtaaagtctg gaaacgcgga agtcagcgcc       2820
ctgcaccatt atgttccgga tctgcatcgc aggatgctgc tggctaccct gtggaacacc      2880
tacatctgta ttaacgaagc gcttcttccg cttcctcgct cactgactcg ctgcgctcgg      2940
tcgttcggct gcggcgagcg gtatcagctc actcaaaggc ggtaatacgg ttatccacag      3000
aatcagggga taacgcagga agaacatgt gagcaaaagg ccagcaaaag gccaggaacc       3060
gtaaaaaggc cgcgttgctg gcgttttttcc ataggctccg ccccctgac gagcatcaca      3120 aaaatcgacg ctcaagtcag aggtggcgaa acccgacagg actataaaga taccaggcgt      3180
ttccccctgg aagctccctc gtgcgctctc ctgttccgac cctgccgctt accggatacc      3240
tgtccgcctt tctcccttcg ggaagcgtgg cgctttctca atgctcacgc tgtaggtatc      3300
tcagttcggt gtaggtcgtt cgctccaagc tgggctgtgt gcacgaaccc cccgttcagc      3360
ccgaccgctg cgccttatcc ggtaactatc gtcttgagtc caacccggta agacacgact      3420
tatcgccact ggcagcagcc actggtaaca ggattagcag agcgaggtat gtaggcggtg      3480
ctacagagtt cttgaagtgg tggcctaact acggctacac tagaaggaca gtatttggta      3540
tctgcgctct gctgaagcca gttaccttcg gaaaaagagt tggtagctct tgatccggca      3600
aacaaaccac cgctggtagc ggtggttttt tgtttgcaa gcagcagatt acgcgcagaa       3660
aaaaaggatc tcaagaagat cctttgatct tttctacggg gtctgacgct cagtggaacg      3720
aaaactcacg ttaagggatt ttggtcatga gattatcaaa aaggatcttc acctagatcc      3780
ttttaaatta aaaatgaagt tttaaatcaa tctaaagtat atatgagtaa acttggtctg      3840
acagttacca atgcttaatc agtgaggcac ctatctcagc gatctgtcta tttcgttcat      3900
ccatagttgc ctgactcccc gtcgtgtaga taactacgat acgggagggc ttaccatctg      3960
gccccagtgc tgcaatgata ccgcgagacc cacgctcacc ggctccagat ttatcagcaa      4020
taaaccagcc agccggaagg gccgagcgca gaagtggtcc tgcaacttta tccgcctcca      4080
tccagtctat taattgttgc cgggaagcta gagtaagtag ttcgccagtt aatagtttgc      4140
gcaacgttgt tgccattgct acaggcatcg tggtgtcacg ctcgtcgttt ggtatggctt      4200
cattcagctc cggttcccaa cgatcaaggc gagttacatg atccccccatg ttgtgcaaaa      4260 aagcggttag ctccttcggt cctccgatcg ttgtcagaag taagttggcc gcagtgttat      4320
cactcatggt tatggcagca ctgcataatt ctcttactgt catgccatcc gtaagatgct      4380
tttctgtgac tggtgagtac tcaaccaagt cattctgaga atagtgtatg cggcgaccga      4440
gttgctcttg cccggcgtca acacgggata ataccgcgcc acatagcaga actttaaaag      4500
tgctcatcat tggaaaacgt tcttcgggc gaaaactctc aaggatctta ccgctgttga      4560
gatccagttc gatgtaaccc actcgtgcac ccaactgatc ttcagcatct tttactttca      4620
```

```
ccagcgtttc tgggtgagca aaaacaggaa ggcaaaatgc cgcaaaaaag ggaataaggg      4680
cgacacggaa atgttgaata ctcatactct tccttttca atattattga agcatttatc      4740
agggttattg tctcatgagc ggatacatat ttgaatgtat ttagaaaaat aaacaaatag      4800
gggttccgcg cacatttccc cgaaaagtgc cacctgacgt ctaagaaacc attattatca      4860
tgacattaac ctataaaaat aggcgtatca cgaggccctt tcgtcttcaa                4910
```

<210> SEQ ID NO 41
<211> LENGTH: 40
<212> TYPE: DNA
<213> ORGANISM: Toxoplasma gondii

<400> SEQUENCE: 41

```
gagcagaagg ccttatgaac ggtcctttga gttatcatcc                           40
```

<210> SEQ ID NO 42
<211> LENGTH: 33
<212> TYPE: DNA
<213> ORGANISM: Toxoplasma gondii

<400> SEQUENCE: 42

```
ttcgctcacg cgtatggtga actgccggta tct                                  33
```

<210> SEQ ID NO 43
<211> LENGTH: 34
<212> TYPE: DNA
<213> ORGANISM: Toxoplasma gondii

<400> SEQUENCE: 43

```
gacggagacg cgtcttgaac cgttggcgat aact                                 34
```

<210> SEQ ID NO 44
<211> LENGTH: 21
<212> TYPE: DNA
<213> ORGANISM: Toxoplasma gondii

<400> SEQUENCE: 44

```
gcatgcctgc agtctagagg a                                               21
```

<210> SEQ ID NO 45
<211> LENGTH: 4451
<212> TYPE: DNA
<213> ORGANISM: Toxoplasma gondii

<400> SEQUENCE: 45

```
gaattaattc ccattaatgt gagttagctc actcattagg caccccaggc tttacacttt      60
atgttccggc tcgtattttg tgtggaattg tgagcggata caattgggc atccagtaag      120 gaggtttaaa tgagttttgt ggtcattatt cccgcgcgct acgcgtcgac gcgtctgccc      180
ggtaaaccat tggttgatat taacggcaaa cccatgattg ttcatgttct gaacgcgcg      240 cgtgaatcag gtgccgagcg catcatcgtg caaccgatc atgaggatgt tgcccgcgcc      300
gttgaagccg ctggcggtga agtatgtatg acgcgcgccg atcatcagtc aggaacagaa      360 cgtctggcg aagttgtcga aaaatgcgca ttcagcgacg acacggtgat cgttaatgtg      420
cagggtgatg aaccgatgat ccctgcgaca atcattcgtc aggttgctga taacctcgct      480
cagcgtcagg tgggtatgac gactctggcg gtgccaatcc acaatgcgga agaagcgttt      540
aacccgaatg cggtgaaagt ggttctcgac gctgaagggt atgcactgta cttctctcgc      600
```

-continued

| | |
|---|---|
| gccaccattc cttgggatcg tgatcgtttt gcagaaggcc ttatgaacgg tcctttgagt | 660 |
| tatcatccaa gcagttacgg agcgtcgtat ccgaatccga gtaatcctct gcatggaatg | 720 |
| cccaagccaa agaacccggt gagaccgcct cctcccggtt tccatccaag cgttattccc | 780 |
| aatcccccgt acccgctggg cactccagcg agcatgccac agccagaggt tccgccactt | 840 |
| cagcatcccc cgccaacggg ttcccctccc gcggccgctc cccagcctcc atatccagtg | 900 |
| ggtactccag taatgccaca gccagagata ccgcctgttc atcggccgcc gcctccgggt | 960 |
| ttccgtcccg aagtggctcc cgtgcccccg tatccagtgg gcactccaac gggcatgccc | 1020 |
| cagccggaga taccggcagt tcaccatacg cgtcttgaaa ccgttggcga taacttcctg | 1080 |
| cgtcatcttg gtatttatgg ctaccgtgca ggctttatcc gtcgttacgt caactggcag | 1140 |
| ccaagtccgt tagaacacat cgaaatgtta gagcagcttc gtgttctgtg gtacggcgaa | 1200 |
| aaaatccatg ttgctgttgc tcaggaagtt cctggcacag gtgtggatac ccctgaagat | 1260 |
| ctcgacccgt cgacgaattc gagctcggta cccggggatc ctctagactg caggcatgct | 1320 |
| aagtaagtag atcttgagcg cgttcgcgct gaaatgcgct aatttcactt cacgacactt | 1380 |
| cagccaattt tgggaggagt gtcgtaccgt tacgattttc ctcaattttt cttttcaaca | 1440 |
| attgatctca ttcaggtgac atctttata ttggcgctca ttatgaaagc agtagctttt | 1500 |
| atgagggtaa tctgaatgga acagctgcgt gccgaattaa gccatttact gggcgaaaaa | 1560 |
| ctcagtcgta ttgagtgcgt caatgaaaaa gcggatacgg cgttgtgggc tttgtatgac | 1620 |
| agccagggaa acccaatgcc gttaatggca agaagcttag cccgcctaat gagcgggctt | 1680 |
| ttttttcgac gcgaggctgg atggccttcc ccattatgat tcttctcgct tccggcggca | 1740 |
| tcgggatgcc cgcgttgcag gccatgctgt ccaggcaggt agatgacgac catcagggac | 1800 |
| agcttcaagg atcgctcgcg gctcttacca gcctaacttc gatcactgga ccgctgatcg | 1860 |
| tcacggcgat ttatgccgcc tcggcgagca catggaacgg gttggcatgg attgtaggcg | 1920 |
| ccgccctata ccttgtctgc ctccccgcgt tgcgtcgcgg tgcatggagc cgggccacct | 1980 |
| cgacctgaat ggaagccggc ggcacctcgc taacggattc accactccaa gaattggagc | 2040 |
| caatcaattc ttgcggagaa ctgtgaatgc gcaaaccaac ccttggcaga acatatccat | 2100 |
| cgcgtccgcc atctccagca gccgcacgcg gcgcatctcg gcagcgttg ggtcctggcc | 2160 |
| acgggtgcgc atgatcgtgc tcctgtcgtt gaggacccgg ctaggctggc ggggttgcct | 2220 |
| tactggttag cagaatgaat caccgatacg cgagcgaacg tgaagcgact gctgctgcaa | 2280 |
| aacgtctgcg acctgagcaa caacatgaat ggtcttcggt ttccgtgttt cgtaaagtct | 2340 |
| ggaaacgcgg aagtcagcgc cctgcaccat tatgttccgg atctgcatcg caggatgctg | 2400 |
| ctggctaccc tgtggaacac ctacatctgt attaacgaag cgcttcttcc gcttcctcgc | 2460 |
| tcactgactc gctgcgctcg tcgttcggc tgcggcgagc ggtatcagct cactcaaagg | 2520 |
| cggtaatacg gttatccaca gaatcagggg ataacgcagg aaagaacatg tgagcaaaag | 2580 |
| gccagcaaaa ggccaggaac cgtaaaaagg ccgcgttgct ggcgtttttc cataggctcc | 2640 |
| gcccccctga cgagcatcac aaaaatcgac gctcaagtca gaggtggcga aacccgacag | 2700 |
| gactataaag ataccaggcg tttccccctg gaagctccct cgtgcgctct cctgttccga | 2760 |
| ccctgccgct taccggatac ctgtccgcct ttctcccttc gggaagcgtg cgctttctc | 2820 |
| aatgctcacg ctgtaggtat ctcagttcgg tgtaggtcgt tcgctccaag ctgggctgtg | 2880 |
| tgcacgaacc ccccgttcag cccgaccgct gcgccttatc cggtaactat cgtcttgagt | 2940 |
| ccaacccggt aagacacgac ttatcgccac tggcagcagc cactggtaac aggattagca | 3000 |

-continued

```
gagcgaggta tgtaggcggt gctacagagt tcttgaagtg gtggcctaac tacggctaca    3060
ctagaaggac agtatttggt atctgcgctc tgctgaagcc agttaccttc ggaaaaagag    3120
ttggtagctc ttgatccggc aaacaaacca ccgctggtag cggtggtttt tttgtttgca    3180
agcagcagat tacgcgcaga aaaaaaggat ctcaagaaga tcctttgatc ttttctacgg    3240
ggtctgacgc tcagtggaac gaaaactcac gttaagggat tttggtcatg agattatcaa    3300
aaaggatctt cacctagatc cttttaaatt aaaaatgaag ttttaaatca atctaaagta    3360
tatatgagta aacttggtct gacagttacc aatgcttaat cagtgaggca cctatctcag    3420
cgatctgtct atttcgttca tccatagttg cctgactccc cgtcgtgtag ataactacga    3480
tacgggaggg cttaccatct ggccccagtg ctgcaatgat accgcgagac ccacgctcac    3540
cggctccaga tttatcagca ataaccagc cagccggaag ggccgagcgc agaagtggtc     3600
ctgcaacttt atccgcctcc atccagtcta ttaattgttg ccgggaagct agagtaagta    3660
gttcgccagt taatagtttg cgcaacgttg ttgccattgc tacaggcatc gtggtgtcac    3720
gctcgtcgtt tggtatggct tcattcagct ccggttccca acgatcaagg cgagttacat    3780
gatcccccat gttgtgcaaa aaagcggtta gctccttcgg tcctccgatc gttgtcagaa    3840
gtaagttggc cgcagtgtta tcactcatgg ttatggcagc actgcataat tctcttactg    3900
tcatgccatc cgtaagatgc ttttctgtga ctggtgagta ctcaaccaag tcattctgag    3960
aatagtgtat gcggcgaccg agttgctctt gcccggcgtc aacacgggat aataccgcgc    4020
cacatagcag aactttaaaa gtgctcatca ttggaaaacg ttcttcgggg cgaaaactct    4080
caaggatctt accgctgttg agatccagtt cgatgtaacc cactcgtgca cccaactgat    4140
cttcagcatc ttttactttc accagcgttt ctgggtgagc aaaaacagga aggcaaaatg    4200
ccgcaaaaaa gggaataagg gcgacacgga aatgttgaat actcatactc ttcctttttc    4260
aatattattg aagcatttat cagggttatt gtctcatgag cggatacata tttgaatgta    4320
tttagaaaaa taaacaaata ggggttccgc gcacatttcc ccgaaaagtg ccacctgacg    4380
tctaagaaac cattattatc atgacattaa cctataaaaa taggcgtatc acgaggccct    4440
ttcgtcttca a                                                        4451
```

<210> SEQ ID NO 46
<211> LENGTH: 41
<212> TYPE: DNA
<213> ORGANISM: Toxoplasma gondii

<400> SEQUENCE: 46

```
atattaggcc ttatgagcca caatggagtc cccgcttatc c                          41
```

<210> SEQ ID NO 47
<211> LENGTH: 38
<212> TYPE: DNA
<213> ORGANISM: Toxoplasma gondii

<400> SEQUENCE: 47

```
cagtgtacgc gtttgcgatc catcatcctg ctctcttc                              38
```

<210> SEQ ID NO 48
<211> LENGTH: 5258
<212> TYPE: DNA
<213> ORGANISM: Toxoplasma gondii

<400> SEQUENCE: 48

-continued

```
gaattaattc ccattaatgt gagttagctc actcattagg cacccaggc tttacacttt      60 atgttccggc tcgtattttg tgtggaattg tgagcggata caattgggc atccagtaag     120 gaggtttaaa tgagttttgt ggtcattatt cccgcgcgct acgcgacgtc gcgtctgccc     180
ggtaaaccat tggttgatat taacggcaaa cccatgattg ttcatgttct gaacgcgcg     240 cgtgaatcag gtgccgagcg catcatcgtg gcaaccgatc atgaggatgt tgcccgcgcc    300
gttgaagccg ctggcggtga agtatgtatg acgcgcgccg atcatcagtc aggaacagaa    360
cgtctggcgg aagttgtcga aaaatgcgca ttcagcgacg acacggtgat cgttaatgtg    420
cagggtgatg aaccgatgat ccctgcgaca atcattcgtc aggttgctga taacctcgct    480
cagcgtcagg tgggtatgac gactctggcg gtgccaatcc acaatgcgga agaagcgttt    540
aacccgaatg cggtgaaagt ggttctcgac gctgaagggt atgcactgta cttctctcgc    600
gccaccattc cttgggatcg tgatcgtttt gcagaaggcc ttatgagcca caatggagtc    660
cccgcttatc catcgtatgc acaggtatcg ctctcttcca acggcgagcc acggcacagg    720
ggcatacgcg gcagcttcct catgtccgta agccacacg caaacgctga tgacttcgcc    780
tccgacgaca actacgaacc gctgccgagt ttcgtggaag ctcctgtcag aggcccggac    840
caagtccctg ccagaggaga agctgctctt gtcacagagg agactccagc gcaacagccg    900
gcggtggctc taggcagtgc agaaggggag gggacctcca ctactgaatc cgcctccgaa    960
aattctgaag atgatgacac gtttcacgat gccctccaag agcttccaga ggatggcctc   1020
gaagtgcgcc accaaatgc acaggagctg cccccaccaa atgtacagga gctgcccccca  1080 ccaaatgtac aggagctgcc cccaccaact gaacaggagc tgcccccacc aactgaacag   1140
gagctgcccc caccaactga acaggagctg cccccaccaa ctgaacagga gctaccccca   1200
tcaactgaac aggagctgcc cccaccagtg ggcgaaggtc aacgtctgca agtccctggg   1260
gaacatgggc cacaggggcc cccatacgat gatcagcagc tgcttttaga gcctacggaa   1320
gagcaacagg agggccctca ggagccgctg ccaccgccgc cgcccccgac tcggggcgaa   1380
caacccgaag acagcagcc gcagggacca gttcgtcaaa atttttttcg tcgggcgttg   1440
ggggccgcaa gaagccgatt cggaggtgca cgacgccatg tcagtggggt gttccgaaga   1500
gtcagaggtg gtttgaaccg tatagtaggt ggagtgagga gtggtttcag gcgtgcaaga   1560
gaaggtgtcg ttgggggagt ccgtcgttta caagtggtg ccagtctggg tctccgtcgt    1620
gtaggagaag gtttacgtag gagtttctat cgtgtaagag gagctgtcag tagcggtcgt   1680
aggcgtgcag cagatggtgc cagcaatgta agagaaagat tcgttgccgc aggcgggaga   1740
gtcagagacg ctttcggcgc gggattgacg cgcctccgca ggcgcggcag aactaatggc   1800
gaggagggca ggcccctact gggcgaagga agagagcagg atgatggatc gcaaacgcgt   1860
cttgaaaccg ttggcgataa cttcctgcgt catcttggta tttatggcta ccgtgcaggc   1920
tttatccgtc gttacgtcaa ctggcagcca agtccgttag aacacatcga aatgttagag   1980
cagcttcgtg ttctgtggta cggcgaaaaa atccatgttg ctgttgctca ggaagttcct   2040
ggcacaggtg tggatacccc tgaagatctc gacccgtcga cgaattcgag ctcggtaccc   2100
ggggatcctc tagactgcag gcatgctaag taagtagatc ttgagcgcgt tcgcgctgaa   2160
atgcgctaat ttcacttcac gacacttcag ccaattttgg gaggagtgtc gtaccgttac   2220
gattttcctc aattttctct ttcaacaatt gatctcattc aggtgacatc ttttatattg   2280
gcgctcatta tgaaagcagt agcttttatg agggtaatct gaatggaaca gctgcgtgcc   2340
gaattaagcc atttactggg cgaaaaactc agtcgtattg agtgcgtcaa tgaaaaagcg   2400
```

-continued

```
gatacggcgt tgtgggcttt gtatgacagc cagggaaacc caatgccgtt aatggcaaga      2460
agcttagccc gcctaatgag cgggcttttt tttcgacgcg aggctggatg gccttcccca      2520
ttatgattct tctcgcttcc ggcggcatcg ggatgcccgc gttgcaggcc atgctgtcca      2580
ggcaggtaga tgacgaccat cagggacagc ttcaaggatc gctcgcggct cttaccagcc      2640
taacttcgat cactggaccg ctgatcgtca cggcgattta tgccgcctcg gcgagcacat      2700
ggaacgggtt ggcatggatt gtaggcgccg ccctatacct tgtctgcctc cccgcgttgc      2760
gtcgcggtgc atggagccgg ccacctcga cctgaatgga agccggcggc acctcgctaa       2820
cggattcacc actccaagaa ttggagccaa tcaattcttg cggagaactg tgaatgcgca      2880
aaccaaccct tggcagaaca tatccatcgc gtccgccatc tccagcagcc gcacgcggcg      2940
catctcgggc agcgttgggt cctggccacg ggtgcgcatg atcgtgctcc tgtcgttgag      3000
gacccggcta ggctggcggg gttgccttac tggttagcag aatgaatcac cgatacgcga      3060
gcgaacgtga agcgactgct gctgcaaaac gtctgcgacc tgagcaacaa catgaatggt      3120
cttcggtttc cgtgtttcgt aaagtctgga aacgcggaag tcagcgccct gcaccattat      3180
gttccggatc tgcatcgcag gatgctgctg ctaccctgt ggaacaccta catctgtatt       3240
aacgaagcgc ttcttccgct tcctcgctca ctgactcgct gcgctcggtc gttcggctgc      3300
ggcgagcggt atcagctcac tcaaaggcgg taatacggtt atccacagaa tcagggata      3360 acgcaggaaa gaacatgtga gcaaaaggcc agcaaaaggc caggaaccgt aaaaaggccg      3420
cgttgctggc gttttccat aggctccgcc ccctgacga gcatcacaaa aatcgacgct        3480
caagtcagag gtggcgaaac ccgacaggac tataaagata ccaggcgttt ccccctggaa      3540
gctccctcgt gcgctctcct gttccgaccc tgccgcttac cggatacctg tccgcctttc      3600
tcccttcggg aagcgtggcg ctttctcaat gctcacgctg taggtatctc agttcggtgt      3660
aggtcgttcg ctccaagctg ggctgtgtgc acgaaccccc cgttcagccc gaccgctgcg      3720
ccttatccgg taactatcgt cttgagtcca acccggtaag acacgactta tcgccactgg      3780
cagcagccac tggtaacagg attagcagag cgaggtatgt aggcggtgct acagagttct      3840
tgaagtggtg gcctaactac ggctacacta aaggacagt atttggtatc tgcgctctgc       3900
tgaagccagt taccttcgga aaaagagttg gtagctcttg atccggcaaa caaaccaccg      3960
ctggtagcgg tggttttttt gtttgcaagc agcagattac gcgcagaaaa aaaggatctc      4020
aagaagatcc tttgatcttt tctacggggt ctgacgctca gtggaacgaa aactcacgtt      4080
aagggatttt ggtcatgaga ttatcaaaaa ggatcttcac ctagatcctt ttaaattaaa      4140
aatgaagttt taaatcaatc taaagtatat atgagtaaac ttggtctgac agttaccaat      4200
gcttaatcag tgaggcacct atctcagcga tctgtctatt tcgttcatcc atagttgcct      4260
gactccccgt cgtgtagata actacgatac gggagggctt accatctggc cccagtgctg      4320
caatgatacc gcgagaccca cgctcaccgg ctccagattt atcagcaata accagccag      4380 ccggaagggc cgagcgcaga agtggtcctg caactttatc cgcctccatc cagtctatta     4440
attgttgccg ggaagctaga gtaagtagtt cgccagttaa tagtttgcgc aacgttgttg      4500
ccattgctac aggcatcgtg gtgtcacgct cgtcgtttgg tatggcttca ttcagctccg      4560
gttcccaacg atcaaggcga gttacatgat cccccatgtt gtgcaaaaaa gcggttagct      4620
ccttcggtcc tccgatcgtt gtcagaagta agttggccgc agtgttatca ctcatggtta      4680
tggcagcact gcataattct cttactgtca tgccatccgt aagatgcttt tctgtgactg      4740
```

-continued

```
gtgagtactc aaccaagtca ttctgagaat agtgtatgcg gcgaccgagt tgctcttgcc    4800
cggcgtcaac acgggataat accgcgccac atagcagaac tttaaaagtg ctcatcattg    4860
gaaaacgttc ttcggggcga aaactctcaa ggatcttacc gctgttgaga tccagttcga    4920
tgtaacccac tcgtgcaccc aactgatctt cagcatcttt tactttcacc agcgtttctg    4980
ggtgagcaaa aacaggaagg caaaatgccg caaaaaggg aataagggcg acacggaaat     5040
gttgaatact catactcttc cttttcaat attattgaag catttatcag ggttattgtc     5100
tcatgagcgg atacatattt gaatgtattt agaaaaataa acaaataggg gttccgcgca    5160
catttccccg aaaagtgcca cctgacgtct aagaaaccat tattatcatg acattaacct    5220
ataaaaatag gcgtatcacg aggccctttc gtcttcaa                            5258
```

<210> SEQ ID NO 49
<211> LENGTH: 22
<212> TYPE: PRT
<213> ORGANISM: Toxoplasma gondii

<400> SEQUENCE: 49

Asp Leu Asp Pro Ser Thr Asn Ser Ser Val Pro Gly Asp Pro Leu
1               5                   10                  15

Asp Cys Arg His Ala Lys
            20

<210> SEQ ID NO 50
<211> LENGTH: 22
<212> TYPE: PRT
<213> ORGANISM: Toxoplasma gondii

<400> SEQUENCE: 50

Asp Leu Asp Pro Ser Thr Asn Ser Ser Val Pro Gly Asp Pro Leu
1               5                   10                  15

Asp Cys Arg His Ala Lys
            20

<210> SEQ ID NO 51
<211> LENGTH: 13
<212> TYPE: PRT
<213> ORGANISM: Toxoplasma gondii

<400> SEQUENCE: 51

Gly Leu Asn Ser Ser Ser Gly Ile Arg Leu Gln Thr Arg
1               5                   10

<210> SEQ ID NO 52
<211> LENGTH: 506
<212> TYPE: PRT
<213> ORGANISM: Toxoplasma gondii

<400> SEQUENCE: 52

Met Ser Phe Val Val Ile Ile Pro Ala Arg Tyr Ala Thr Ser Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

```
Glu Val Val Glu Lys Cys Ala Phe Ser Asp Asp Thr Val Ile Val Asn
                 85                  90                  95
Val Gln Gly Asp Glu Pro Met Ile Pro Ala Thr Ile Ile Arg Gln Val
            100                 105                 110
Ala Asp Asn Leu Ala Gln Arg Gln Val Gly Met Thr Thr Leu Ala Val
        115                 120                 125
Pro Ile His Asn Ala Glu Glu Ala Phe Asn Pro Asn Ala Val Lys Val
    130                 135                 140
Val Leu Asp Ala Glu Gly Tyr Ala Leu Tyr Phe Ser Arg Ala Thr Ile
145                 150                 155                 160
Pro Trp Asp Arg Asp Arg Phe Ala Glu Gly Leu Asn Ser Met Ala Arg
                165                 170                 175
His Ala Ile Phe Ser Ala Leu Cys Val Leu Gly Leu Val Ala Ala Ala
            180                 185                 190
Leu Pro Gln Phe Ala Thr Ala Ala Thr Ala Ser Asp Asp Glu Leu Met
        195                 200                 205
Ser Arg Ile Arg Asn Ser Asp Phe Phe Asp Gly Gln Ala Pro Val Asp
    210                 215                 220
Ser Leu Arg Pro Thr Asn Ala Gly Val Asp Ser Lys Gly Thr Asp Asp
225                 230                 235                 240
His Leu Thr Thr Ser Met Asp Lys Ala Ser Val Glu Ser Gln Leu Pro
                245                 250                 255
Arg Arg Glu Pro Leu Glu Thr Glu Pro Asp Glu Gln Glu Glu Val His
            260                 265                 270
Phe Arg Lys Arg Gly Val Arg Ser Asp Ala Glu Val Thr Asp Asp Asn
        275                 280                 285
Ile Tyr Glu Glu His Thr Asp Arg Lys Val Val Pro Arg Lys Ser Glu
    290                 295                 300
Gly Lys Arg Ser Phe Lys Asp Leu Leu Lys Leu Ala Leu Pro Ala
305                 310                 315                 320
Val Gly Met Gly Ala Ser Tyr Phe Ala Ala Asp Arg Leu Val Pro Glu
                325                 330                 335
Leu Thr Glu Glu Gln Gln Arg Gly Asp Glu Pro Leu Thr Thr Gly Gln
            340                 345                 350
Asn Val Gly Thr Val Leu Gly Phe Ala Ala Leu Ala Ala Ala Ala Ala
        355                 360                 365
Phe Leu Gly Met Gly Leu Thr Arg Thr Tyr Arg His Phe Ser Pro Arg
    370                 375                 380
Lys Asn Arg Ser Arg Gln Pro Ala Leu Glu Gln Glu Val Pro Glu Ser
385                 390                 395                 400
Gly Glu Asp Gly Glu Asp Ala Arg Gln Arg Ile Arg Leu Gln Thr Arg
                405                 410                 415
Leu Glu Thr Val Gly Asp Asn Phe Leu Arg His Leu Gly Ile Tyr Gly
            420                 425                 430
Tyr Arg Ala Gly Phe Ile Arg Arg Tyr Val Asn Trp Gln Pro Ser Pro
        435                 440                 445
Leu Glu His Ile Glu Met Leu Glu Gln Leu Arg Val Leu Trp Tyr Gly
    450                 455                 460
Glu Lys Ile His Val Ala Val Ala Gln Glu Val Pro Gly Thr Gly Val
465                 470                 475                 480
Asp Thr Pro Glu Asp Leu Asp Pro Ser Thr Asn Ser Ser Ser Val Pro
                485                 490                 495
```

```
Gly Asp Pro Leu Asp Cys Arg His Ala Lys
            500                 505

<210> SEQ ID NO 53
<211> LENGTH: 551
<212> TYPE: PRT
<213> ORGANISM: Toxoplasma gondii

<400> SEQUENCE: 53

Met Ser Phe Val Val Ile Ile Pro Ala Arg Tyr Ala Thr Ser Arg Leu
 1               5                  10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Asn Ser Met Leu Val
                165                 170                 175

Ala Asn Gln Val Val Thr Cys Pro Asp Lys Lys Ser Thr Ala Ala Val
            180                 185                 190

Ile Leu Thr Pro Thr Glu Asn His Phe Thr Leu Lys Cys Pro Lys Thr
        195                 200                 205

Ala Leu Thr Glu Pro Pro Thr Leu Ala Tyr Ser Pro Asn Arg Gln Ile
    210                 215                 220

Cys Pro Ala Gly Thr Thr Ser Ser Cys Thr Ser Lys Ala Val Thr Leu
225                 230                 235                 240

Ser Ser Leu Ile Pro Glu Ala Glu Asp Ser Trp Trp Thr Gly Asp Ser
                245                 250                 255

Ala Ser Leu Asp Thr Ala Gly Ile Lys Leu Thr Val Pro Ile Glu Lys
            260                 265                 270

Phe Pro Val Thr Thr Gln Thr Phe Val Val Gly Cys Ile Lys Gly Asp
        275                 280                 285

Asp Ala Gln Ser Cys Met Val Thr Val Gln Ala Arg Ala Ser
    290                 295                 300

Ser Val Val Asn Asn Val Ala Arg Cys Ser Tyr Gly Ala Asp Ser Thr
305                 310                 315                 320

Leu Gly Pro Val Lys Leu Ser Ala Glu Gly Pro Thr Thr Met Thr Leu
                325                 330                 335

Val Cys Gly Lys Asp Gly Val Lys Val Pro Gln Asp Asn Asn Gln Tyr
            340                 345                 350

Cys Ser Gly Thr Thr Leu Thr Gly Cys Asn Glu Lys Ser Phe Lys Asp
        355                 360                 365
```

Ile Leu Pro Lys Leu Thr Glu Asn Pro Trp Gln Gly Asn Ala Ser Ser
        370                 375                 380

Asp Lys Gly Ala Thr Leu Thr Ile Lys Lys Glu Ala Phe Pro Ala Glu
385                 390                 395                 400

Ser Lys Ser Val Ile Ile Gly Cys Thr Gly Ser Pro Glu Lys His
                405                 410                 415

His Cys Thr Val Lys Leu Glu Phe Ala Gly Ala Ala Gly Ser Ala Lys
                420                 425                 430

Ser Ala Ala Gly Thr Ala Ser His Val Ser Ile Phe Ala Met Val Ile
            435                 440                 445

Gly Leu Ile Gly Ser Ile Ala Ala Cys Val Ala Thr Arg Leu Glu Thr
        450                 455                 460

Val Gly Asp Asn Phe Leu Arg His Leu Gly Ile Tyr Gly Tyr Arg Ala
465                 470                 475                 480

Gly Phe Ile Arg Arg Tyr Val Asn Trp Gln Pro Ser Pro Leu Glu His
                485                 490                 495

Ile Glu Met Leu Glu Gln Leu Arg Val Leu Trp Tyr Gly Glu Lys Ile
                500                 505                 510

His Val Ala Val Ala Gln Glu Val Pro Gly Thr Gly Val Asp Thr Pro
            515                 520                 525

Glu Asp Leu Asp Pro Ser Thr Asn Ser Ser Val Pro Gly Asp Pro
        530                 535                 540

Leu Asp Cys Arg His Ala Lys
545                 550

<210> SEQ ID NO 54
<211> LENGTH: 398
<212> TYPE: PRT
<213> ORGANISM: Toxoplasma gondii

<400> SEQUENCE: 54

Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
        130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Met Asn Gly Pro Leu
                165                 170                 175

Ser Tyr His Pro Ser Ser Tyr Gly Ala Ser Tyr Pro Asn Pro Ser Asn

```
                    180                 185                 190
Pro Leu His Gly Met Pro Lys Pro Glu Asn Pro Val Arg Pro Pro
            195                 200                 205

Pro Gly Phe His Pro Ser Val Ile Pro Asn Pro Tyr Pro Leu Gly
            210                 215                 220

Thr Pro Ala Ser Met Pro Gln Pro Glu Val Pro Pro Leu Gln His Pro
225                 230                 235                 240

Pro Pro Thr Gly Ser Pro Ala Ala Ala Pro Gln Pro Pro Tyr Pro
                245                 250                 255

Val Gly Thr Pro Val Met Pro Gln Pro Glu Ile Pro Pro Val His Arg
                260                 265                 270

Pro Pro Pro Gly Phe Arg Pro Glu Val Ala Pro Val Pro Pro Tyr
            275                 280                 285

Pro Val Gly Thr Pro Thr Gly Met Pro Gln Pro Glu Ile Pro Ala Val
            290                 295                 300

His His Thr Arg Leu Glu Thr Val Gly Asp Asn Phe Leu Arg His Leu
305                 310                 315                 320

Gly Ile Tyr Gly Tyr Arg Ala Gly Phe Ile Arg Arg Tyr Val Asn Trp
                325                 330                 335

Gln Pro Ser Pro Leu Glu His Ile Glu Met Leu Glu Gln Leu Arg Val
                340                 345                 350

Leu Trp Tyr Gly Glu Lys Ile His Val Ala Val Ala Gln Glu Val Pro
                355                 360                 365

Gly Thr Gly Val Asp Thr Pro Glu Asp Leu Asp Pro Ser Thr Asn Ser
            370                 375                 380

Ser Ser Val Pro Gly Asp Pro Leu Asp Cys Arg His Ala Lys
385                 390                 395

<210> SEQ ID NO 55
<211> LENGTH: 667
<212> TYPE: PRT
<213> ORGANISM: Toxoplasma gondii

<400> SEQUENCE: 55

Met Ser Phe Val Val Ile Ile Pro Ala Arg Tyr Ala Thr Ser Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
            115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160
```

-continued

```
Pro Trp Asp Arg Asp Arg Phe Ala Glu Gly Leu Met Ser His Asn Gly
            165                 170                 175

Val Pro Ala Tyr Pro Ser Tyr Ala Gln Val Ser Leu Ser Ser Asn Gly
            180                 185                 190

Glu Pro Arg His Arg Gly Ile Arg Gly Ser Phe Leu Met Ser Val Lys
            195                 200                 205

Pro His Ala Asn Ala Asp Asp Phe Ala Ser Asp Asn Tyr Glu Pro
        210                 215                 220

Leu Pro Ser Phe Val Glu Ala Pro Val Arg Gly Pro Asp Gln Val Pro
225                 230                 235                 240

Ala Arg Gly Glu Ala Ala Leu Val Thr Glu Thr Pro Ala Gln Gln
            245                 250                 255

Pro Ala Val Ala Leu Gly Ser Ala Glu Gly Glu Gly Thr Ser Thr Thr
            260                 265                 270

Glu Ser Ala Ser Glu Asn Ser Glu Asp Asp Asp Thr Phe His Asp Ala
        275                 280                 285

Leu Gln Glu Leu Pro Glu Asp Gly Leu Glu Val Arg Pro Pro Asn Ala
    290                 295                 300

Gln Glu Leu Pro Pro Asn Val Gln Glu Leu Pro Pro Asn Val
305                 310                 315                 320

Gln Glu Leu Pro Pro Thr Glu Gln Glu Leu Pro Pro Thr Glu
            325                 330                 335

Gln Glu Leu Pro Pro Thr Glu Gln Glu Leu Pro Pro Thr Glu
            340                 345                 350

Gln Glu Leu Pro Pro Ser Thr Glu Gln Glu Leu Pro Pro Val Gly
            355                 360                 365

Glu Gly Gln Arg Leu Gln Val Pro Gly Glu His Gly Pro Gln Gly Pro
    370                 375                 380

Pro Tyr Asp Asp Gln Gln Leu Leu Leu Glu Pro Thr Glu Glu Gln Gln
385                 390                 395                 400

Glu Gly Pro Gln Glu Pro Leu Pro Pro Pro Pro Thr Arg Gly
            405                 410                 415

Glu Gln Pro Glu Gly Gln Gln Pro Gln Gly Pro Val Arg Gln Asn Phe
            420                 425                 430

Phe Arg Arg Ala Leu Gly Ala Ala Arg Ser Arg Phe Gly Gly Ala Arg
            435                 440                 445

Arg His Val Ser Gly Val Phe Arg Arg Val Arg Gly Gly Leu Asn Arg
    450                 455                 460

Ile Val Gly Gly Val Arg Ser Gly Phe Arg Arg Ala Arg Glu Gly Val
465                 470                 475                 480

Val Gly Gly Val Arg Arg Leu Thr Ser Gly Ala Ser Leu Gly Leu Arg
            485                 490                 495

Arg Val Gly Glu Gly Leu Arg Arg Ser Phe Tyr Arg Val Arg Gly Ala
        500                 505                 510

Val Ser Ser Gly Arg Arg Ala Ala Asp Gly Ala Ser Asn Val Arg
    515                 520                 525

Glu Arg Phe Val Ala Ala Gly Gly Arg Val Arg Asp Ala Phe Gly Ala
530                 535                 540

Gly Leu Thr Arg Leu Arg Arg Gly Arg Thr Asn Gly Glu Glu Gly
545                 550                 555                 560

Arg Pro Leu Leu Gly Glu Gly Arg Glu Gln Asp Asp Gly Ser Gln Thr
            565                 570                 575

Arg Leu Glu Thr Val Gly Asp Asn Phe Leu Arg His Leu Gly Ile Tyr
```

-continued

```
                580                 585                 590
Gly Tyr Arg Ala Gly Phe Ile Arg Arg Tyr Val Asn Trp Gln Pro Ser
            595                 600                 605
Pro Leu Glu His Ile Glu Met Leu Glu Gln Leu Arg Val Leu Trp Tyr
        610                 615                 620
Gly Glu Lys Ile His Val Ala Val Ala Gln Glu Val Pro Gly Thr Gly
625                 630                 635                 640
Val Asp Thr Pro Glu Asp Leu Asp Pro Ser Thr Asn Ser Ser Ser Val
                645                 650                 655
Pro Gly Asp Pro Leu Asp Cys Arg His Ala Lys
                660                 665
```

ANTIGEN COCKTAILS AND USES THEREOF

BACKGROUND OF THE INVENTION

1. Technical Field

The present invention relates to combinations or mixtures of antigens which may be used in the detection of IgM or IgG antibodies to *Toxoplasma gondii*. Furthermore, the present invention also relates to methods of using these combinations of antigens, antibodies raised against these combinations of antigens or against the novel P29 antigen thereof, as well as kits and vaccine containing the antigens present in the combinations.

2. Background Information

*Toxoplasma gondii* is an obligate intracellular parasite which is classified among the Coccidia. This parasite has relatively broad host range infecting both mammals and birds. The organism is ubiquitous in nature and exists in three forms: tachyzoite, cyst, and oocyst (Remington, J. S., McLeod, R., Desmonds, G., Infectious Diseases of the Fetus and Newborn Infant (J. S. Remington and J. O. Klein, Eds.), pp. 140–267, Saunders, Philadelphia (1995)). Tachyzoites, found during acute infection, are the invasive form capable of invading all nucleated mammalian cells. After the acute stage of infection, tissue cysts called bradyzoites are formed within host cells and persist within the host organism for the life of the host. Cysts are important in transmission of infection, especially in humans, as the ingestion of raw or undercooked meat can result in the ingestion of bradyzoites which can infect the individual resulting in an acute infection. Oocysts represent a stage of sexual reproduction which occurs only in the intestinal lining of the cat family from which they are excreted in the feces.

A *T. gondii* infection acquired through contaminated meat or cat feces in a healthy adult is often asymptomatic. In pregnant women and immunosuppressed patients, the clinical outcome can be very serious. An acute infection with *T. gondii* acquired during pregnancy, especially during the first trimester, can result in intrauterine transmission to the unborn fetus resulting in severe fetal and neonatal complications, including mental retardation and fetal death. Recrudesence of a previous *T. gondii* infection or an acute infection in an immunosuppressed individual can be pathogenic. Toxoplasmic encephalitis is a major cause of morbidity and mortality in AIDS patients. Toxoplasma infection has also been shown to be a significant cause of chorioretinitis in children and adults.

Diagnosis of infection with *T. gondii* may be established by the isolation of *T. gondii* from blood or body fluids, demonstration of the presence of the organism in the placenta or tissues of the fetus, demonstration of the presence of antigen by detection of specific nucleic acid sequences (e.g., DNA probes), or detection of *T. gondii* specific immunoglobulins synthesized by the host in response to infection using serologic tests.

The detection of *T. gondii* specific antibodies and determination of antibody titer are important tools used in the diagnosis of toxoplasmosis. The most widely used serologic tests for the diagnosis of toxoplasmosis are the Sabin-Feldman dye test (Sabin, A. B. and Feldman, H. A. (1948) Science 108, 660–663), the indirect hemagglutination (IHA) test (Jacobs, L. and Lunde, M. (1957) J. Parasitol. 43, 308–314), the IFA test (Walton, B. C. et al. (1966) Am. J. Trop. Med. Hyg. 15, 149–152), the agglutination test (Fondation Mérieux, Sérologie de l' Infection Toxoplasmique en Particulier à Son Début: Méthodes et Interpréta-tion des Résultats, Lyon, 182 pp. (1975)) and the ELISA (Naot, Y. and Remington, J. S. (1980) J. Infect. Dis. 142, 757–766). The ELISA test is one the easiest tests to perform, and many automated serologic tests for the detection of Toxoplasma specific IgM and IgG are commercially available.

The current tests for the detection of IgM and IgG antibodies in infected individuals can vary widely in their ability to detect serum antibody. Hence, there is significant inter-assay variation seen among the commercially available kits. The differences observed between the different commercial kits are caused primarily by the preparation of the antigen used for the serologic test. Most kits use either whole or sonicated tachyzoites grown in tissue culture or in mice which contain a high proportion of extra-parasitic material, for example, mammalian cells, tissue culture components, etc. Due to the lack of a purified, standardized antigen or standard method for preparing the tachyzoite antigen, it is not surprising that inter-assay variability exists resulting in different assays having different performance characteristics in terms of assay sensitivity and specificity.

Given the limitations of serologic tests employing the tachyzoite antigen, purified recombinant antigens obtained by molecular biology are an attractive alternative in that they can be purified and standardized. In the literature, a number of Toxo genes have been cloned and expressed in a suitable host to produce immunoreactive, recombinant Toxo antigens. For example, the Toxo P22 (SAG2), P24 (GRA1), P25, P28 (GRA2), P30 (SAG1), P35, P41 (GRA4), P54 (ROP2), P66 (ROP1), and the Toxo P68 antigens have been described (Prince et al. (1990) Mol. Biochem. Parasitol 43, 97–106; Cesbron-Delauw et al. (1989) Proc. Nat. Acad. Sci. 86, 7537–7541; Johnson et al. (1991) Gene 99, 127–132; Prince et al. (1989) Mol. Biochem. Parasitol. 34, 3–13; Burg et al. (1988) J. Immunol. 141, 3584–3591; Knapp et al. (1989) EPA 431541A2; Mevelec et al. (1992) Mol. Biochem. Parasitol. 56, 227–238; Saavedra et al. (1991) J. Immunol. 147, 1975–1982).

It is plausible that no single Toxo antigen can replace the tachyzoite in an immunoassay for the detection of Toxo-specific immunoglobulins. This may be for several reasons. First, the antibodies produced during infection vary with the stage of infection, i.e., the antibodies produced by an infected individual vary over time reacting with different epitopes. Secondly, the epitopes present in a recombinant antigen may be different or less reactive than native antigen prepared from the tachyzoite depending on the host used for expression and the purification scheme employed. Thirdly, different recombinant antigens may be needed to detect the different classes of immunoglobulins produced in response to an infection, e.g., IgM, IgG, IgA, IgE.

In order to overcome the limitations of the tachyzoite antigen in terms of assay specificity and sensitivity, a search was begun for novel Toxo antigens which could be used in combination with known existing antigens in order to configure new assays for the detection of Toxo-specific immunoglobulins.

SUMMARY OF THE INVENTION

The present invention includes a composition comprising *Toxoplasma gondii* antigens P29, P30 and P35 as well as a composition comprising *Toxoplasma gondii* antigens P29, P35 and 66. These compositions may be used as diagnositic reagents, and the antigens within these compositions may be produced either recombinantly or synthetically.

Additionally, the present invention includes an isolated nucleic acid sequence represented by SEQ ID NO: 26 and a purified polypeptide having the amino acid sequence represented by SEQ ID NO: 27. The present invention also includes a polyclonal or monoclonal antibody directed against the purified polypeptide.

The present invention also encompasses a method for detecting the presence of IgM antibodies to *Toxoplasma gondii* in a test sample. This method comprises the steps of: a) contacting the test sample suspected of containing the IgM antibodies with a composition comprising P29, P35 and P66; and b) detecting the presence of the IgM antibodies.

Furthermore, the present invention includes an additional method for detecting the presence of IgM antibodies to *Toxoplasma gondii* in a test sample. This method comprises the steps of: a) contacting the test sample suspected of containing the IgM antibodies with a composition comprising antigen P29, P35 and P66 for a time and under conditions sufficient for the formation of IgM antibody/antigen complexes; b) adding a conjugate to the resulting IgM antibody/antigen complexes for a time and under conditions sufficient to allow the conjugate to bind to the bound antibody, wherein the conjugate comprises an antibody attached to a signal generating compound capable of generating a detectable signal; and c) detecting the presence of IgM antibodies which may be present in the test sample by detecting a signal generated by the signal generating compound.

Moreover, the present invention also includes a method for detecting the presence of IgG antibodies to *Toxoplasma gondii* in a test sample. This method comprises the steps of: a) contacting the test sample suspected of containing the IgG antibodies with a composition comprising P29, P30 and P35; and b) detecting the presence of the IgG antibodies.

Additionally, the present invention encompasses another method for detecting the presence of IgG antibodies to *Toxoplasma gondii* in a test sample. This method comprising the steps of: a) contacting said test sample suspected of containing the IgG antibodies with a composition comprising antigen P29, P30 and P35 for a time and under conditions sufficient for formation of IgG antibody/antigen complexes; b) adding a conjugate to resulting IgG antibody/antigen complexes for a time and under conditions sufficient to allow the conjugate to bind to bound antibody, wherein the conjugate comprises an antibody attached to a signal generating compound capable of generating a detectable signal; and c) detecting IgG antibodies which may be present in said test sample by detecting a signal generated by said signal generating compound.

Additionally, the present invention includes another method for detecting the presence of IgM antibodies to *Toxoplasma gondii* in a test sample. This method comprises the steps of: a) contacting the test sample suspected of containing the IgM antibodies with anti-antibody specific for the IgM antibodies for a time and under conditions sufficient to allow for formation of anti-antibody/IgM antibody complexes; b) adding a conjugate to resulting anti-antibody/IgM antibody complexes for a time and under conditions sufficient to allow the conjugate to bind to bound antibody, wherein the conjugate comprises P29, P35 and P66, each attached to a signal generating compound capable of generating a detectable signal; and c) detecting IgM antibodies which may be present in the test sample by detecting a signal generated by the signal generating compound.

Another method for detecting the presence of IgG antibodies to *Toxoplasma gondii* in a test sample, encompassed by the present invention, comprises the steps of: a) contacting the test sample suspected of containing the IgG antibodies with anti-antibody specific for the IgG antibodies for a time and under conditions sufficient to allow for formation of anti-antibody/IgG antibody complexes; b) adding a conjugate to resulting anti-antibody/IgG antibody complexes for a time and under conditions sufficient to allow the conjugate to bind to bound antibody, wherein the conjugate comprises P29, P30 and P35, each attached to a signal generating compound capable of generating a detectable signal; and c) detecting IgG antibodies which may be present in the test sample by detecting a signal generated by the signal generating compound.

Also, the present invention includes a vaccine comprising: 1) *Toxoplasma gondii* antigens P29, P30 and P35 and 2) a pharmaceutically acceptable adjuvant as well as a vaccine comprising: 1) *Toxoplasma gondii* antigens P29, P35 and P66 and 2) a pharmaceutically acceptable adjuvant.

Additionally, the present invention includes a kit for determining the presence of IgM antibodies to *Toxoplasma gondii* in a test sample comprising: a) a composition comprising *Toxoplasma gondii* antigens P29, P35 and P66 and b) a conjugate comprising an antibody attached to a signal generating compound capable of generating a detectable signal.

The present invention also includes a kit for determining the presence of IgG antibodies to *Toxoplasma gondii* in a test sample comprising: a) a composition comprising *Toxoplasma gondii* antigens P29, P30 and P35 and b) a conjugate comprising an antibody attached to a signal generating compound capable of generating a detectable signal.

An additional kit for determining the presence of IgM antibodies to *Toxoplasma gondii* in a test sample, encompassed by the present invention, comprises: a) an anti-antibody specific for IgM antibody and b) a composition comprising *Toxoplasma gondii* antigens P29, P35 and P66.

The present invention also includes a kit for determining the presence of IgM antibodies to *Toxoplasma gondii* in a test sample comprising: a) an anti-antibody specific for IgM antibody and b) a conjugate comprising: 1) *Toxoplasma gondii* antigens P29, P35 and P66, each attached to 2) a signal generating compound capable of generating a detectable signal.

Additionally, the present invention includes a kit for determining the presence of IgG antibodies to *Toxoplasma gondii* in a test sample comprising: a) an anti-antibody specific for IgG antibody and b) a composition comprising *Toxoplasma gondii* antigens P29, P30 and P35.

The present invention also includes an additional kit for determining the presence of antibodies to *Toxoplasma gondii* in a test sample comprising: a) an anti-antibody specific for IgG antibody and b) a conjugate comprising: 1) *Toxoplasma gondii* antigens P29, P30 and P35, each attached to 2) a signal generating compound capable of generating a detectable signal.

Additionally, the present invention includes a method for detecting the presence of IgM antibodies to *Toxoplasma gondii* in a test sample comprising the steps of: (a) contacting the test sample suspected of containing IgM antibodies with anti-antibody specific for the IgM antibodies for a time and under conditions sufficient to allow for formation of anti-antibody IgM complexes; (b) adding antigen to resulting anti-antibody/IgM complexes for a time and under conditions sufficient to allow the antigen to bind to bound IgM antibody, the antigen comprising a mixture of P29, P35 and P66; and (c) adding a conjugate to resulting anti-antibody/IgM/antigen complexes, the conjugate comprising a composition comprising monoclonal or polyclonal antibody attached to a signal generating compound capable of generating a detectable signal; and (d) detecting IgM antibodies which may be present in the test sample by detecting a signal generated by the signal generating compound.

The present invention also includes a method for detecting the presence of IgG antibodies to *Toxoplasma gondii* in a test sample comprising the steps of: (a) contacting the test sample suspected of containing IgG antibodies with anti-antibody specific for said IgG antibodies for a time and under conditions sufficient to allow for formation of anti-antibody IgG complexes; (b) adding antigen to resulting anti-antibody/IgG complexes for a time and under conditions sufficient to allow said antigen to bind to bound IgG antibody, the antigen comprising a mixture of P29, P30 and P35; and (c) adding a conjugate to resulting anti-antibody/IgG/antigen complexes, the conjugate comprising a composition comprising monoclonal or polyclonal antibody attached to a signal generating compound capable of generating a detectable signal; and (d) detecting IgG antibodies which may be present in the test sample by detecting a signal generated by the signal generating compound.

A further method for detecting the presence of IgM and IgG antibodies to *Toxoplasma gondii* in a test sample, included within the present invention, comprises the steps of: a) contacting the test sample suspected of containing the IgM and IgG antibodies with a composition comprising antigen P29, P30, P35 and P66 for a time and under conditions sufficient for the formation of IgM antibody/antigen complexes and IgG antibody/antigen complexes; b) adding a conjugate to the resulting IgM antibody/antigen complexes and IgG antibody/antigen complexes for a time and under conditions sufficient to allow the conjugate to bind to the bound IgM and IgG antibody, wherein said conjugate comprises an antibody attached to a signal generating compound capable of generating a detectable signal; and c) detecting the presence of IgM and IgG antibodies which may be present in the test sample by detecting a signal generated by the signal generating compound.

The present invention also includes method for detecting the presence of IgM and IgG antibodies to *Toxoplasma gondii* in a test sample comprising the steps of: a) contacting the test sample suspected of containing the IgM and IgG antibodies with anti-antibody specific for said IgM antibodies and the IgG antibodies for a time and under conditions sufficient to allow for formation of anti-antibody/IgM antibody complexes and anti-antibody/IgG antibody complexes; b) adding a conjugate to resulting anti-antibody/IgM antibody complexes and resulting anti-antibody/IgG antibody complexes for a time and under conditions sufficient to allow the conjugate to bind to bound antibody, wherein the conjugate comprises P29, P30, P35 and P66, each attached to a signal generating compound capable of generating a detectable signal; and c) detecting IgM and IgG antibodies which may be present in the test sample by detecting a signal generated by the signal generating compound.

The present invention also includes a method for detecting the presence of IgM and IgG antibodies to *Toxoplasma gondii* in a test sample comprising the steps of: (a) contacting the test sample suspected of containing IgM and IgG antibodies with anti-antibody specific for the IgM antibodies and with anti-antibody specific for the IgG antibodies for a time and under conditions sufficient to allow for formation of anti-antibody/IgM complexes and anti-antibody/IgG complexes; (b) adding antigen to resulting anti-antibody/IgM complexes and resulting anti-antibody/IgG complexes for a time and under conditions sufficient to allow the antigen to bind to bound IgM antibody and bound IgG antibody, the antigen comprising a mixture of P29, P30, P35 and P66; and (c) adding a conjugate to resulting anti-antibody/IgM/antigen complexes and anti-antibody/IgG/antigen complexes, the conjugate comprising a composition comprising monoclonal or polyclonal antibody attached to a signal generating compound capable of generating a detectable signal; and (d) detecting IgM and IgG antibodies which may be present in the test sample by detecting a signal generated by the signal generating compound.

Additionally, the present invention encompasses a method of producing monoclonal antibodies comprising the steps of:

a) injecting a non-human mammal with an antigen;
b) administering a composition comprising antibiotics to the non-human mammal;
c) fusing spleen cells of the non-human mammal with myeloma cells in order to generate hybridomas; and
d) culturing the hybridomas under sufficient time and conditions such that the hybridomas produce monoclonal antibodies.

The antigen utilized may be derived from, for example, *T. gondii*.

All U.S. patents and publications referred to herein are hereby incorporated in their entirety by reference.

BRIEF DESCRIPTION OF THE DRAWINGS

FIGS. 1A–1C represent the DNA sequence [SEQ ID NO: 23] of nucleotides 1–1268 and the corresponding amino acid sequence [SEQ ID NO: 24] of plasmid pGM613.

FIG. 2 represents the DNA sequence [SEQ ID NO: 25] of nucleotides 1–477 of plasmid pTXG1-2.

FIGS. 3A–3D represent the composite DNA sequence [SEQ ID NO: 26] of nucleotides 1–1648 and the corresponding amino acid sequence [SEQ ID NO: 27] for the P29 gene.

FIG. 5 is a schematic representation of (A) the construction of plasmid pEE3; and (B) the nucleotide sequence [SEQ ID NO: 32] and the corresponding amino acid sequence [SEQ ID NO: 51] of the synthetic DNA polylinker to be introduced into the StuI/MluI sites of pEE2 to generate plasmid pEE3.

FIGS. 7A–7J illustrates the DNA sequence [SEQ ID NO: 37] of nucleotides 1–4775 and the corresponding amino acid sequence [SEQ ID NO: 52] of the CKS-P29-CKS fusion protein of plasmid pToxo-P29.

FIGS. 9A–9J represent the DNA sequence [SEQ ID NO: 40] of nucleotides 1–4910 and the corresponding amino acid sequence [SEQ ID NO: 53] of the CKS-P30-CKS fusion protein of plasmid pToxo-P30.

FIGS. 11A–11I illustrate the DNA sequence [SEQ ID NO: 45] of nucleotides 1–4451 and the corresponding amino acid sequence [SEQ ID NO: 54] of the CKS-P35-CKS fusion protein of plasmid pToxo-P35S.

FIGS. 13A–13K represent the DNA sequence [SEQ ID NO: 48] of nucleotides 1–5258 and the corresponding amino acid sequence [SEQ ID NO: 55] of the CKS-P66-CKS fusion protein of plasmid pToxo-P66g.

DETAILED DESCRIPTION OF THE INVENTION

Figure 4A:
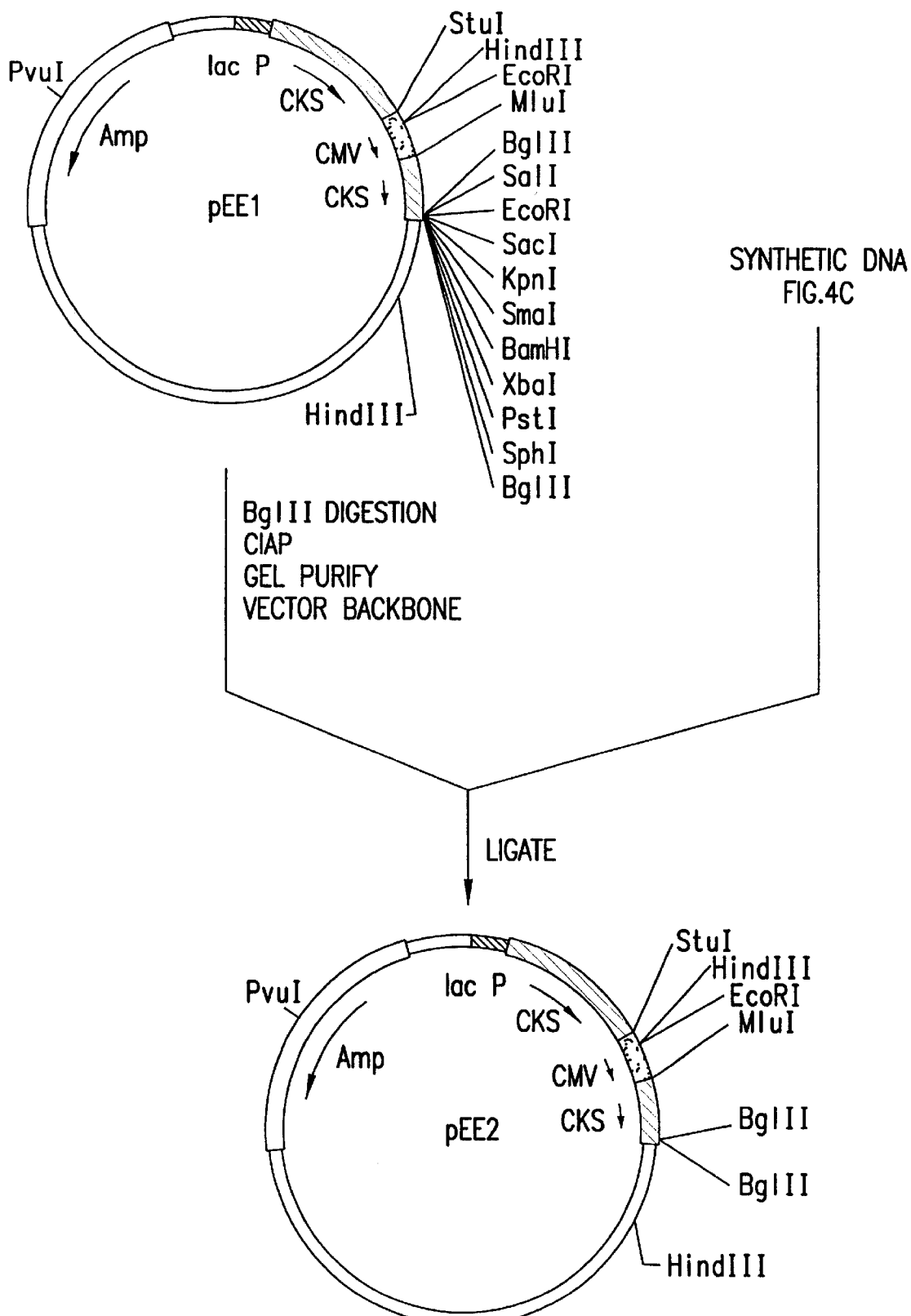
FIG. 4 is a schematic representation of (A) the construction of plasmid pEE2; (B) the nucleotide sequence [SEQ ID NO: 28] and the corresponding amino acid sequence [SEQ ID NO: 49] of the polylinker to be removed from pEE1 by digestion with BglII; and (C) the nucleotide sequence [SEQ ID NO: 29] and the corresponding amino acid sequence [SEQ ID NO: 50] of the synthetic DNA to be introduced into the BglII site of pEE1 to generate plasmid pEE2.

The difficulties of known assays for the detection of IgG and IgM antibodies to *T. gondii* have been described, in detail, above. Thus, there was a need to discover immunoassays which could accurately detect the presence of such antibodies in positive serum, thereby eliminating the problem of false negative or false positive tests. The present invention provides such needed immunoassays and, in particular, combinations of antigens which accurately detect the presence of IgG or IgM antibodies in human sera.

In particular, the present invention includes a novel antigen which, for purposes of the present invention, is referred to as P29. The nucleotide sequence of the gene encoding this antigen is shown in FIG. 3 and is represented by SEQ ID NO. 26. The amino acid sequence of this antigen is shown in FIG. 3 and is represented by SEQ ID NO. 27.

P29, a dense granule protein, when used in combination with other known antigens, may accurately detect the presence of IgG or IgM in human sera. In particular, P29, when used in combination with other known antigens, may replace the tachyzoite previously used in assays for *T. gondii* antibodies.

Furthermore, the present invention also includes a polyclonal or monoclonal antibody raised against P29. Such an antibody may be used, for example, in an immunoassay, a vaccine, a kit, or for research purposes.

The present invention also encompasses a composition or mixture comprising the following three antigens: P29, P30 and P35. This combination or mixture of antigens may be utilized for the detection of IgG in IgG-positive sera (i.e., as a diagnostic reagent). Furthermore, the antigens may be produced either recombinantly or synthetically. Additionally, the present invention also includes a composition comprising antibodies raised against these antigens.

The present invention also includes a composition or mixture comprising the following three antigens: P29, P35 and P66. This combination or mixture of antigens may be used for the detection of IgM in IgM-positive sera (i.e., as a diagnostic reagent), and the antigens may be produced either recombinantly or synthetically. Furthermore, the present invention also includes a composition comprising antibodies raised against these antigens.

If, in fact, one wishes to measure both the titer of IgM and IgG in an individual, then a composition or mixture of antigens P29, P30, P35 and P66 may be utilized in an immunoassay. Such a combination of antigens is also included within the scope of the present invention.

The present invention also includes methods of detecting IgM and/or IgG using the combinations of antigens described above. More specifically, there are two basic types of assays, competitive and non-competitive (e.g., immunometric and sandwich). In both assays, antibody or antigen reagents are covalently or non-covalently attached to the solid phase. Linking agents for covalent attachment are known and may be part of the solid phase or derivatized to it prior to coating. Examples of solid phases used in immunoassays are porous and non-porous materials, latex particles, magnetic particles, microparticles, beads, membranes, microtiter wells and plastic tubes. The choice of solid phase material and method of labeling the antigen or antibody reagent are determined based upon desired assay format performance characteristics. For some immunoassays, no label is required. For example, if the antigen is on a detectable particle such as a red blood cell, reactivity can be established based upon agglutination. Alternatively, an antigen-antibody reaction may result in a visible change (e.g., radial immunodiffusion). In most cases, one of the antibody or antigen reagents used in an immunoassay is attached to a signal generating compound or "label". This signal generating compound or "label" is in itself detectable or may be reacted with one or more additional compounds to generate a detectable product. Examples of such signal generating compounds include chromogens, radioisotopes (e.g., 125I, 131I, 32P, 3H, 35S, and 14C), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

There are two general formats commonly used to monitor specific antibody titer and type in humans: (1) antigen is presented on a solid phase, as described above, the human biological fluid containing the specific antibodies is allowed to react with the antigen, and then antibody bound to antigen is detected with an anti-human antibody coupled to a signal generating compound and (2) an anti-human antibody is bound to the solid phase, the human biological fluid containing specific antibodies is allowed to react with the bound antibody, and then antigen attached to a signal generating compound is added to detect specific antibody present in the fluid sample. In both formats, the anti-human antibody reagent may recognize all antibody classes, or alternatively, be specific for a particular class or subclass of antibody, depending upon the intended purpose of the assay. These assays formats as well as other known formats are intended to be within the scope of the present invention and are well known to those of ordinary skill in the art.

In particular, two illustrative examples of an immunometric antibody-capture based immunoassay are the Imx Toxo IgM and Toxo IgG antibody assays manufactured by Abbott Laboratories (Abbott Park, Ill.). Both assays are automated Microparticle Enzyme Immunoasssays (MEIA) which measure antibodies to *Toxoplasma gondii* (*T. gondii*) in human serum or plasma (Safford et al., *J. Clin. Pathol.* 44:238–242 (1991)). One assay quantitatively measures IgM antibodies, indicative of recent exposure or acute infection, and the other assay quantitatively measures IgG, indicative of chronic or past infection. These assays use microparticles coated with *T. gondii* antigens as the solid phase. In particular, specimen is added to the coated microparticles to allow antibodies specific for *T. gondii* to bind. Subsequently, an alkaline phosphatase conjugated anti-human IgM (or anti-human IgG) is added that specifically binds to IgM (or IgG) class antibodies complexed to the *T. gondii* antigens. Following addition of a suitable substrate (e.g., 4-methyumbelliferyl phosphate), the rate of enzyme-catalyzed turnover is monitored based upon fluorescence.

The mixture of P29, P30 and P35 may be used in the IgG Abbott immunoassay, and the mixture of P29, P35 and P66 may be utilized in the IgM Abbott immunoassay. Additionally, A mixture of P29, P30, P35, and P66 may be utilized in either assay, if desired. Furthermore, it must be noted that other non-Abbott assays or platforms may also be utilized, with each of the combinations of antigens (i.e., 3 or 4 antigens), for purposes of the present invention.

Thus, the present invention includes a method of detecting IgM antibodies in a test sample comprising the steps of: (a) contacting the test sample suspected of containing the IgM antibodies with P29, P35 and P66; (b) detecting the presence of IgM antibodies present in the test sample. More specifically, the present invention includes a method of detecting IgM antibodies in a test sample comprising the steps of: (a) contacting the test sample suspected of containing the IgM antibodies with P29, P35 and P66 for a time and under conditions sufficient to allow the formation of IgM antibody/antigen complexes; (b) adding a conjugate to the resulting IgM antibody/antigen complexes for a time and under conditions sufficient to allow the conjugate to bind to the bound antibody, the conjugate comprising an antibody (directed against the IgM) attached to a signal generating compound capable of generating a detectable signal; (c) detecting the presence of the IgM antibody which may be present in the test sample by detecting the signal generated by the signal generating compound. A control or calibrator may also be used which binds to the antigens. Furthermore, the method may also comprise the use of P30 in addition P29, P35 and P66.

In each of the above assays, IgG may be detected by substituting the P29, P35 and P66 mixture with a P29, P30 and P35 mixture. Additionally, the antibody in the conjugate will be directed against IgG rather than IgM. Additionally, if one wishes to detect both IgM and IgG antibodies, P29, P30, P35 and P66 may be utilized in the immunoassay. Furthermore, if desired, one may also add P66 to the assay, even if detection of antibodies to only IgG is required.

Additionally, the present invention also includes a method for detecting the presence of IgM which may be present in a test sample. This method comprises the steps of: (a) contacting the test sample suspected of containing IgM antibodies with anti-antibody specific for the IgM, for a time and under conditions sufficient to allow for formation of anti-antibody/IgM complexes and (b) detecting the presence of IgM which may be present in the test sample. (Such anti-antibodies are commercially available and may be created, for example, by immunizing a mammal with purified mu-chain of the antibody.)

More specifically, this method may comprise the steps of: (a) contacting the test sample suspected of containing the IgM antibodies with anti-antibody specific for the IgM, under time and conditions sufficient to allow the formation of anti-antibody/IgM complexes; (b) adding a conjugate to the resulting anti-antibody/IgM complexes for a time and under conditions sufficient to allow the conjugate to bind to the bound antibody, the conjugate comprising P29, P35 and P66, each being attached to a signal generating compound capable of generating a detectable signal; and (c) detecting the presence of the IgM antibodies which may be present in the test sample by detecting the signal generated by the signal generating compound. A control or calibrator may be used which comprises antibody to the anti-antibody. Furthermore, the conjugate may also comprise P30, if desired.

In each of the above assays, IgG may be detected by substituting the P29, P35 and P66 mixture with a P29, P30 and P35 mixture. Also, anti-antibody specific for IgG will be used. Additionally, if one wishes to detect both IgM and IgG antibodies, P29, P30, P35 and P66 may be utilized in the immunoassay. Moreover, even if one wishes to detect IgG only, P66 may also be added to the assay, if desired.

The present invention also encompasses a third method for detecting the presence of IgM in a test sample. This method comprises the steps of: (a) contacting the test sample suspected of containing IgM antibodies with anti-antibody specific for the IgM, under time and conditions sufficient to allow the formation of anti-antibody IgM compelxes; (b) adding antigen to the resulting anti-antibody/IgM complexes for a time and under conditions sufficient to allow the antigen to bind to the bound IgM antibody, the antigen comprising a mixture of P29, P35 and P66; and (c) adding a conjugate to the resulting anti-antibody/IgM/antigen complexes, the conjugate comprising a composition comprising monoclonal or polyclonal antibody attached to a signal generating compound capable of detecting a detectable signal, the monoclonal or polyclonal antibody being directed against the antigen; and (d) detecting the presence of the IgM antibodies which may be present in the test sample by detecting the signal generated by the signal generating compound. Again, a control or calibrator may be used which comprises antibody to the anti-antibody. The antigen mixture may further comprise P30, if desired.

In this method, IgG may be detected by substituting the P29, P35 and P66 mixture with a P29, P30 and P35 mixture and utilizing anti-antibody specific for IgG. However, if one wishes to detect both IgM and IgG antibodies, P29, P30, P35 and P66 may be utilized in the immunoassay. Even if one wishes to detect IgG alone, the assay may further comprise the use of P66.

It should also be noted that all of the above methods may be used to detect IgA antibodies (with an alpha-specific conjugate) and/or IgE antibodies (with an epsilon-specific conjugate) should such detection be desired.

Additionally, the present invention also includes a vaccine comprising a mixture of P29, P30 and P35 antigens and a pharmaceutically acceptable adjuvant. Such a vaccine may be administered if one desires to raise IgG antibodies in a mammal. The present invention also includes a vaccine comprising a mixture of P29, P35 and P66 antigens and a pharmaceutically acceptable adjuvant (e.g., Freund's adjuvant or Phosphate Buffered Saline). Such a vaccine may be administered if one desires to raise IgM antibodies in a mammal. Additionally, the present invention also includes a vaccine comprising a mixture of P29, P30, P35 and P66 antigens as well as a pharmaceutically acceptable adjuvant. This vaccine should be administered if one desires to raise both IgM and IgG antibodies in a mammal.

Kits are also included within the scope of the present invention. More specifically, the present invention includes kits for determining the presence of IgG and/or IgM. In particular, a kit for determining the presence of IgM in a test sample comprises a) a mixture of P29, P35 and P66; and b) a conjugate comprising an antibody (directed against IgM) attached to a signal generating compound capable of generating a detectable signal. The kit may also contain a control or calibrator which comprises a reagent which binds to P29, P35 and P66.

Again, if one desires to detect IgG, rather than IgM, the kit will comprise a mixture of P29, P30 and P35, rather than P29, P35 and P66, as well as an antibody directed against IgG. If one wishes to detect both IgM and IgG, the kit will comprise P29, P30, P35 and P66.

The present invention also includes another type of kit for detecting IgM and/or IgG in a test sample. If utilized for detecting the presence of IgM, the kit may comprise a) an anti-antibody specific for IgM, and b) a mixture of antigens P29, P35 and P66. A control or calibrator comprising a reagent which binds to P29, P35 and P66 may also be included. More specifically, the kit may comprise a) an anti-antibody specific for IgM, and b) a conjugate comprising P29, P35 and P66, the conjugate being attached to a signal generating compound capable of generating a detectable signal. Again, the kit may also comprise a control of calibrator comprising a reagent which binds to P29, P35 and P66.

Additionally, if one desires to detect IgG, rather than IgM, the kit will comprise a mixture of P29, P30 and P35, rather than P29, P35 and P66, as well as anti-antibody specific for IgG. If one wishes to detect both IgM and IgG, the kit may comprise P29, P30, P35 and P66.

The present invention may be illustrated by the use of the following non-limiting examples:

EXAMPLE 1

General Methodology
Materials and Sources

Restriction enzymes, T4 DNA ligase, calf intestinal alkaline phosphatase (CIAP), polynucleotide kinase, and the Klenow fragment of DNA Polymerase I were purchased from New England Biolabs, Inc. (Beverly, Mass.) or from Boehringer Mannheim Corp. (Indianapolis, Ind.). DNaseI and aprotinin were purchased from Boehringer Mannheim Corp.

DNA and protein molecular weight standards, Daiichi pre-cast gradient polyacrylamide gels were obtained from Integrated Separation Systems, Inc. (Natick, Mass.).

Isopropyl-β-D-thiogalactoside (IPTG), TRITON X-100, 4-chloro-1-naphthol, and sodium dodecyl sulfate (SDS) were purchased from BioRad Laboratories (Richmond, Calif.).

Plasma from patients with an acute Toxoplasma infection was obtained from Antibody Systems, Inc., Bedford, Tex.

Horseradish peroxidase (HRPO)-labelled antibodies were purchased from Kirkegaard & Perry Laboratories, Inc. (Gaithersburg, Md.).

EPICURIAN Coli™ XL-1 BLUE (recA1 endA1 gyrA96 thi-1 hsdR17 supE44 relA1 lac [F' proAB lacI$^q$ ZDM15 Tn10 (Tet$^r$)]) supercompetent $E.$ $coli$ cells, a DNA isolation kit, a RNA isolation kit, a ZAP™-cDNA Gigapack II Gold Cloning kit, a picoBLUE Immunoscreening kit, and Duralose-UV™ membranes, and a ZAP™-cDNA Synthesis kit were obtained from Stratagene Cloning Systems, Inc. (La Jolla, Calif.).

A GeneAmp™ reagent kit and AmpliTaq™ DNA Polymerase were purchased from Perkin-Elmer Cetus (Norwalk, Conn.). Deoxynucleotide triphosphates used in general procedures were from the GeneAmp™ reagent kit.

Supported nitrocellulose membrane was purchased from Schleicher & Schuell (Keene, N.H.).

A nucleotide kit for DNA sequencing with Sequenase™ and 7-deaza-dGTP and Sequenase™ version 2.0 DNA Polymerase were obtained from U.S. Biochemical Corp. (Cleveland, Ohio).

A Multiprime DNA labelling kit, alpha-$^{32}$P-dCTP, and a-$^{32}$P-dATP were purchased from Amersham Corp. (Arlington Heights, Ill.).

A PolyA$^+$mRNA purification kit was purchased from Pharmacia LKB Biotechnology, Inc. (Piscataway, N.J.).

Polygard Cartridge filters, pore size 10 u, were purchased from Millipore Corp., Bedford, Mass.

Luria Broth plates with ampicillin (LBamp plates) were purchased from Micro Diagnostics, Inc. (Lombard, Ill.).

OPTI-MEM™ Medium, Iscove's Modified Dulbecco's Media, Hank's Balanced Salt Solution, fetal calf serum, phosphate-buffered saline, competent $E.$ $coli$ DH5-alpha (F$^{-\emptyset}$80dlacZDM15 D(lacZYA-argF)U169 deoR recA1 endA1 phoA hsdR17($r_k^-$, $m_k^+$) supE44 l$^-$ thi-1 grA96 relA1), and ultraPURE agarose were purchased from GIBCO BRL, Inc. (Grand Island, N.Y.).

Bacto-Tryptone, Bacto-Yeast Extract, and Bacto-Agar were obtained from Difco Laboratories (Detroit, Mich.).

NZY Broth was purchased from Becton Dickinson Microbiology Systems (Cockeysville, Md.).

Salmon sperm DNA, lysozyme, ampicillin, N-lauroyl sarcosine, thimerosal, buffers, casein acid hydrolysate, TWEEN 20™ (polyoxyethylenesorbitan monolaurate), diethylpyrocarbonate (DEPC), phenylmethylsulfonylfluoride (PMSF), bovine serum albumin (BSA), urea, glycerol, EDTA, sodium deoxycholate, pyrimethamine, sulfamethoxazole, mouse monoclonal antibody isotyping kits, and inorganic salts were purchased from Sigma Chemical Co. (Saint Louis, Mo.).

OPD (0-phenylenediamine dihydrochloride) and PBS (phosphate buffered saline) was purchased from Abbott Laboratories (Abbott Park, Ill.).

Hydrogen Peroxide ($H_{2O2}$) was purchased from Mallinkrodt (Paris, Ky.).

Methanol was purchased from EM Science (Gibbstown, N.J.).

Microtiter MAXISORPIplates were purchased from NUNC, Inc. (Naperville, Ill.).

Media, Buffers and General Reagents

"Superbroth II" contained 11.25 g/L tryptone, 22.5 g/L yeast extract, 11.4 g/L potassium phosphate dibasic, 1.7 g/L potassium phosphate monobasic, 10 mL/L glycerol, adjusted pH to 7.2 with sodium hydroxide.

"Tris-buffered saline" or "TBS" consisted of 20 mM Tris, 500 mM NaCl at pH 7.5.

"Tris-buffered saline TWEEN 20™" or "TBST" consisted of TBS plus 0.05% TWEEN 20.

"Rubazyme specimen dilution buffer" or "Rubazyme SDB" consisted of 100 mM Tris at pH 7.5 with 135 mM NaCl, 10 mM EDTA, 0.2% TWEEN 20™, 0.01% thimerosal and 4% bovine calf serum.

"Rubazyme conjugate diluent dilution buffer" consisted of 100 mM Trisat pH 7.5 with 135 mM NaCl, 0.01% thimerosal and 10% bovine calf serum.

"Membrane blocking solution" consisted of 1% BSA, 1% casein acid hydrolysate, 0.05% TWEEN 20 in TBS.

"TE buffer" consisted of 10 mM Tris and 1 mM EDTA at pH 8.0.

"TEM lysis buffer" consisted of 50 mM Tris, 10 mM EDTA and 20 mM magnesium chloride at pH 8.5.

"PTE buffer" consisted of 50 mM Tris and 10 mM EDTA at pH 8.5.

Parasite, Cell, and Mouse Lines

The RH strain of $T.$ $gondii$ (ATCC 50174) and the HeLa S3 cell line (ATCC CCL 2.2) were obtained from the American Type Culture Collection, 10801 University Boulevard, Manassas, Va. 20110-2209. The TS4 strain of $T.$ $gondii$ was also available from the American Type Culture Collection and from other sources. The Swiss mouse strain CD1 was obtained from Charles River Laboratories, Wilmington, Mass. Parasites were maintained by serial passage in the peritoneal cavity of Swiss mice. Tachyzoites were collected from the peritoneal cavity and used to inoculate a primary suspension culture of HeLa S3 cells.

This infected suspension culture was grown for 2–4 days at 37° C. in Iscove's Modified Dulbecco's Media and then used to inoculate a secondary suspension culture of uninfected HeLa S3 cells. This secondary infected suspension culture was grown for 2–4 days at 37° C. in OPTI-MEM Reduced Serum Medium and used as a source of tachyzoites for screening monoclonal antibodies and for the preparation of DNA, RNA, and total tachyzoite protein.

General Methods

All enzyme digestions of DNA were performed according to suppliers' instructions. At least 5 units of enzyme were used per microgram of DNA, and sufficient incubation time was allowed for complete digestion of DNA. Supplier protocols were followed for the various kits used in manipulation of DNA and RNA, for polymerase chain reaction (PCR) DNA synthesis and for DNA sequencing. Standard procedures were used for Western and Southern Blots, partial restriction enzyme digestion of Toxoplasma genomic DNA with Sau 3AI, construction of a Toxoplasma genomic library, miniprep and large scale preparation of plasmid DNA from *E. coli*, preparation of phage lysate DNA from *E. coli* cells infected with phage lambda, preparation of *E. coli* lysates for the absorption of anti-*E. coli* antibodies, phenol-chloroform extraction and ethanol precipitation of DNA, restriction analysis of DNA on agarose gels, purification of DNA fragments from agarose gels, filling the recessed 3' termini created by digestion with restriction enzymes using the Klenow fragment of DNA Polymerase I, and ligation of DNA fragments with T4 DNA ligase. (Maniatis et al., *Molecular Cloning: A Laboratory Manual*, 2nd ed. (Cold Spring Harbor Laboratory Press, New York, 1989)).

DNA fragments for cloning into plasmids that were generated by PCR amplification, were extracted with phenol-chloroform and precipitated with ethanol prior to restriction enzyme digestion of the PCR reaction mixture. Oligonucleotides for PCR and DNA sequencing were synthesized on an Applied Biosystems Oligonucleotide Synthesizer, model 380B or 394, per the manufacturer's protocol.

Mouse monoclonal antibody directed against the CKS protein was obtained by immunization of mice with purified rpHCV-23 (CKS-BCD), described in International Application No. WO93/04088 by Dailey et al. The proteins used for immunization were approximately 90% pure as determined by SDS-PAGE. The procedure for the immunization of mice, cell fusion, screening and cloning of monoclonal antibodies, and characterization of monoclonal antibodies were as described in Published International Application No. WO92/08738 by Mehta et al.

EXAMPLE 2

Isolation of Toxoplasma DNA, RNA, Protein and Synthesis of cDNA

A 10L secondary suspension culture of HeLa cells infected with the RH strain of *T. gondii* was grown to a tachyzoite density of approximately $1 \times 10^7$ per ml and filtered through a 10 m Millipore Polygard cartridge filter to remove HeLa cells from the tachyzoites. The tachyzoite filtrate obtained contained less than 1% HeLa cells. The tachyzoites were then concentrated by centrifugation, washed and resuspended in 1× Hank's Buffer. The tachyzoite concentrate was then pipetted dropwise into liquid nitrogen, and the frozen tachyzoite pellets were recovered and stored at −80° C. until further use. The tachyzoite pellets were converted to tachyzoite powder by grinding the pellets to a fine powder using a mortar and pestle chilled with dry ice and liquid nitrogen. The tachyzoite powder was subsequently used for the isolation of tachyzoite nucleic acid and protein as described below.

Step A: Isolation of Toxoplasma DNA

Total Toxoplasma DNA was isolated from the tachyzoite powder using the Stratagene DNA extraction kit. The tachyzoite powder was dissolved in Solution 2, and total DNA was isolated following the kit's protocol. After ethanol precipitation and resuspension of the DNA in TE buffer, undissolved DNA and contaminating polysaccharides were removed by centrifugation at 200,000×g for 1 hr.

Step B: Isolation of Toxoplasma RNA

Total Toxoplasma RNA was isolated from the tachyzoite powder using the Stratagene RNA isolation kit. The tachyzoite powder was dissolved in Solution D, and total RNA was isolated following the kit's protocol. After ethanol precipitation and resuspension of the RNA in DEPC-treated water, polyA+RNA was selected with an oligo-dT column using a Pharmacia mRNA isolation kit. The purified mRNA was concentrated by ethanol precipitation and stored in DEPC-treated water at −80° C. until further use.

Step C: Isolation of Total Toxoplasma Protein

Total Toxoplasma protein was isolated from the tachyzoite powder by dissolving the powder in SDS-PAGE loading buffer and boiling the sample for 5 min. The protein preparation was stored at −20° C. until further use.

Step D: Synthesis of Toxoplasma cDNA

Purified Toxoplasma mRNA was used as a template for the synthesis of cDNA using the Stratagene ZAP-cDNA Synthesis kit. The first strand was synthesized using Moloney-Murine Leukemia Virus Reverse Transcriptase and a 50 mer primer which included an Xho I restriction enzyme site and an poly-dT tract. The reaction mix included the analog 5-methyl dCTP to protect the cDNA from restriction enzymes used in subsequent cloning steps. The second strand was synthesized using RNase H and DNA polymerase I. The cDNA was then ethanol precipitated and resuspended in water and stored at −20° C. until further use as a template for PCR amplification and for construction of a Toxoplasma cDNA library.

EXAMPLE 3

Cloning Strategy for Genes Encoding Toxoplasma Antigens

The immune response that is generated by human patients with Toxoplasmosis is targeted against several *T. gondii* proteins and varies by individual and by the disease stage. Hence, a Toxoplasma immunoassay which is composed entirely of purified protein antigens will require more than one protein serological target to accurately detect serum antibody to *T. gondii* in a population of Toxoplasma infected individuals. In order to identify additional Toxoplasma antigens which are relevant for human diagnostic testing, a two-tiered cloning strategy for genes encoding Toxoplasma antigens was undertaken. The first-tier consisted of cloning known genes encoding Toxoplasma antigens, by using the published DNA sequences for these genes. The second-tier consisted of cloning novel, previously undescribed genes encoding Toxoplasma antigens, by using pooled human plasma from patients with toxoplasmosis to screen a Toxoplasma cDNA library. The genes cloned in the first tier were then used as DNA probes to screen the genes cloned in the second tier for uniqueness.

Step A: Cloning of Toxoplasma Genes Encoding Known Toxoplasma Antigens

The CKS expression vector pJO200 described in U.S. patent application Ser. No. 08/742,619 of Maine and Chovan allows the fusion of recombinant proteins to the CMP-KDO synthetase (CKS) protein. The DNA gene sequence which encodes for the structural protein CKS (also known as the kdsB gene) is published in Goldman et al., J. Biol. Chem. 261:15831 (1986). The amino acid sequence of CKS includes 248 amino acid (aa) residues and is described in Goldman et al., supra. The pJO200 vector contained DNA encoding the sequence of the first 240 amino acids from the original kdsB gene followed by an additional 20 amino acids encoded for by the polylinker DNA sequence, for a total of 260 amino acids.

Oligonucleotide primers for use in the PCR amplification of known genes encoding Toxoplasma antigens were designed based on published DNA sequences. Each pair of PCR primers were "tailed" with additional DNA sequences to include restriction enzyme sites for subsequent cloning into the pJO200 CKS expression vector. PCR amplification of each Toxoplasma gene with the appropriate primers was carried out using the GeneAmp reagent kit and AmpliTaq DNA Polymerase purchased from Perkin-Elmer Cetus, Norwalk, Conn., following the kit's protocol. Approximately 20 ng of Toxoplasma cDNA prepared in Example 2D or 20 ng of Toxoplasma genomic DNA prepared in Example 2A (for P66 genomic clone only) was used in each reaction. The amplification cycles were 1 cycle of 95° C. for 120 sec., followed by 35 cycles of 95° C. for 60 sec., 55° C. for 60 sec., 72° C. for 120 sec., followed by 1 cycle at 72° C. for 300 sec., followed by a soak cycle at 4° C. The PCR products obtained from the amplification reaction were then digested with the appropriate restriction enzymes, purified on agarose gels, ligated into the pJO200 vector cut with the appropriate restriction enzymes and transformed into the Epicurean Coli XL-1 Blue Supercompetent *E. coli* cells following the kit protocol. Correct clones were confirmed by DNA sequence analysis of the cloned Toxoplasma DNA. The DNA sequences of the oligonucleotide primers used for the PCR amplification of the following Toxoplasma genes are shown below and how they were cloned into the pJO200 CKS vector:

Toxo P22 (SAG2) Gene (Prince et al. (1990) Mol. Biochem. Parasitol 43, 97–106)

Sense Primer [SEQ ID NO:1]:

5'-CGCAGAATTCGATGTCCACCACCGAGACGCCA GCGCCCATTGA-3' (EcoRI site is underlined)

Antisense Primer [SEQ ID NO:2]:

5'-CCCGGGATCCTTACACAAACGTGATCAACAAA CCTGCGAGACC-3' (BamH-I site is underlined)

Region Cloned: Nucleotides 260–739 of the Toxo P22 gene cloned into the EcoRI/BamH-I sites of pJO200 to yield plasmid pJO200-P22.

Toxo P24 (GRA1) Gene (Cesbron-Delauw et al. (1989) Proc. Nat. Acad. Sci. 86, 7537–7541)

Sense Primer [SEQ ID NO:3]:

5'-GGCCGAATTCGATGGCCGAAGGCGGCGACAA CCAGT-3' (EcoRI site is underlined)

Antisense Primer [SEQ ID NO:4]:

5'-GCCCGGATCCTTACTCTCTCTCTCCTGTTAGGA ACCCA-3' (BamH-I site is underlined)

Region Cloned: Nucleotides 685–1183 of the Toxo P24 gene cloned into the EcoRI/BamH-I sites of pJO200 to yield plasmid pJO200-P24.

Toxo P25 Gene (Johnson et al. (1991) Gene 99, 127–132) Sense Primer [SEQ ID NO:5]:

5'-GGCGAATTCGATGCAAGAGGAAATCAAAGAAG GGGTGGA-3' (EcoRI site is underlined)

Antisense Primer [SEQ ID NO:6]:

5'-CGCACTCTAGATCACCTCGGAGTCGAGCCCAA C-3' (XbaI site is underlined)

Region Cloned: Nucleotides 7–288 of the Toxo P25 gene cloned into the EcoRI/XbaI sites of pJO200 to yield plasmid pJO200-P25.

Toxo P28 (GRA2) Gene (Prince et al. (1989) Mol. Biochem. Parasitol. 34, 3–13)

Sense Primer [SEQ ID NO:7]:

5 1 ' - GGCGAATTCGATGAGCGGTAAACCTCT- TGATGA G-3' (EcoRI site is underlined)

Antisense Primer [SEQ ID NO:8]:

5'-CGCTAGGATCCTTACTGCGAAAAGTCTGGGAC- 3' (BamH-I site is underlined)

Region Cloned: Nucleotides 489–924 of the Toxo P28 gene cloned into the EcoRI/BamH-I sites of pJO200 to yield plasmid pJO200-P28.

Toxo P30 (SAGI) Gene (Burg et al. (1988) J. Immunol. 141, 3584–3591)

Sense Primer [SEQ ID NO:9]:

5'-GGCGAATTCGATGCTTGTTGCCAATCAAGTTGT CACC-3' (EcoRI site is underlined)

Antisense Primer [SEQ ID NO:10]:

5'-CGCTAGGATCCTCACGCGACACAAGCTGCGA- 3' (BamH-I site is underlined)

Region Cloned: Nucleotides 464–1318 of the Toxo P30 gene cloned into the EcoRI/BamH-I sites of pJO200 to yield plasmid pJO200-P30.

Toxo P35 Gene (Knapp et al. (1989) EPA 431541A2)

Sense Primer [SEQ ID NO:11]:

5 1 ' - GACGGCGAATTCGATGAACGGTC- CTTTGAGTTA TC-3' (EcoRI site is underlined)

Antisense Primer [SEQ ID NO:12]:

5'-CGCTAGGATCCTTAATTCTGCGTCGTTACGGT-3' (BamH-I site is underlined)

Region Cloned: Nucleotides 91–822 of the Toxo P35 gene cloned into the EcoRI/BamH-I sites of pJO200 to yield plasmid pJO200-P35.

Toxo P35 Gene Subclone#1 (1-135aa)

(Knapp et al. (1989) EPO 431541A2)

Sense Primer [SEQ ID NO:13]:

5'-GACGGCGAATTCGATGAACGGTCCTTTGAGTTA TC-3' (EcoRI site is underlined)

Antisense Primer [SEQ ID NO:14]:

5'-CGCTAGGATCCTCAATGGTGAACTGCCGGTATC TCC-3' (BamH-I site is underlined) Region Cloned: Nucleotides 91–495 of the Toxo P35 gene cloned into the EcoRI/BamH-I sites of pJO200 to yield plasmid pJO200-P35S.

Toxo P41 (GRA4) Gene (Mevelec et al. (1992) Mol. Biochem. Parasitol. 56, 227–238)

Sense Primer [SEQ ID NO:15]:

5'-GGCGAATTCGATGGGTGAGTGCAGCTTTGGTTC T-3' (EcoRI site is underlined)
Antisense Primer [SEQ ID NO:16]:
 5'-CGCACTCTAGATCACTCTTTGCGCATTCTTTCC A-3' (XbaI site is underlined)
Region Cloned: Nucleotides 133–1107 of the Toxo P41 gene cloned into EcoRI/XbaI sites of pJO200 to yield plasmid pJO200-P41.

Toxo P54 (ROP2) Gene (Saavedra et al. (1991) J. Immunol. 147, 1975–1982)
Sense Primer [SEQ ID NO:17]:
 5'-GCCTGAATTCGATGCACGTACAGCAAGGCGCT GGCGTTGT-3' (EcoRI site is underlined)
Antisense Primer [SEQ ID NO:18]:
 5 1'-CGCTAGGATCCTCAGAAGTCTCCATG-GCTTGCA ATGGGAGGA-3' (Cloned as a blunt end)
Region Cloned: Nucleotides 85–1620 of the Toxo P54 gene cloned into the EcoRI/SmaI sites of pJO200 to yield plasmid pJO200-P54.

Toxo P66 (ROP1) Gene (Knapp et al. (1989) EPA 431541A2)

(Ossorio et al. (1992) Mol. Biochem. Parasitol. 50, 1–15.
Sense Primer [SEQ ID NO:19]:
 5 1'-GGCGAATTCGATGAGCCACAATGGAGTCCCCG CTTATCCA-3' (EcoRI site is underlined)
Antisense Primer [SEQ ID NO:20]:
 5'-CGCTAGGATCCTTATTGCGATCCATCATCCTGCT CTCTTC-3' (BamH-I site is underlined)
Region Cloned: Nucleotides 122–1330 of the Toxo P66 gene cloned into the EcoRI/BamH-I sites of pJO200 to yield plasmid pJO200-P66 using Toxoplasma cDNA as template. Nucleotides 122–1330 of the Toxo P66 gene cloned into the EcoRI/BamH-I sites of pJO200 to yield plasmid pJO200-P66g using Toxoplasma genomic DNA as template.

Toxo P68 Gene (Knapp et al. (1989) EPA 431541A2)
Sense Primer [SEQ ID NO:21]:
 5'-ACCCGAATTCGATGACAGCAACCGTAGGATTG AGCCAA-3' (EcoRI site is underlined)
Antisense Primer [SEQ ID NO:22]:
 5'-CGCTGGATCCTCAAGCTGCCTGTTCCGCTAAGA T-3' (BamH-I site is underlined)
Region Cloned: Nucleotides 294–1580 of the Toxo P68 gene cloned into the EcoRI/BamH-I sites of pJO200 to yield plasmid pJO200-P68.
Step B: Construction and Immunoscreening of a Toxoplasma cDNA Library A Toxoplasma cDNA library was constructed in the UNIZAP XR vector using the Stratagene ZAP-cDNA Synthesis kit and ZAP-cDNA Gigapack II Gold Cloning kit. The cDNA produced in Example 2D was further processed using the kit protocols as briefly outlined below. The cDNA ends were blunted with T4 DNA polymerase, and EcoRI restriction site adapters were ligated to the blunt-ended cDNA. The RI adaptors ligated to the CDNA were then kinased with T4 Polynucleotide Kinase. The cDNA was digested with the restriction enzymes EcoRI and XhoI and then ligated to the phage lambda UNIZAP XR vector arms. The cDNA is cloned unidirectionally into this vector, resulting in the 5' end of the cDNA located downstream of the lacZ gene. If the coding sequence of the cDNA is in frame with the lacZ gene, a lacZ-Toxo fusion protein will be expressed. The UNIZAP XR-Toxo cDNA ligation mixture was packaged into phage in vitro, and a primary Toxoplasma cDNA phage library was obtained with 660,000 members. This library was amplified and checked for the size and frequency of the cloned cDNA inserts by converting a dozen random phage clones to E. coli phagemid (plasmid) clones using the Stratagene in vivo subcloning protocol from the ZAP-cDNA Synthesis kit. This procedure excises the cloned cDNA insert and the pBLUE-SCRIPT plasmid from the phage resulting in a pBLUE-SCRIPT plasmid clone containing the cloned cDNA. Miniprep DNA was made from the phagemid clones and analyzed with restriction enzymes on DNA agarose gels. Greater than 90% of the phagemid clones contained insert DNA with an average size of 0.8 Kb. This library was used for immunological screening with pooled plasma obtained from patients with Toxoplasmosis as described below.

Plasmas obtained from individuals in the acute phase of Toxoplasmosis infection were pooled. Samples used for this pool were tested by the Abbott IMx Toxo IgM and Toxo IgG immunoassays (Abbott Laboratories, Abbott Park, Ill.), and only samples that contained IgM antibodies and no detectable levels of IgG antibody were pooled. Prior to immunoscreening, the pooled plasma was treated to remove E. coli cross-reactive antibodies. The procedure followed was a modification of the protocol described in the Stratagene picoBLUE immunoscreening kit. Pooled plasma was initially diluted 1:5 in Rubazyme specimen dilution buffer and E. coli cross-reactive antibodies were removed by incubating the diluted pool plasma with several nitrocellulose filters coated with E. coli lysate as described in the kit protocol. After absorption of E. coli antibodies, the plasma pool was stored at 4° C. until further use.

The Toxoplasma cDNA library was immunologically screened following a modification of the Stratagene picoBLUE Immunoscreening kit protocol. Briefly, recombinant phage absorbed to the XL-1 Blue strain of E. coli were plated onto pre-warmed 150 mm NZY plates at a density of 20,000 phage per plate and incubated for 3.5 hrs. at 42° C. Duralose UV membranes pretreated with 10 mM IPTG and dried were then overlayed on each plate and incubated for an additional 4 hrs. at 37° C. The filters were oriented by piercing them with an 18 gauge needle, removed from the plate and washed 3x with TBST buffer at room temperature, 10 min. per wash. The filters were then washed once for 10 min. with TBS buffer at room temperature and blocked overnight at 4° C. in membrane blocking solution. The next day the filters were incubated for 2 hrs. at room temperature with the acute phase plasma pool (at 1:40 dilution in Rubazyme SDB). The filters were then washed 2x with TBST for 10 min. per wash and once with TBS for 10 min. and then incubated for 1 hr. at room temperature with goat anti-Human IgM (H+L) horseradish peroxidase-labelled antibody. The filters were washed again as before and developed for 10 min. in HRP color development solution. The filters were then extensively washed with tap water to stop the color development reaction, and plaques which gave a strong blue color were subsequently plaque purified twice and retested for immunoreactivity against the appropriate pool of plasma. Approximately 130,000 plaques were screened with the pooled acute phase plasma with the isolation of 4 positive clones. These phage clones were converted to plasmid clones using the Stratagene in vivo subcloning protocol from the ZAP-cDNA Synthesis Kit and further characterized as described below.

Step C: Characterization of the Immunopositive Clones Isolated With the Acute Phase Plasma Pool The 4 immunopositive clones isolated with the acute phase plasma pool were designated pGM610, pGM611, pGM612, and pGM613 and were analyzed with restriction enzymes on DNA agarose gels. Clones pGM610 and pGM612 contained a 1.1 Kb insert of DNA, clone pGM611 contained a 0.7 Kb insert of DNA, and clone pGM613 contained a 1.3 Kb insert of DNA. The cDNA inserts contained in these clones were removed from the pBLUESCRIPT vector by restriction enzyme digestion and purified on DNA agarose gels. These 4 purified cDNA inserts were individually labelled with alpha-$^{32}$P-dCTP using the Multiprime DNA labelling kit and protocol from Amersham for hybridization to colony filters and genomic Toxoplasma DNA. Filters for colony hybridization were prepared by gridding E. coli clones containing the cloned Toxoplasma genes described in Examples 3A and 3B onto Duralose UV membranes overlaid on LBamp plates. These plates- were grown overnite at 37° C., and the next day the E. coli colonies were lysed with alkali and prepared for DNA colony hybridization as described in GENERAL METHODS. After hybridization and washing, the hybridization signal was visualized by autoradiography with the result that all 4 immunopositive clones were homologous to one another and are non-homologous to the other 10 genes tested (see Example 3A). In order to determine the homology between the immunopositive clones and between Toxoplasma genomic DNA, the following Southern blot experiment was performed as described in GENERAL METHODS. Toxoplasma genomic DNA and two of the immunopositive clones were digested with restriction enzymes, run on DNA agarose gels, transferred to nitrocellulose and probed with purified radioactively-labelled cDNA inserts from clones pGM611 and pGM613. After hybridization and washing, the hybridization signal was visualized by autoradiography with the result that both clones were homologous to one another and all hybridized to the genomic blot of Toxoplasma DNA. Therefore, these 4 immunopositive clones contained the same Toxoplasma gene encoding a novel antigen which was designated $P_{novel2}$.

EXAMPLE 4

Construction of CKS-$P_{novel2}$ Expression Vector Based on pJO200

The gene encoding the $P_{novel2}$ antigen was subcloned into the pJO200 vector in order to produce adequate levels of fusion protein for further analysis. Since the reading frame of the lacZ gene in the pBLUESCRIPT vector and the reading frame of the CKS gene in the pJO200 vector are the same, presence of the EcoRI site at the juncture of the CKS and Toxoplasma genes ensured that the Toxoplasma gene was fused translationally in frame with the CKS gene. In order to remove the cDNA insert from the pBLUESCRIPT vector and subclone it into the pJO200 vector, the following digests were performed:

The CKS expression vector pJO200 described in Example 3A was digested with EcoRI and SmaI and the vector backbone was purified on an agarose gel in preparation for subcloning. Plasmid DNA from the largest $P_{novel2}$ clone pGM613 was digested with Asp718 and then treated with the Klenow fragment of DNA Polymerase I to render the ends blunt-ended. Subsequently, the DNA was extracted and then digested with EcoRI, and the 1.3Kb EcoRI/Asp718 (Klenow) DNA fragment from pGM613 was purified on an agarose gel and ligated to pJO200/EcoRI/SmaI overnight at 16° C.

The next day, the ligation mixture was transformed into competent XL-1 Blue cells. Miniprep DNA was prepared from the transformants and screened for the presence of the 1.3 Kb DNA fragment inserted at the EcoRI/SmaI sites of pJO200. The correct CKS-$P_{novel2}$ clone identified by restriction analysis was designated pJO200-$P_{novel2}$.

EXAMPLE 5

Expression of Recombinant Toxo Antigens and CKS in E. coli

Step A: Expression of cloned genes in E. coli

Bacterial clones pJO200-P22, pJO200-P24, pJO200-P25, pJO200-P28, pJO200-P30, pJO200-P35S, pJO200-P41, pJO200–66g, pJO200–68 and pJO200-$P_{novel2}$ expressing the CKS fusion proteins rpJO200-P22, rpJO200-P24, rpJO200-P25, rpJO200-P28, rpJO200-P30, rpJO200-P35S, rpJO200-P41, rpJO200-66g, rPJO200-68 and rpJO200-$P_{novel2}$ of Examples 3 and 4 and the control bacterial strain expressing unfused CKS were grown in "SUPERBROTH II" media containing 100 ug/ml ampicillin to log phase, and the synthesis of the CKS-Toxo fusion protein and unfused CKS was induced by the addition of IPTG as previously described (Robinson et al. (1993) J. Clin. Micro. 31, 629–635). After 4 hours post-induction, the cells were harvested, and the cell pellets were stored at −80° C. until protein purification occurred.

Step B: Purification of Recombinant Toxo Antigens and CKS Protein

Insoluble recombinant antigens rpJO200-P22, rpJO200-P25, rpJO200-P30, rpJO200-P35S, rpJO200-P41, rpJO200–66g, and rpJO200-$P_{novel2}$ were purified after lysis from cell paste by a combination of detergent washes followed by solubilization in 8M urea (Robinson et al. (1993) J. Clin. Micro. 31, 629–635). After solubilization was complete, these proteins were filtered through a 0.2 u filter and further purified by chromatography on SEPHACRYL S-300 columns. The appropriate column fractions were pooled for each protein and stored at 2–8° C. for evaluation by microtiter ELISA. Soluble rpJO200-P24, rpJO200-P28, rpJO200-P68, and unfused CKS proteins were purified after cell lysis by ammonium sulfate precipitation followed by ion-exchange chromatography. The appropriate column fractions were pooled for each protein, dialyzed against the appropriate buffer, and stored at 2–8° C. for evaluation by microtiter ELISA.

EXAMPLE 6

Evaluation of Human Sera with the Recombinant Toxo Antigens in Microtiter ELISA

Step A: Human Sera for Testing

The tests used for determining the presence of IgG and IgM antibody in sera were the Abbott Toxo-G and Toxo-M MEIA assays, respectively. Twenty-four Toxo IgG positive sera, eighteen Toxo IgM positive sera, and nineteen sera negative for Toxo IgG and IgM antibody were evaluated using the recombinant Toxo antigens in Microtiter ELISA.

Step B: Evaluation of Human Sera in the Recombinant Toxo Antigen Microtiter ELISA Purified recombinant Toxo antigens (Example 5B) were individually diluted to 5.0 ug per ml in PBS, and 0.1 ml of each antigen was added to separate wells of microtiter Maxisorp plates. Control wells for each sera were coated with E. coli lysate at 5.0 ug per ml. Plates were incubated at 37° C. for 1 hr and stored overnight at 4° C. The next day, the plates were washed three times with distilled water and blocked for 2 hrs at 37° C. with 0.2 ml of blocking solution (3% fish gelatin, 10% fetal calf serum in PBS, 0.22 u). The plates were then washed three times with distilled water and ready for incubation with serum. Each serum specimen was tested in duplicate with each antigen at a 1:200 dilution into Rubazyme SDB containing 2% E. coli lysate. After adding 0.1 ml of diluted specimen to each well, the plates were incubated for 1 hr. at 37° C. The plates were then washed three times with PBS-Tween and three times with distilled water. Bound human IgG and IgM were detected by using goat anti-human IgG-HRPO and IgM-HRPO conjugates, respectively, diluted 1:1,000 in Rubazyme conjugate diluent buffer and filtered. After addition of 0.1 ml of the appropriate diluted conjugate, the plates were incubated for 1 hr. at 37° C. and washed three times with PBS-Tween and three times with distilled water. The OPD color development reagent was prepared per manufacturer's directions and 0.1 ml was added to each well. After 2 minutes, the color development reaction was stopped by adding 0.1 ml of 1N sulfuric acid, and the plate was read in a microtiter plate reader. The net OD was obtained by subtracting the OD for the E. coli lysate-control from that of the test with each recombinant antigen. The cut-off for these assays was between 2 to 3 standard deviations from the mean of the negative population for each antigen.

The results of the evaluation of human sera in the recombinant microtiter ELISA are shown in Table 1 for detection of Toxoplasma-specific IgG antibody and in Table 2 for detection of Toxoplasma-specific IgM antibody. The performance of each antigen was ranked in decreasing order of the antigen with the largest number of positive specimen results per total number of positive (IgM or IgG) specimens tested.

TABLE 1

Relative rank of Antigen Performance in Microtiter IgG ELISA

| | Immunoreactivity | |
|---|---|---|
| Antigen | IgG⁻ # Pos Results/Total # IgG− Specimens Tested | IgG⁺ # Pos Results/Total # IgG+ Specimens Tested |
| P68 | 1/19 | 16/24 |
| P35S | 1/19 | 14/24 |
| P24 | 0/19 | 14/24 |
| P30 | 2/18 | 13/24 |
| Pnove12 (P29) | 1/19 | 13/24 |
| P22 | 0/19 | 13/24 |
| P30 | 2/18 | 13/24 |
| P41 | 0/19 | 10/24 |
| P25 | 1/19 | 10/24 |
| P28 | 1/19 | 10/24 |
| P66 | 2/19 | 9/24 |

TABLE 2

Relative rank of Antigen Performance in Microtiter IgM ELISA

| | Immunoreactivity | |
|---|---|---|
| Antigen | IgM⁻ # Pos Results/Total # IgM− Specimens | IgM⁺ # Pos Results/Total # IgM+ Specimens |
| P66 | 1/18 | 17/18 |
| P35 (1–135) | 0/18 | 15/18 |
| Pnove12 (P29) | 0/19 | 10/18 |
| P68 | 0/19 | 5/18 |
| P22 | 0/19 | 5/18 |
| P28 | 1/18 | 4/18 |
| P41 | 0/18 | 3/18 |
| P25 | 0/19 | 3/18 |

TABLE 2-continued

Relative rank of Antigen Performance in Microtiter IgM ELISA

| | Immunoreactivity | |
|---|---|---|
| Antigen | IgM⁻ # Pos Results/Total # IgM− Specimens | IgM⁺ # Pos Results/Total # IgM+ Specimens |
| P30 | 1/18 | 2/18 |
| P24 | 1/19 | 0/18 |

As can be seen from Table 1, there was no single recombinant Toxo antigen capable of detecting as positive all 24 IgG positive specimens. Hence, an immunoassay employing some combination of the antigens listed in Table 1 is required to detect all the IgG positive specimens.

As can be seen from Table 2, there was no single recombinant Toxo antigen capable of detecting as positive all 18 IgM positive specimens. Hence, an immunoassay employing some combination of the antigens listed in Table 2 is required to detect all the IgM positive specimens.

EXAMPLE 7

Generation of a Monoclonal Antibody Reactive With CKS-P$_{novel2}$ Antigen

Step A: Immune Response Study in Mice and Generation of Hybridomas

Animals, including mice, rats, hamsters, rabbits, goats and sheep may be infected with a lethal dose of tachyzoites, rescued from death with drug therapy and later used for hybridoma development. There are two hydbridoma development advantages for using this process that otherwise would not be possible. The first advantage is that time is allowed for a diverse repertoire of antibodies to be generated against native T. gondii (or Borrelia burgdorferi, Schistosoma sp., for example, Schistosoma treponema, or sporozoans other than T. gondii, for example, members of the genus Plasmodium (e.g., P. vivax and P. falciparum) and other possible members of the genus Toxoplasma)), and the second advantage is that the rescue allows time for affinity maturation of the immune response.

In the present experiment, Swiss mice were infected intraperitonally with $2.5 \times 10^7$ tachyozoites of T. gondii strain TS4. Five days later mice were treated orally with 10 mg pyrimethamine and 200 mg sulfamethoxazole per kg daily for 10 days. (This technique can be repeated every 6–8 weeks if desired.) After 12 additional weeks, these mice were injected intravenously with $1.2 \times 10^7$ sonicated tachyzoites 3 days prior to fusion to minimize the biohazardous status. One hundred percent of the mice survived (providing evidence of a humane method). Resulting hybrids from the PEG mediated fusion of splenocytes and the SP2/0 myeloma were screened on the sonicated tachyzoites and CKS-P$_{novel2}$ antigen (Kohler, G. and Milstein, C. (1975) Nature 256, 495–497; Kohler, G. and Milstein, C. (1976) Eur. J. Immunol. 6, 511–519; Goding, J. (1986) Monoclonal Antibodies: Principles and Practice. 2nd Ed. Academic Press London).

It should also be noted that monoclonal antibodies may be produced by immunizing mice by intraperitoneal infection with T. gondii (Mineo et al. (1993) J. Immunol. 150, 3951–3964; Handman et al. (1980) J. Immunol. 124, 2578–2583; Grimwood and Smith (1992) Exp. Parasitol. 74, 106–111) or with fractions of T. gondii (Prince et al. (1990) Mol. Biochem. Parasitol. 43, 97–106). Fusion of spleen cells and myeloma cells may then be carried out directly, subsequent to immunization, without a drug therapy step (see, e.g., Kohler and Milstein, supra (1975)).

Step B: Screening and Isolation of a Monoclonal Antibody to rpCKS-P$_{novel2}$

Bacterial clone pJO200-P$_{novel2}$ expressing the CKS-P$_{novel2}$ fusion protein of Example 4 (rpJO200-P$_{novel2}$) and the control bacterial strain expressing unfused CKS were grown in Superbroth II media containing 100 ug/ml ampicillin to log phase, and the synthesis of the CKS-Toxo fusion protein and unfused CKS was induced by the addition of IPTG as previously described in Example 5A. In preparation for screening hybridoma fluids obtained in Example 7A, cell pellets were thawed, resuspended in 10 ml of PBS and sonicated for 0.5 min in an icewater bath. The antigen preparation was diluted 1:40 in 0.05 M sodium carbonate-bicarbonate, pH 9.6, containing 15 mM sodium azide after which 0.1 ml of this suspension was placed in wells of NUNC MAXISORB microtiter plates. When tachyzoites were tested, $3 \times 10^6$ sonicated tachyzoites were added to wells. Plates were incubated at 37° C. for 1 hr, stored 1 to 3 days at 4° C., and washed three times with distilled water. Hybridoma fluids obtained in Example 7A were diluted 1:10 in Rubazyme SDB. The remainder of the ELISA was performed as described above in Example 6B except bound antibody was detected by mixture of horseradish peroxidase-conjugated goat anti-mouse IgG and IgM, each diluted to 1.0 ug per ml in Rubazyme conjugate diluent buffer.

Positive hybridoma clones were cloned by limiting dilution, and hybridoma fluid was retested by microtiter ELISA containing rpJO200-P$_{novel2}$, unfused CKS, and sonicated tachyzoites. One highly reactive monoclonal antibody clone was isolated which was designated Toxo Mab 5-241-178, which reacted very strongly with sonicated tachyzoites and rpJO200-P$_{novel2}$ but showed no reactivity to unfused CKS. This hybridoma clone was found to produce IgG type antibodies as determined using a mouse monoclonal antibody isotyping kit from Sigma.

Step C: Identification of the P$_{novel2}$ Gene Encoding the Toxoplasma P29 Antigen Using Toxo Mab 5-241-178

Total Toxoplasma protein prepared as described in Example 2C was loaded onto an 4–20% gradient Daiichi SDS-PAGE gel along with protein standard molecular weight markers, and transferred to nitrocellulose as described in General Methods. The Western blot was probed with the Toxo Mab 5-241-178 antibody, and the blot was visualized with a goat anti-mouse IgG-HRPO conjugate followed by BioRad Color Development Reagent (4-chloro-1-naphthol and hydrogen peroxide) per manufacturer's directions. A single protein band of 29,000 molecular weight from the Toxoplasma protein prepared from tachyzoites was immunoreactive with the Toxo Mab 5-241-178 indicating that the P$_{novel2}$ gene cloned in plasmid pGM613 (Example 3C) and pJO200-P$_{novel2}$ (Example 4) encodes the P29 antigen of Toxoplasma.

EXAMPLE 8

DNA Sequence of Clone pGM613 and Deduced Amino Acid Sequence

The 1.3 Kb EcoRI/XhoI insert of Toxoplasma cDNA contained in pGM613 was sequenced as described in General Methods. The DNA sequence (1268 bp) [SEQ ID NO:23] and the deduced amino acid sequence (228 aa) [SEQ ID NO:24] in-frame with the lacZ gene are shown in FIG. 1. The open reading frame (nucleotide position 2 to 685) present in this sequence can code for a protein of approximately 25,000 molecular weight. The first ATG present in the DNA sequence is located at nucleotide position 80 and is not surrounded by sequences fulfilling the criteria for initiation of translation (Kozak, M. (1986) Cell 44, 283–292) and is probably not the initiator methionine residue. Hence, it is likely that the insert of Toxoplasma cDNA present in clone pGM613 is not full-length.

Genebank's non-redundant protein, DNA, and dbEST/dbSTS sequences (tags) database and the Derwent DNA and protein patent databases were searched for homology to the DNA sequence and the deduced amino acid sequence of clone pGM613. Homology of DNA sequence and the deduced amino acid sequence was found between a portion of the pGM613 clone (nucleotide positions 461–684, amino acid residues 153–228) and the F29 clone of Knapp et al. contained in European Patent Application 0431541A2. In addition, homology between the DNA sequence of pGM613 and several T. gondii expressed sequence tags of unknown function isolated by Wan, K. -L. et al. (1996) Molec. and Biochem. Parasitol. 75, 179–186 was also found.

EXAMPLE 9

Isolation and Characterization of a Genomic Clone Containing the P29 Gene and Generation of a Composite DNA Sequence Since the cDNA insert of pGM613 encoding the P29 antigen of Toxoplasma appeared to be less than full-length, portion of the pGM613 cDNA sequence was used as a probe to isolate a genomic clone of the P29 antigen with the goal of cloning the remaining 5' end of the gene.

Step A: Construction of a Toxoplasma Genomic DNA Library in pJO200

A Toxoplasma genomic DNA library was constructed in the pJO200 vector as follows. Toxoplasma genomic DNA prepared in Example 2A was treated by a partial digestion with the restriction enzyme Sau 3AI as described in General Methods. The partially digested genomic DNA was subsequently electrophoresed on a 0.7% agarose gel with molecular weight standards and the 6–15 Kb molecular weight range of the DNA was isolated, purified, and extracted as described in General Methods. In preparation for ligation with the genomic DNA, plasmid pJO200 was digested with BamH-I followed by dephosphorylation with the CIAP enzyme. The resulting vector backbone was extracted and then ligated overnight at 16° C. with the Sau 3AI digested DNA. The ligation mixture was transformed the next day into competent XL-1 Blue cells, and the resulting transformants were pooled resulting in a primary Toxoplasma genomic library containing 80,000 members.

Step B: Screening Toxoplasma Genomic Library With P29 5' Gene Probe

In order to isolate the 5' end of the P29 gene from the genomic library, a portion of the 5' end of the cDNA clone present in pGM613 was selected as a probe. This portion of the cDNA was then used to probe the Toxoplasma genomic library prepared in Example 9A for genomic clones homologous to the 5' end of the cDNA.

Plasmid pGM613 was digested with SacII and HindIII, and the 326 bp SacII/HindIII fragment containing the 5' end of the cDNA insert in pGM613 (nucleotide positions 55–380, see FIG. 1) was gel purified. This gene fragment was radioactively labelled and used to probe the Toxoplasma genomic library by colony hybridization as described in General Methods. Positive clones obtained by hybridization were colony purified and retested. One positive clone designated pTXG1-2 containing a 6.5 Kb insert of DNA was further characterized as described below.

Step C: DNA Sequence of Genomic Clone pTXG1-2 and Composite DNA Sequence for the P29 Gene and the Deduced Amino Acid Sequence The 5' end of the P29 gene contained in clone pTXG-12 was sequenced as described in General Methods using DNA primers complementary to the 5' end of the cDNA contained in clone pGM613. The DNA sequence obtained for clone pTXG1-2 [SEQ ID NO:25] is shown in FIG. 2. An alignment of the DNA sequences for genomic clone pTXG-1 and the CDNA clone pGM613 was then performed resulting in the composite DNA sequence [SEQ ID NO:26] and deduced amino acid sequence [SEQ ID NO:27] for the P29 gene as shown in FIG. 3. The composite DNA sequence is derived from the genomic sequence of clone pTXG-1 (FIG. 2, [SEQ ID NO:25]) and the cDNA sequence of pGM613 (FIG. 1, [SEQ ID NO:23]) as shown below in Table 3.

TABLE 3

Source of Sequence for the Composite DNA Sequence for the P29 Gene

| Nucleotide Position Composite Sequence | Nucleotide Position Genomic Sequence | Nucleotide Position cDNA Sequence |
|---|---|---|
| 1–419 | 1–419 | None |
| 420–477 | 420–477 | 40–97 |
| 478–1648 | None | 98–1268 |

The only good candidate for the initiator methionine residue for the start of translation of the P29 gene is the first methionine shown on FIG. 3 starting at nucleotide position 358. This is the only methionine in-frame with the reading frame present in the cDNA clone pGM613. If the same reading frame is examined further upstream of the methionine at position 358, no further methionine residues are found before an in-frame UAA stop codon present at position 325. The methionine at nucleotide position 358 is surrounded by sequences fulfilling the criteria for initiation of translation (Kozak, M. (1986) Cell 44, 283–292) and is followed by amino acid residues that constitute a signal peptide (von Heijne, G. (1986) Nucleic Acids Res. 14, 4683–4690).

EXAMPLE 10
Construction of an Improved CKS Epitope-Embedding Vector pEE3

The CKS epitope-embedding expression vector pEE1 described in U.S. patent application Ser. No. 08/742,619 of Maine and Chovan allows for the embedded fusion of recombinant proteins to the CMP-KDO synthetase (CKS) protein. In order to facilitate the cloning of the P29 gene into the CKS epitope-embedding vector, the pEE1 vector was modified in two steps. First, an obsolete polylinker near the 3' end of the CKS gene in the pEE1 vector was removed generating an intermediate vector pEE2. Secondly, a new polylinker was introduced into the coding region of CKS, thus permitting the embedding of genes using a variety of restriction sites (StuI, EcoRI, SacI, BamH-I, PstI, MluI) into the CKS gene.

Step A: Construction of pEE2
The plasmid pEE2, a derivative of the CKS expression vector pEE1 (FIG. 4A), was constructed by digesting pEE1 with the Bgl II restriction enzyme and removing a polylinker located at the 3' end of the CKS gene which had the sequence (5'-3') [SEQ ID NO:28] (FIG. 4B) and the deduced amino acid sequence [SEQ ID NO:49]

AGATCTCGACCCGTCGACGAATTC-GAGCTCGGTACCCGGGGATCCTCTAGAC AspLeuAspProSerThrAsnSerS-erSerValProGlyAspProLeuAsp

TGCAGGCATGCTAAGTAAGTAGATCT CysArgHis-AlaLys and replacing it with the following sequence (5'-3') [SEQ ID NO:29] (see FIG. 4C) and the deduced amino acid sequence [SEQ ID NO:50]

AGATCTCGACCCATCTACCAATTCGTCT-TCTGTTCCGGGTGATCCGCTAGAC AspLeuAsp-ProSerThrAsnserserservalProGlyAspProLeuAsp TGCCGTCACGCTAAGTAAGTAGATCT CysArgHis-AlaLys.

As shown in FIGS. 4B and 4C, this sequence replacement removes the restriction sites SalI, EcoRI, SacI, KpnI, SmaI, BamH-I, XbaI, PstI, and SphI, thus enabling the use of these sites in a new polylinker to be embedded later within the CKS gene further upstream (Example 10B).

Plasmid pEE1 was digested with Bgl II and then treated with the CIAP enzyme to remove the 5' phosphate groups to prevent self-ligation. The pEE1/Bgl II dephoshorylated vector backbone was then purified on an agarose gel. Two oligonucleotides shown below (5'-3') were synthesized for ligation into the pEE1/Bgl II backbone.

[SEQ ID NO:30]

CCTGAAGATCTCGACCCATCTACCAATTCGTCTTCTGTTCCGGGTGATCC

GCTAGACTGCCGTCACGCTAAGTAAGTAGATCTTGACT

[SEQ ID NO:31]

AGTCAAGATCTACTTACTTAGCGTGACGGCAGTCTAGCGGATCACCCGGA

ACAGAAGACGAATTGGTAGATGGGTCGAGATCTTCAGG

These oligonucleotides were mixed together, heated to 85° C. and then allowed to cool gradually overnight to 4° C. to permit annealing of the oligonucleotides. The annealed oligonucleotides were then digested with the Bgl II enzyme, extracted, and then ligated to the pEE1/Bgl II backbone overnight at 16° C. The ligation mixture was transformed the next day into competent XL-1 Blue cells. Miniprep DNA was prepared from the transformants and screened for the presence of the new sequence by restriction enzyme analysis. Putative correct clones were then sequenced to verify the correct sequence in the proper orientation. Plasmid pEE2 was isolated which contains the new sequence [SEQ ID NO:29] at the Bgl II site.

Step B: Construction of pEE3
The plasmid pEE3, a derivative of the CKS expression vector pEE2 (FIG. 5A), was constructed by digesting pEE2 with StuI and MluI and cloning in a new polylinker with the following sequence (5'-3') [SEQ ID NO:32](see FIG. 5B) and deduced amino acid sequence [SEQ ID NO:51]

AGGCCTGAATTCGAGCTCTGGGATC-CGTCTGCAGACGCGT GlyLeuAsnSerSerSerGlyIle-ArgLeuGlnThrArg which contains the restriction sites StuI, EcoRI, SacI, BamH-I, PstI, and MluI.

Plasmid pEE2 was digested with StuI and MluI, and the vector backbone was purified on an agarose gel. Two oligonucleotides shown below (5'-3') were synthesized for ligation into the pEE2/StuI/MluI 30 backbone.

[SEQ ID NO:33]

CCTGAATTCGAGCTCTGGGATCCGTCTGCAGA

[SEQ ID NO:34]

CGCGTCTGCAGACGGATCCCAGAGCTCGAATTCAGG

These oligonucleotides were mixed together, heated to 80° C. for 10 minutes and then allowed to cool gradually overnight to 4° C. to permit annealing of the oligonucleotides. The annealed oligonucleotides were then ligated to the pEE2/StuI/MluI backbone overnight at 16° C. The ligation mixture was transformed the next day into competent XL-1 Blue cells. Miniprep DNA was prepared from the transformants and screened for the presence of the new sequence by restriction enzyme analysis. Putative correct clones were then sequenced to verify the correct sequence. Plasmid pEE3 was isolated which contains the new sequence [SEQ ID NO:32] at the StuI/MluI sites.

EXAMPLE 11

Construction of CKS-Toxo Ag-CKS Epitope-Embedding Expression Vectors

The CKS expression vectors pJO200, pEE1, and pEE3 were utilized for the construction of four CKS-Toxo Ag-CKS gene fusion constructs using the Toxo P29, P30, P35, and P66 genes.

Step A: Construction of pToxo-P29: CKS-P29(1-236aa)-CKS

Figure 6:
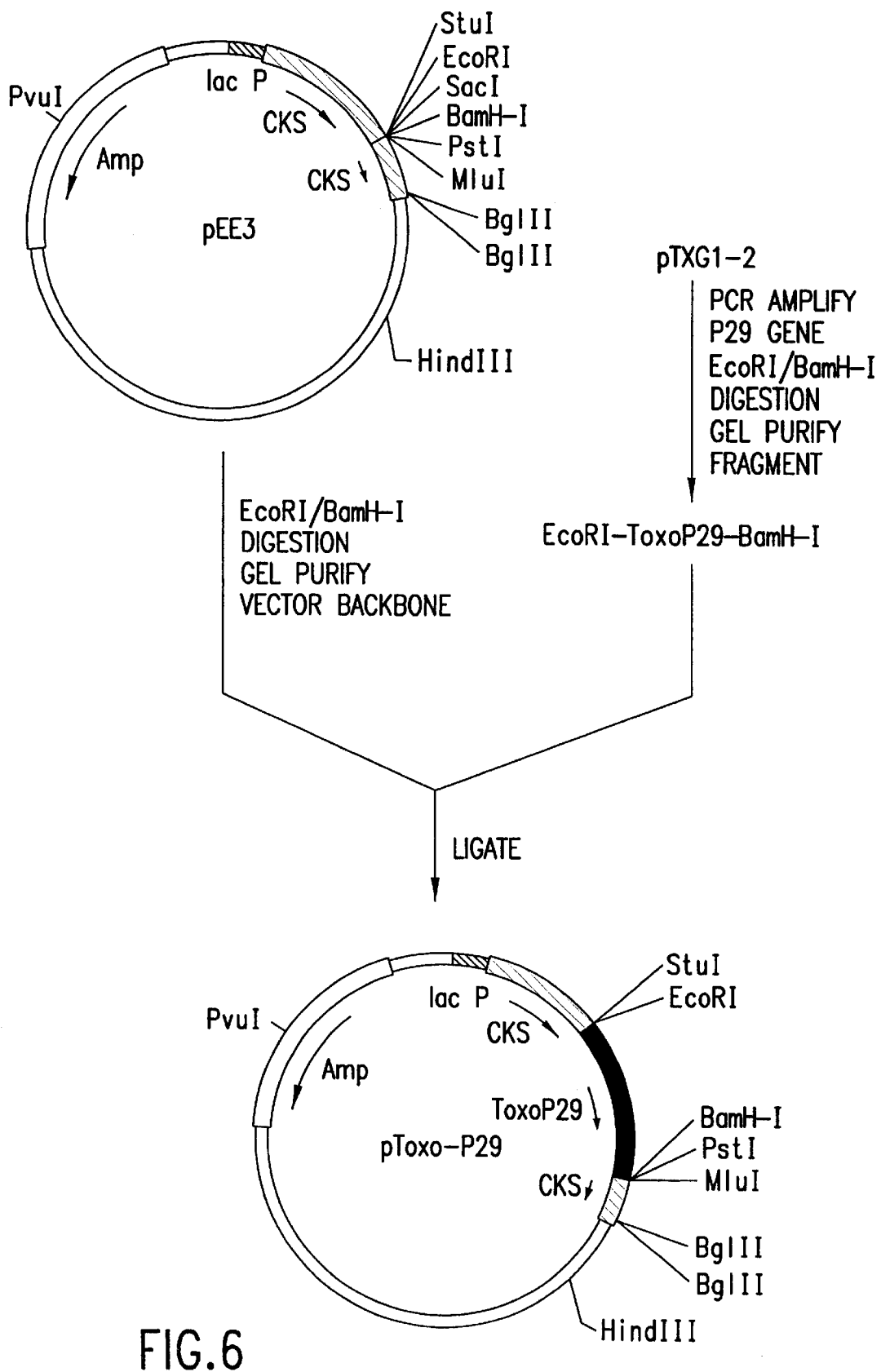
FIG. 6 is a schematic representation of the construction of plasmid pToxo-P29.

The plasmid pToxo-P29, a derivative of plasmid pEE3 (FIG. 6), was constructed by cloning a DNA fragment containing Toxo P29, obtained by PCR amplification of Toxo P29 DNA contained in plasmid pTXG1-2 (Example 9C), into the EcoRI/BamH-I sites of pEE3. Plasmid pToxo-P29 was deposited with the ATCC 10801 University Boulevard, Manassas, Va. 20110-2209, under the terms of the Budapest Treaty on May 19, 1998, and was accorded Accession No. ATCC 98758.

Large scale plasmid DNAs (pTXG1-2 and pEE3) were isolated by general methods. Plasmid pEE3 was digested with EcoRI and BamH-I, and the vector backbone, pEE3/EcoRI/BamH-I, was purified on an agarose gel. A sense primer, starting at nucleotide 358 of the P29 gene (FIG. 3) containing an EcoRI site, and an antisense primer containing a BamH-I site, starting at nucleotide 1065 of the P29 gene, were synthesized as shown below:

Sense Primer [SEQ ID NO:35]
   5'-ACTTAGAATTCGATGGCCCGACACGCAATTTT TCC-3' (EcoRI site is underlined)
Antisense Primer [SEQ ID NO:36]
   5'-ACATGGATCCGCTGGCGGGCATCCTCCCCATCT TC-3' (BamH-I site is underlined)

The sense and antisense primers were added to a PCR reaction mixture containing plasmid pTXG1-2. After PCR amplification, the reaction mixture was digested with EcoRI and BamH-I, and the 708 base pair DNA fragment containing P29 was purified on an agarose gel. The purified 708 base pair DNA fragment was ligated to pEE3/EcoRI/BamH-I overnight at 16° C. The ligation mixture was transformed the next day into competent XL-1 Blue cells. Miniprep DNA was prepared from the transformants and screened for the presence of the P29 DNA sequence by restriction enzyme analysis. Plasmid pToxo-P29 contained the P29 gene embedded at the EcoRI/BamH-I sites of pEE3. This CKS-ToxoP29-CKS fusion construct was designated:

"CKS (1-171aa)-N-S-ToxoP29(1-236aa)-R-I -R-L-Q-T-R-CKS(171-260aa)"

where N, S, R, I, R, L, Q, T, R are the asparagine, serine, arginine, isoleucine, arginine, leucine, glutamine, threonine, and arginine residues, respectively, encoded by the polylinker DNA sequence of the vector. The complete DNA sequence [SEQ ID NO:37] of plasmid pToxo-P29 and the corresponding amino acid sequence [SEQ ID NO:52] of the CKS-P29-CKS fusion protein is shown in FIG. 7, wherein amino acid residues 174–409 of SEQ ID NO:52 correspond to the full length amino acid sequence of the P29 antigen of *Toxoplasma gondii*.

Step B: Construction of pToxo-P30:CKS-P30(1-236aa)-CKS

Figure 8:
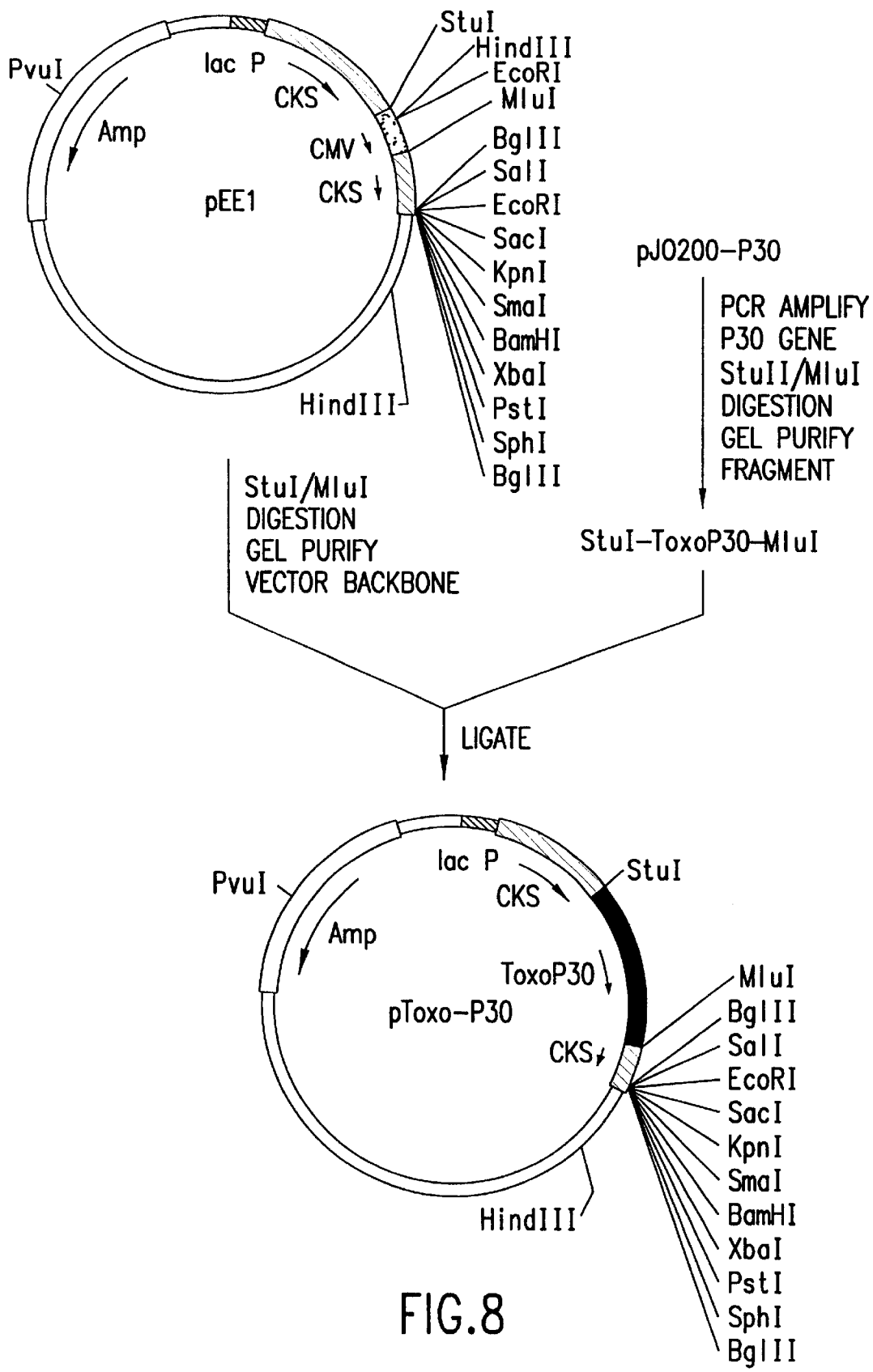
FIG. 8 is a schematic representation of the construction of plasmid pToxo-P30.

The plasmid pToxo-P30, a derivative of plasmid pEE1 (FIG. 8), was constructed by cloning a DNA fragment containing Toxo P30, obtained by PCR amplification of Toxo P30 DNA contained in plasmid pJO200-P30 (Example 3A), into the StuI/MluI sites of pEE1. Plasmid pToxo-P30 was deposited with the ATCC 10801 University Boulevard, Manassas, Va. 20110-2209, under the terms of the Budapest Treaty on May 19, 1998, and was accorded Acession No. ATCC 98761.

Large scale plasmid DNAs (pJO200-P30 and pEE1) were isolated by general methods. Plasmid pEE1 was digested with StuI and MluI, and the vector backbone, pEE1/StuI/MluI, was purifed on an agarose gel. A sense primer, starting at nucleotide 464 of the P30 gene containing an StuI site, and an antisense primer containing a MluI site, starting at nucleotide 1318 of the P30 gene (Burg et al. (1988) J. Immunol. 141, 3584–3591) were synthesized as shown below:

Sense Primer [SEQ ID NO:38]
   5'-TCCTAGGCCTTAATTCGATGCTTGTTGCCAATCA AG- 3' (StuI site is underlined)
Antisense Primer [SEQ ID NO:39]
   5'-ACATACGCGTCGCGACACAAGCTGCGATAGAG-3' (MluI site is underlined)

The sense and antisense primers were added to a PCR reaction mixture containing plasmid pJO200-P30. After PCR amplification, the reaction mixture was digested with StuI and MluI, and the 855 base pair DNA fragment containing P30 was purified on an agarose gel. The purified 855 base pair DNA fragment was ligated to pEE1/StuI/MluI overnight at 16° C. The ligation mixture was transformed the next day into competent XL-1 Blue cells. Miniprep DNA was prepared from the transformants and screened for the presence of the P30 DNA sequence by restriction enzyme analysis. Plasmid pToxo-P30 contained the P30 gene embedded at the StuI/MluI sites of pEE1. This CKS-ToxoP30-CKS fusion construct was designated:

"CKS(1-171aa)-N-S-M-ToxoP30(5-289aa)-T-R-CKS (171-260aa)"

where N, S, M, T, R are the asparagine, serine, methionine, threonine, and arginine residues, respectively, encoded by the synthetic DNA sequence of the vector. The complete DNA sequence [SEQ ID NO:40] of plasmid pToxo-P30 is shown in FIG. 9 and the corresponding amino acid sequence [SEQ ID NO:53] of the CKS-P30-CKS fusion protein are shown in FIG. 9, wherein amino acid residues 175–459 of SEQ ID NO:53 correspond to amino acids 5–289 of the P30 antigen of *Toxoplasma gondii*.

Step C: Construction of pToxo-P35S:CKS-P35(1-135aa)-CKS

Figure 10:
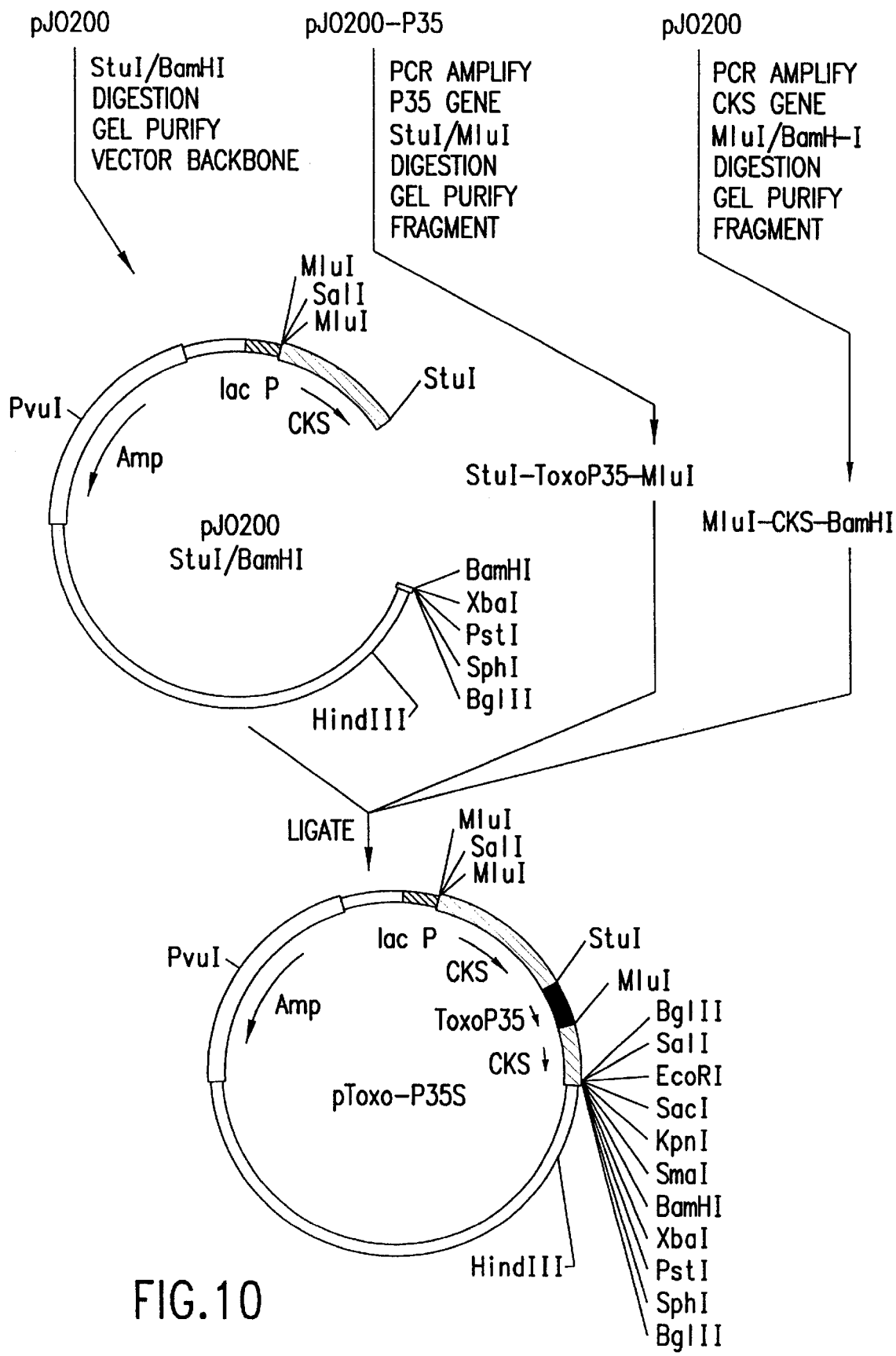
FIG. 10 is a schematic representation of the construction of plasmid pToxo-P35S.

The plasmid pToxo-P35S, a derivative of plasmid pJO200 (FIG. 10), was constructed by cloning a DNA fragment containing Toxo P35, obtained by PCR amplification of Toxo P35 DNA contained in plasmid pJO200-P35 (Example 3A), into the StuI site of pJO200. Plasmid pToxo-P35S was deposited with the ATCC 10802 University Boulevard, Manassas, Va. 20110-2209, under the terms of the Budapest Treaty on May 19, 1998, and was accorded Accession No. ATCC 98759.

Large scale plasmid DNAs (pJO200-P35 and pJO200) were isolated by general methods. Plasmid pJO200 was digested with StuI and BamH-I, and the vector backbone, pJO200/StuI/BamH-I, was purified on an agarose gel. A sense primer, starting at nucleotide 91 of the P35 gene containing an StuI site, and an antisense primer containing a MluI site, starting at nucleotide 495 of the P35 gene (Knapp et al., 1989 (EPA 431541A2)) were synthesized as shown below:

Sense Primer [SEQ ID NO:41]

5'-GAGCAGAAGGCCTTATGAACGGTCCTTTGAGT TATCATCC-3' (StuI site is underlined)

Antisense Primer [SEQ ID NO:42]

5'-TTCGCTCACGCGTATGGTGAACTGCCGGTATC T-3' (MluI site is underlined)

The sense and antisense primers were added to a PCR reaction mixture containing plasmid pJO200-P35. After PCR amplification, the reaction mixture was digested with StuI and MluI, and the 405 base pair DNA fragment containing P35 was purified on an agarose gel. A sense primer, starting at nucleotide 640 of pJO200 containing an MluI site, and an antisense primer starting at nucleotide 905 of pJO200 were synthesized as shown below:

Sense Primer [SEQ ID NO:43]

5'-GACGGAGACGCGTCTTGAACCGTTGGCGATA ACT-3' (MluI site is underlined)

Antisense Primer [SEQ ID NO:44]

5'-GCATGCCTGCAGTCTAGAGGA-3'

The sense and antisense primers were added to a PCR reaction mixture containing plasmid pJO200. After PCR amplification, the reaction mixture was digested with MluI and BamH-I, and the 266 base pair DNA fragment containing P35 was purified on an agarose gel.

The purified 405 base pair DNA fragment containing the P35 gene and the purified 266 base pair DNA fragment containing the 3' end of the CKS gene, were ligated to pJO200/StuI/BamH-I overnight at 16° C. The ligation mixture was transformed the next day into competent XL-1 Blue cells. Miniprep DNA was prepared from the transformants and screened for the presence of the P35 DNA sequence by restriction enzyme analysis. Plasmid pToxo-P35S contained the P35 gene embedded at the StuI/MluI sites of pJO200. This CKS-ToxoP35-CKS fusion construct was designated:

"CKS(1-171aa)-ToxoP35(1-135aa)-T-R-CKS(171-260aa)"

where T and R are the threonine and arginine residues, respectively, encoded by the synthetic DNA sequence of the vector. The complete DNA sequence [SEQ ID NO:45] of plasmid pToxo-P35S and the corresponding amino acid sequence [SEQ ID NO:54] of the CKS-P35-CKS fusion protein are shown in FIG. 11, wherein amino acid residues 172–306 of SEQ ID NO:54 correspond to amino acids 1–135 of the P35 antigen of *Toxoplasma gondii*.

Step D: Construction of pToxo-P66g:

CKS-P66(26-428aa)-CKS

Figure 12:
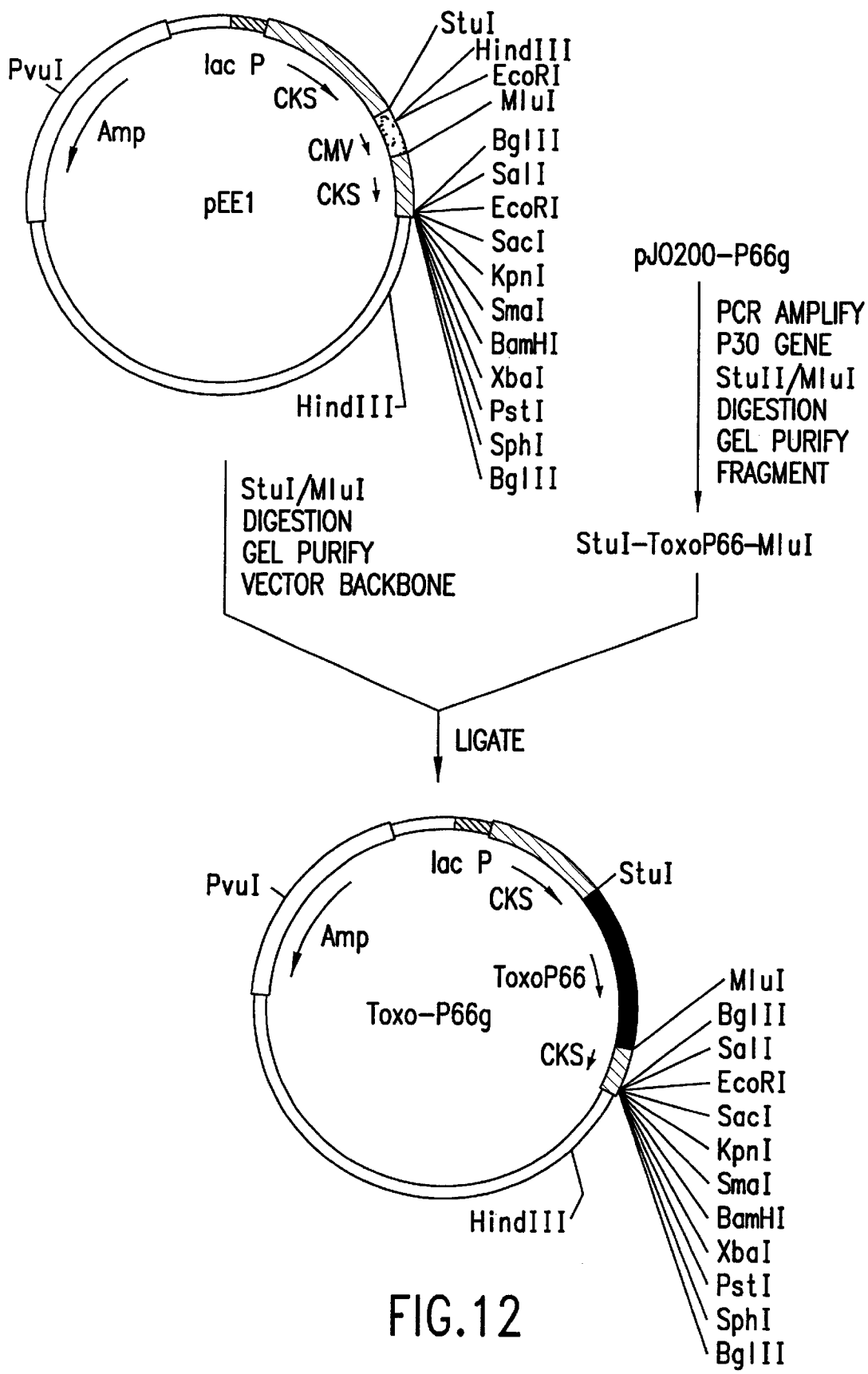
FIG. 12 is a schematic representation of the construction of plasmid pToxo-P66g.

The plasmid pToxo-66g, a derivative of plasmid pEE1 (FIG. 12), was constructed by cloning a DNA fragment containing Toxo P66, obtained by PCR amplification of Toxo P66 DNA contained in plasmid pJO200-P66g (Example 3A), into the StuI/MluI sites of pEE1. Plasmid pToxo-P66g was deposited with the ATCC 10801 University Boulevard, Manassas, Va. 20110-2209, under the terms of the Budapest Treaty on May 19, 1998, and was accorded Accession No. ATCC 98760.

Large scale plasmid DNAs (pJO200-P66g and pEE1) were isolated by general methods. Plasmid pEE1 was digested with StuI and MluI, and the vector backbone, pEE1/StuI/MluI, was purified on an agarose gel. A sense primer, starting at nucleotide 122 of the P30 gene containing an StuI site, and an antisense primer containing a MluI site, starting at nucleotide 1330 of the P66 gene (Knapp et al., supra (1989)) were synthesized as shown below:

Sense Primer [SEQ ID NO:46]

5'-ATATTAGGCCTTATGAGCCACAATGGAGTCCC CGCTTATCC-3' (StuI site is underlined)

Antisense Primer [SEQ ID NO:47]

5'-CAGTGTACGCGTTTGCGATCCATCATCCTGC TCTCTTC-3' (MluI site is underlined)

The sense and antisense primers were added to a PCR reaction mixture containing plasmid pJO200-P66g. After PCR amplification, the reaction mixture was digested with StuI and MluI, and the 1209 base pair DNA fragment containing P66 was purified on an agarose gel. The purified 1209 base pair DNA fragment was ligated to pEE1/StuI/MluI overnight at 16° C. The ligation mixture was transformed the next day into competent XL-1 Blue cells. Miniprep DNA was prepared from the transformants and screened for the presence of the P66 DNA sequence by restriction enzyme analysis. Plasmid pToxo-P66g contained the P66 gene embedded at the StuI/MluI sites of pEE1. This CKS-ToxoP66-CKS fusion construct was designated:

"CKS (1-171aa)-M-ToxoP66(26-428aa)-T-R-CKS (171-260aa)"

where M, T, and R are the methionine, threonine and arginine residues, respectively, encoded by the synthetic DNA sequence of the vector. The complete DNA sequence [SEQ ID NO:48] of plasmid pToxo-P66g and the corresponding amino acid sequence [SEQ ID NO:55] of the CKS-P66-CKS fusion protein are shown in FIG. 13, wherein amino acid residues 173–575 of SEQ ID NO:55 correspond to amino acids 26–428 of the P66 antigen of *Toxoplasma gondii*.

EXAMPLE 12

Development of a Toxo Recombinant Antigen Cocktail for the Detection of Toxoplasma-Specific IgG and IgM The results in Tables 1 and 2 of Example 6B indicated that more than one recombinant antigen would be required to detect Toxoplasma-specific IgG and IgM in order to replace the tachyzoite in an immunoassay. Additional sera were sourced from patients with an acute or chronic Toxolasmosis and tested with the individual antigens coated in separate wells listed in Tables 1 and 2 using the IgG or IgM Microtiter ELISA described in Example 6B. These results indicated that a cocktail of recombinant antigens necessary and sufficient to replace the tachyzoite in an immunoassay should be composed of the following Toxo antigens:

Toxo IgG Immunoassay: P29+P30+P35
Toxo IgM Immunoassay: P29+P35+P66

In order to demonstrate the diagnostic utility of the Toxo recombinant antigens in the proposed above combinations in an immunoassay, i.e. the coating of the Toxo antigens P29, P30, and P35 in a single microtiter plate well (Microtiter format) or other solid phase, e.g. microparticles (MEIA format), to detect Toxoplasma-specific IgG antibodies and the coating of the Toxo antigens P29, P35, and P66 in a single microtiter plate well (Microtiter format) or other solid phase, e.g. microparticles (MEIA format), to detect Toxoplasma-specific IgM antibodies, the following experiments were performed:

Step A: Expression of cloned genes in *E. coli*

Bacterial clones pToxo-P29, pToxo-P30, pToxo-P35S, and pToxo-P66g expressing the CKS fusion proteins rpToxo-P29, rpToxo-P30, rpToxo-P35S, and rpToxo-P66g, respectively, were grown in SUPERBROTH II media containing 100 ug/ml ampicillin to log phase, and the synthesis of the CKS-Toxo fusion protein was induced by the addition of IPTG as previously described (Robinson et al. (1993) J. Clin. Micro. 31, 629–635). After 4 hours post-induction, the cells were harvested, and the cell pellets were stored at −80° C. until protein purification.

Step B: Purification of Recombinant Toxo Antigens

Insoluble recombinant antigens rpToxo-P29, rpToxo-P30, rpToxo-P35S, and rpToxo-P66g were purified after lysis from cell paste by a combination of detergent washes followed by solubilization in 8M urea (Robinson et al., supra (1993)). After solubilization was complete, these proteins were filtered through a 0.2 m filter and either stored at 2–8° C. (w/urea) or dialyzed against 50 mM Tris, pH 8.5 and then stored at 2–8° C. (w/o urea).

Step C: Human Sera for Testing

Four groups of serum specimens from a French population were evaluated for the presence of Toxoplasma-specific IgG and IgM antibodies using the Microtiter ELISA. These serum specimens collectively cover the entire span of Toxoplasma infection from early seroconversion (acute toxoplasmosis) to convalesence (latent infection, chronic toxoplasmosis) and represent the types of specimens normally encountered in routine Toxoplasma serology.

Group 1: Negative Serum Specimens

This group contained 200 serum specimens negative for Toxoplasma IgG and IgM antibodies as determined by the Abbott IMx Toxo IgG and IgM immunoassays.

Group 2: "Ancienne" Serum Specimens

This group contained 100 serum specimens negative for Toxoplasma IgM antibodies and positive for Toxoplasma IgG antibodies by the Abbott IMx Toxo IgG and IgM immunoassays. These specimens were negative for Toxoplasma IgA antibodies as determined by an immunocapture assay using a suspension of tachyzoites (IC-A) (Pinon, J. M. (1986) Diag. Immunol. 4:223–227).

Group 3: "Evolutive" Serum Specimens

This group contained 99 serum specimens positive for Toxoplasma IgG antibodies by a high sensitivity direct agglutination assay (HSDA) (Desmonts, G. and Remington, J. S. (1980) J. Clin. Micro. 11:562–568) and positive for Toxoplasma IgM and IgA antibodies using a specific immunocapture assay (IC-M, IC-A).

Group 4: "Precoce" Serum Specimens

This group contained 66 specimens sourced from individuals with evidence of a early seroconversion of Toxoplasma-specific antibodies (absence or early manifestation of IgG antibodies and positive for IgM and IgA antibodies using a specific immunocapture assay (IC-M, IC-A)).

Step D: Evaluation of Human Sera in the Recombinant Toxo Antigen Microtiter ELISA Purified recombinant Toxo antigens (Example 12B) were coated onto the wells of the microtiter plate as follows:

For the IgG microtiter ELISA, the three Toxo antigens rpToxo-P29, rpToxo-P30, and rpToxo-P35S (w or w/o urea) were diluted together into PBS to a final concentration of 5 ug/ml for each antigen, and plates were coated and processed as described in Example 6B using a goat anti-human IgG-HRPO conjugate to detect bound human IgG. All three Toxo antigens were coated together into the same microtiter well to detect Toxoplasma-specific IgG. For the IgM microtiter ELISA, the three Toxo antigens rpToxo-P29, rpToxo-P35S, and rpToxo-P66g (w or w/o urea) were diluted together into PBS to a final concentration of 5 mg/ml for each antigen, and plates were coated and processed as described in Example 6B using a goat anti-human IgM-HRPO conjugate to detect bound human IgM. All three Toxo antigens were coated together into the same microtiter well to detect Toxoplasma-specific IgM. The cut-off for these assays was between 2 to 3 standard deviations from the mean of the negative population.

Step E: Results of the Evaluation of Human Sera in the Recombinant Toxo Antigen (P29+P30+P35) IgG Microtiter ELISA The serum specimens from Groups 1–4 (Example 12C) were tested for the presence of Toxoplasma-specific IgG using the recombinant Toxo antigen IgG microtiter ELISA (rpToxo-P29 (P29)+rpToxo-P30 (P30)+rpToxo-P35S (P35)). The results from this evaluation are presented in Tables 4–8.

TABLE 4

Evaluation of Group 1 Negative Serum Specimens by Toxo IgG Microtiter ELISA

| | | Abbott IMx Toxo IgG | |
|---|---|---|---|
| | | Pos | Neg |
| Toxo IgG (P29 + P30 + P35) Microtiter ELISA | Pos | 0 | 8 |
| | Neg | 0 | 192 |
| Specificity: | 192/200 = 96% | | |

TABLE 5

Evaluation of Group 2 "Ancienne" Serum Specimens by Toxo IgG Microtiter ELISA

| | | Abbott IMx Toxo IgG | |
|---|---|---|---|
| | | Pos | Neg |
| Toxo IgG (P29 + P30 + P35) Microtiter ELISA | Pos | 97 | 0 |
| | Neg | 3 | 0 |
| Sensitivity: | 97/100 = 97% | | |

TABLE 6

Evaluation of Group 3 "Évolutive" Serum Specimens by Toxo IgG Microtiter ELISA

| | | HSDA IgG | |
|---|---|---|---|
| | | Pos | Neg |
| Toxo IgG (P29 + P30 + P35) Microtiter ELISA | Pos | 99 | 0 |
| | Neg | 0 | 0 |
| Sensitivity: | 99/99 = 100% | | |

TABLE 7

Evaluation of Group 4 "Précoce" Serum Specimens by Toxo IgG Microtiter ELISA

|  |  | HSDA IgG | |
| --- | --- | --- | --- |
|  |  | Pos | Neg |
| Toxo IgG (P29 + P30 + P35) Microtiter ELISA | Pos | 54 | 1 |
|  | Neg | 1 | 10 |

Sensitivity: 54/55 = 98.1%

TABLE 8

Summary of Evaluation of Groups 1–4 Serum Specimens by Toxo IgG Microtiter ELISA

|  |  | Reference Test | |
| --- | --- | --- | --- |
|  |  | Pos | Neg |
| Toxo IgG (P29 + P30 + P35) Microtiter ELISA | Pos | 250 | 9 |
|  | Neg | 4 | 202 |

Specificity: 202/211 = 95.7%
Sensitivity: 250/254 = 98.4%

As can be seen from Tables 4–8, the Toxo IgG microtiter ELISA is both a sensitive and specific assay for the detection of Toxoplasma-specific IgG as demonstrated by the overall high relative diagnostic specificity (95.7%) and sensitivity (98.4%) (Table 8) of the assay. The Toxo recombinant antigen cocktail comprised of the Toxo antigens P29, P30 and P35, in combination with the Toxo IgG assay, is both necessary and sufficient to replace the tachyzoite for the detection of Toxoplasma-specific IgG antibody.

Furthermore, there are several advantages of the recombinant antigen cocktail over the tachyzoite antigen for use in detection of IgG antibodies. First, the antigens are purified, and the amount of each antigen loaded into the immunoassay can be accurately determined and standardized, e.g., protein concentration. This minimizes interlot differences commonly observed in kits manufactured with different tachyzoite antigen lots. Hence, different lots of kits manufactured with different antigen cocktail lots will be very consistent from lot to lot. Secondly, mouse monoclonal antibodies to the individual recombinant Toxo antigens are used to monitor coating of the proteins to the solid phase. This further ensures that each lot produced is consistent. Third, the true clinical sensitivity of the assay using the purified antigens will be higher by virtue of the fact of the higher specific activity of the purified antigens. Finally, kits manufactured with the antigen cocktail are more stable during storage over time, and the performance of the assay using these antigens remains consistent over the shelf life of the assay. Kits manufactured with the tachyzoite antigen are not as stable and their performance may vary over time.

Additionally, there are many advantages of using a cocktail over using a single antigen alone. For example, an immune response to infection varies by individual. Some individuals produce antibodies to P35 and not to P66, whereas some individuals produce antibodies to P66 and not to P35. Thus, the antigen cocktail of the present invention will detect both groups of individuals.

Moreover, immune responses vary with time. For example. One individual may produce antibodies against P35 first and then later produce antibodies to only P66. Thus, the present cocktail will detect both types of "positive" individuals.

Furthermore, individuals may be infected with different Toxo serotypes, strains or isolates. Thus, the immune response may be such that multiple antigens are needed to detect the presence of all antibodies being produced. Again, the present cocktail allows for such detection.

Also, it is known from previous Western Blot experiments with tachyzoite proteins that the immune response to Toxoplasma is directed against several antigens. Once again, the present antigen cocktail will allow for the detection of all antibodies produced in response to these antigens.

Step F: Results of the Evaluation of Human Sera in the Recombinant Toxo Antigen (P29+P35+P66) IgM Microtiter ELISA The serum specimens from Groups 1–4 (Example 12C) were tested for the presence of Toxoplasma-specific IgM using the recombinant Toxo antigen IgM microtiter ELISA (rpToxo-P29 (P29)+rpToxo-P35S (P35)+rpToxo-P66g (P66)). The results from this evaluation are presented in Tables 9–13.

TABLE 9

Evaluation of Group 1 Negative Serum Specimens by Toxo IgM Microtiter ELISA

|  |  | Abbott IMx Toxo IgM | |
| --- | --- | --- | --- |
|  |  | Pos | Neg |
| Toxo IgM (P29 + P35 + P66) Microtiter ELISA | Pos | 0 | 7 |
|  | Neg | 0 | 193 |

Specificity: 193/200 = 96.5%

TABLE 10

Evaluation of Group 2 "Ancienne" Serum Specimens by Toxo IgM Microtiter ELISA

|  |  | Abbott IMx Toxo IgM | |
| --- | --- | --- | --- |
|  |  | Pos | Neg |
| Toxo IgM (P29 + P35 + P66) Microtiter ELISA | Pos | 0 | 8 |
|  | Neg | 0 | 92 |

Specificity: 92/100 = 92.0%

TABLE 11

Evaluation of Group 3 "Évolutive" Serum Specimens by
Toxo IgM Microtiter ELISA

|  |  | IC IgM | |
|---|---|---|---|
|  |  | Pos | Neg |
| Toxo IgM (P29 + P35 + P66) Microtiter ELISA | Pos | 69 | 0 |
|  | Neg | 30 | 0 |
| Specificity: | 69/99 = 70.0% | | |

TABLE 12

Evaluation of Group 4 "Précoce" Serum Specimens by
Toxo IgM Microtiter ELISA

|  |  | IC IgM | |
|---|---|---|---|
|  |  | Pos | Neg |
| Toxo IgM (P29 + P35 + P66) Microtiter ELISA | Pos | 53 | 1 |
|  | Neg | 2 | 10 |
| Specificity: | 53/55 = 96.7% | | |

TABLE 13

Summary of Evaluation of Groups 1–4 Serum Specimens
by Toxo IgM Microtiter ELISA

|  |  | Reference Test | |
|---|---|---|---|
|  |  | Pos | Neg |
| Toxo IgM (P29 + P35 + P66) Microtiter ELISA | Pos | 122 | 16 |
|  | Neg | 32 | 195 |
| Specificity: | 295/311 = 94.9% | | |
| Sensitivity: | 122/154 = 79.2% | | |

As can be seen from Tables 9–13, the Toxo IgM microtiter ELISA is a specific assay for the detection of Toxoplasma-specific IgM as demonstrated by the overall high relative diagnostic specificity (94.9.%) (Table 13) of the assay. However, the assay appeared to be relatively insensitive to detection of Toxoplasma-specific IgM present in serum specimens from Group 3 "évolutive" (relative diagnostic sensitivity=70%, Table 11) but sensitive to detection of Toxoplasma-specific IgM present in serum specimens from Group 4 "précoce" (relative diagnostic sensitivity=96.7%, Table 12). These data suggest that the Toxo IgM microtiter ELISA may be more sensitive to the detection of Toxoplasma-specific IgM indicative of an acute or recent infection than the IC-M immunocapture assay used as the reference assay.

Further resolution testing was performed with the Abbott IMx Toxo IgM assay and a Toxo IgG avidity assay on the 30 discordant specimens listed in Table 11 that were positive for IgM antibody using the IC-M immunocapture assay and negative for IgM antibody by the Toxo IgM microtiter ELISA. Of the 30 specimens that were false negative by the Toxo IgM microtiter assay, 11 were resolved true negative by the Abbott IMx Toxo IgM assay. Furthermore, all 11 specimens contained Toxoplasma IgG with elevated avidity, representative of a past infection. Of the remaining 19 specimens that were false negative by the Toxo IgM microtiter assay, an additional 11 specimens corresponded to Toxoplasma infections which probably occurred greater than 6 months ago, as demonstrated by the presence of Toxoplasma-specific IgG high avidity antibodies. In addition, one specimen was from a patient with reactivation of toxoplasmosis where normally Toxo IgM antibodies are absent (an IC-M and Abbott IMx Toxo IgM false positive), and one specimen was from a patient with congenital toxoplasmosis. Therefore, after resolution by the Abbott IMx Toxo IgM assay followed by consideration of the Toxo IgG avidity data and clinical history of the specimens, of the 32 specimens false negative by the microtiter IgM assay, 11 were resolved true negative, 13 specimens (from congenitally infected patients) were removed from the calculation of relative diagnostic specificity and sensitivity, and 6 specimens remained false negative. The resolved data and recalculated sensitivity and specificity for the Toxo IgM microtiter assay are shown in Tables 14 and 15.

TABLE 14

Evaluation of Group 3 "Évolutive" Serum Specimens by
Toxo IgM Microtiter ELISA
After Resolution of Discordant Specimens

|  |  | IC IgM | |
|---|---|---|---|
|  |  | Pos | Neg |
| Toxo IgM (P29 + P35 + P66) Microtiter ELISA | Pos | 69 | 0 |
|  | Neg | 6 | 11 |
| Sensitivity: | 69/75 = 92.0% | | |

TABLE 15

Summary of Evaluation of Groups 1–4 Serum Specimens
by Toxo IgM Microtiter ELISA
After Resolution of Discordant Specimens

|  |  | Reference Test | |
|---|---|---|---|
|  |  | Pos | Neg |
| Toxo IgM (P29 + P35 + P66) Microtiter ELISA | Pos | 122 | 16 |
|  | Neg | 8 | 306 |
| Specificity: | 306/322 = 95.8% | | |
| Sensitivity: | 122/130 = 93.8% | | |

As can be seen from Tables 14 and 15 after resolution of discordant specimens, the Toxo IgM microtiter ELISA configured with the antigen cocktail is both a sensitive and specific assay for the detection of Toxoplasma-specific IgM as demonstrated by the overall high relative diagnostic specificity (95.0%) and sensitivity (93.8%) (Table 15) of the assay. The Toxo recombinant antigen cocktail comprised of the Toxo antigens P29, P35, and P66 is both necessary and sufficient to replace the tachyzoite for the detection of Toxoplasma-specific IgM indicative of a recent toxoplasmosis.

Furthermore, there are several advantages of this recombinant antigen cocktail over the tachyzoite antigen for use in detection of antibodies to IgM. First, the antigens are purified and the amount of each antigen loaded into the immunoassay can be accurately determined and standardized, e.g., protein concentration. This minimizes interlot differences commonly observed in kits manufactured with different tachyzoite antigen lots. Hence, different lots of kits manufactured with different antigen cocktail lots will be very consistent from lot to lot. Secondly, mouse monoclonal antibodies to the individual recombinant Toxo antigens are used to monitor coating of the proteins to the solid phase. This further ensures that each lot produced is consistent. Third, the true clinical sensitivity of the assay using the purified antigens will be higher by virtue of the fact of the higher specific activity of the purified antigens. Fourth, an IgM assay with the antigen cocktail will preferentially detect IgM antibodies produced in response to a recent infection. This can be seen in Tables 11 and 14 where specimens with high avidity IgG antibodies (indicative of a past or chronic infection) were negative for Toxo-specific IgM using the antigen cocktail in a microtiter ELISA. Finally, kits manufactured with the antigen cocktail are more stable during storage over time, and the performance of the assay using these antigens remains consistent over the shelf life of the assay. Kits manufactured with the tachyzoite antigen are not as stable, and their performance may vary over time.

Additionally, there are many advantages of using a cocktail over using a single antigen alone. For example, an immune response to infection varies by individual. Some individuals produce antibodies to P35 and not to P30 whereas some individuals produce antibodies to P30 and not to P35. Thus, the antigen cocktail of the present invention will detect both groups of individuals.

Also, immune responses vary with time. For example, one individual may produce antibodies against P35 first and then later produce antibodies to only P30. Thus, the present cocktail will detect both types of "positive" individuals.

Furthermore, individuals may be infected with different Toxo serotypes, strains or isolates. Thus, the immune response may be such that multiple antigens are needed to detect the presence of all antibodies being produced. Again, the present cocktail allows for such detection.

Also, it is knownn from previous Western Blot experiments with tachyzoite proteins that the immune response to Toxoplasma is directed against several antigens. Once again, the present antigen cocktail will allow for the detection of all antibodies produced in response to these antigens.

What is claimed is:

1. A method for detecting the presence of IgM antibodies to *Toxoplasma gondii* (*T. gondii*) in a test sample comprising the steps of: a) contacting said test sample suspected of containing said IgM antibodies with a composition comprising a recombinant P29 antigen of *T. gondii* comprising SEQ ID NO:27, a recombinant fusion protein comprising a portion of the P35 antigen of *T. gondii*, said portion of said P35 antigen corresponding to amino acids 172–306 of SEQ ID NO:54, and a recombinant fusion protein comprising a portion of the P66 antigen of *T. gondii*, said portion of said P66 antigen corresponding to amino acids 173–575 of SEQ ID NO:55; and b) detecting the presence of said IgM antibodies.

2. A method for detecting the presence of IgM antibodies to *Toxoplasma gondii* in a test sample comprising the steps of: a) contacting said test sample suspected of containing said IgM antibodies with a composition comprising a recombinant P29 antigen of *T. gondii* comprising SEQ ID NO:27, a recombinant fusion protein comprising a portion of the P35 antigen of *T. gondii*, said portion of said P35 antigen corresponding to amino acids 172–306 of SEQ ID NO:54, and a recombinant fusion protein comprising a portion of the P66 antigen of *T. gondii*, said portion of said P66 antigen corresponding to amino acids 173–575 of SEQ ID NO:55, for a time and under conditions sufficient for the formation of IgM antibody/antigen complexes; b) adding a conjugate to the resulting IgM antibody/antigen complexes for a time and under conditions sufficient to allow said conjugate to bind to the bound antibody, wherein said conjugate comprises an anti-IgM antibody attached to a signal-generating compound capable of generating a detectable signal; and c) detecting the presence of IgM antibodies which may be present in said test sample by detecting a signal generated by said signal-generating compound.

3. The method according to claim 2 wherein said composition further comprises a fusion protein comprising a portion of the P30 antigen of *T. gondii*, said portion of said P30 antigen corresponding to amino acids 175–459 of SEQ ID NO:53.

4. A method for detecting the presence of IgG antibodies to *Toxoplasma gondii* in a test sample comprising the steps of: a) contacting said test sample suspected of containing said IgG antibodies with a composition comprising a recombinant P29 antigen of *T. gondii* comprising SEQ ID NO:27, a recombinant fusion protein comprising a portion of the P30 antigen of *T. gondii*, said portion of said P30 antigen corresponding to amino acids 175–459 of SEQ ID NO:53, and a recombinant fusion protein comprising a portion of the P35 antigen of *T. gondii*, said portion of said P35 antigen corresponding to amino acids 172–306 of SEQ ID NO:54; and b) detecting the presence of said IgG antibodies.

5. A method for detecting the presence of IgG antibodies to *Toxoplasma gondii* in a test sample comprising the steps of: a) contacting said test sample suspected of containing said IgG antibodies with a composition comprising a recombinant P29 antigen of *T. gondii* comprising SEQ ID NO:27, a recombinant fusion protein comprising a portion of the P30 antigen of *T. gondii*, said portion of said P30 antigen corresponding to amino acids 175–459 of SEQ ID NO:53, and a recombinant fusion protein comprising a portion of the P35 antigen of *T. gondii*, said portion of said P35 antigen corresponding to amino acids 172–306 of SEQ ID NO:54, for a time and under conditions sufficient for formation of IgG antibody/antigen complexes; b) adding a conjugate to resulting IgG antibody/antigen complexes for a time and under conditions sufficient to allow said conjugate to bind to bound antibody, wherein said conjugate comprises an anti-IgG antibody attached to a signal-generating compound capable of generating a detectable signal; and c) detecting IgG antibodies which may be present in said test sample by detecting a signal generated by said signal-generating compound.

6. The method according to claim 5 wherein said composition further comprises a recombinant fusion protein comprising a portion of the P66 antigen of *T. gondii*, said portion of said P66 antigen corresponding to amino acids 173–575 of SEQ ID NO:55.

7. A method for detecting the presence of IgM antibodies to *Toxoplasma gondii* in a test sample comprising the steps of: a) contacting said test sample suspected of containing said IgM antibodies with anti-antibody specific for said IgM antibodies for a time and under conditions sufficient to allow for formation of anti-antibody/IgM antibody complexes; b) adding a conjugate to resulting anti-antibody/IgM antibody complexes for a time and under conditions sufficient to allow said conjugate to bind to bound antibody, wherein said conjugate comprises a composition comprising a recombinant P29 antigen of *T. gondii* comprising SEQ ID NO:27, a recombinant fusion protein comprising a portion of the P35 antigen of *T. gondii*, said portion of said P35 antigen corresponding to amino acids 172–306 of SEQ ID NO:54, and a recombinant fusion protein comprising a portion of the P66 antigen of *T. gondii*, said portion of said P66 antigen corresponding to amino acids 173–575 of SEQ ID NO:55, each attached to a signal-generating compound capable of generating a detectable signal; and c) detecting IgM antibodies which may be present in said test sample by detecting a signal generated by said signal-generating compound.

8. The method according to claim 7 wherein said composition further comprises a recombinant fusion protein comprising a portion of the P30 antigen of *T. gondii*, said portion of said P30 antigen corresponding to amino acids 175–459 of SEQ ID NO:53.

9. A method for detecting the presence of IgG antibodies to *Toxoplasma gondii* in a test sample comprising the steps of: a) contacting said test sample suspected of containing said IgG antibodies with anti-antibody specific for said IgG antibodies for a time and under conditions sufficient to allow for formation of anti-antibody/IgG antibody complexes; b) adding a conjugate to resulting anti-antibody/IgG antibody complexes for a time and under conditions sufficient to allow said conjugate to bind to bound antibody, wherein said conjugate comprises a composition comprising a recombinant P29 antigen of *T. gondii* comprising SEQ ID NO:27, a recombinant fusion protein comprising a portion of the P30 antigen of *T. gondii*, said portion of said P30 antigen corresponding to amino acids 175–459 of SEQ ID NO:53, and a recombinant fusion protein comprising a portion of the P35 antigen of *T. gondii*, said portion of said P35 antigen corresponding to amino acids 172–306 of SEQ ID NO:54, each attached to a signal-generating compound capable of generating a detectable signal; and c) detecting IgG antibodies which may be present in said test sample by detecting a signal generated by said signal-generating compounds.

10. The method according to claim 9 wherein said composition further comprises a recombinant fusion protein comprising a portion of the P66 antigen of *T. gondii*, said portion of said P66 antigen corresponding to amino acids 173–575 of SEQ ID NO:55.

11. A method for detecting the presence of IgM antibodies to *Toxoplasma gondii* in a test sample comprising the steps of: (a) contacting said test sample suspected of containing IgM antibodies with anti-antibody specific for said IgM antibodies for a time and under conditions sufficient to allow for formation of anti-antibody IgM complexes; (b) adding an antigen to resulting anti-antibody/IgM complexes for a time and under conditions sufficient to allow said antigen to bind to bound IgM antibody, said antigen comprising a mixture of a recombinant P29 antigen of *T. gondii* comprising SEQ ID NO:27, a recombinant fusion protein comprising a portion of the P35 antigen of *T. gondii*, said portion of said P35 antigen corresponding to amino acids 172–306 of SEQ ID NO:54, and a recombinant fusion protein comprising a portion of the P66 antigen of *T. gondii*, said portion of said P66 antigen corresponding to amino acids 173–575 of SEQ ID NO:55; and (c) adding a conjugate to resulting anti-antibody/IgM/antigen complexes, said conjugate comprising a composition comprising monoclonal or polyclonal anti-IgM antibody attached to a signal-generating compound capable of generating a detectable signal; and (d) detecting IgM antibodies which may be present in said test sample by detecting a signal generated by said signal-generating compound.

12. The method according to claim 11 wherein said mixture further comprises a recombinant fusion protein comprising a portion of the P30 antigen of *T. gondii*, said portion of said P30 antigen corresponding to amino acids 175–459 of SEQ ID NO:53.

13. A method for detecting the presence of IgG antibodies to *Toxoplasma gondii* in a test sample comprising the steps of: (a) contacting said test sample suspected of containing IgG antibodies with anti-antibody specific for said IgG antibodies for a time and under conditions sufficient to allow for formation of anti-antibody IgG complexes; (b) adding an antigen to resulting anti-antibody/IgG complexes for a time and under conditions sufficient to allow said antigen to bind to bound IgG antibody, said antigen comprising a mixture a recombinant P29 antigen of *T. gondii* comprising SEQ ID NO:27, a recombinant fusion protein comprising a portion of the P30 antigen of *T. gondii*, said portion of said P30 antigen corresponding to amino acids 175–459 of SEQ ID NO:53, and a recombinant fusion protein comprising a portion of the P35 antigen of *T. gondii*, said portion of said P35 antigen corresponding to amino acids 172–306 of SEQ ID NO:54; (c) adding a conjugate to resulting anti-antibody/IgG/antigen complexes, said conjugate comprising a composition comprising monoclonal or polyclonal IgG antibody attached to a signal-generating compound capable of generating a detectable signal; and (d) detecting IgG antibodies which may be present in said test sample by-detecting a signal generated by said signal-generating compound.

14. The method according to claim 13 wherein said mixture further comprises a recombinant fusion protein comprising a portion of the P66 antigen of *T. gondii*, said portion of said P66 antigen corresponding to amino acids 173–575 of SEQ ID NO:55.

15. A method for detecting the presence of IgM and IgG antibodies to *Toxoplasma gondii* in a test sample comprising the steps of: a) contacting said test sample suspected of containing said IgM and IgG antibodies with a composition comprising a recombinant P29 antigen of *T. gondii* comprising SEQ ID NO:27, a recombinant fusion protein comprising a portion of the P30 antigen of *T. gondii*, said portion of said P30 antigen corresponding to amino acids 175–459 of SEQ ID NO:53, a recombinant fusion protein comprising a portion of the P35 antigen of *T. gondii*, said portion of said P35 antigen corresponding to amino acids 172–306 of SEQ ID NO:54, and a recombinant fusion protein comprising a portion of the P66 antigen of *T. gondii*, said portion of said P66 antigen corresponding to amino acids 173–575 of SEQ ID NO:55, for a time and under conditions sufficient for the formation of IgM antibody/antigen complexes and IgG antibody/antigen complexes; b) adding a first conjugate to resulting IgM antibody/antigen complexes and a second conjugate to resulting IgG antibody/antigen complexes for a time and under conditions sufficient to allow said first and second conjugates to bind to the bound IgM and IgG antibody, respectively, wherein said first conjugate comprises an anti-IgM antibody attached to a signal- generating compound capable of generating a detectable signal and said second conjugate comprises an anti-IgG antibody attached to a signal-generating compound capable of generating a detectable signal; and c) detecting the presence of IgM and IgG antibodies which may be present in said test sample by detecting a signal generated by said signal-generating compounds.

16. A method for detecting the presence of IgM and IgG antibodies to *Toxoplasma gondii* in a test sample comprising the steps of: a) contacting said test sample suspected of containing said IgM and IgG antibodies with anti-antibody specific for said IgM antibodies and said IgG antibodies for a time and under conditions sufficient to allow for formation of anti-antibody/IgM antibody complexes and anti-antibody/IgG antibody complexes; b) adding a conjugate to resulting anti-antibody/IgM antibody complexes and resulting anti-antibody/IgG antibody complexes for a time and under conditions sufficient to allow said conjugate to bind to bound antibody, wherein said conjugate comprises a recombinant P29 antigen of *T. gondii* comprising SEQ ID NO:27, a recombinant fusion protein comprising a portion of the P30 antigen of *T. gondii*, said portion of said P30 antigen corresponding to amino acids 175–459 of SEQ ID NO:53, a recombinant fusion protein comprising a portion of the P35 antigen of *T. gondii*, said portion of said P35 antigen corresponding to amino acids 172–306 of SEQ ID NO:54, and a recombinant fusion protein comprising a portion of the P66 antigen of *T. gondii*, said portion of said P66 antigen corresponding to amino acids 173–575 of SEQ ID NO:55, each attached to a signal-generating compound capable of generating a detectable signal; and c) detecting IgM and IgG antibodies which may be present in said test sample by detecting a signal generated by said signal-generating compounds.

17. A method for detecting the presence of IgM and IgG antibodies to *Toxoplasma gondii* in a test sample comprising the steps of: (a) contacting said test sample suspected of containing IgM and IgG antibodies with anti-antibody specific for said IgM antibodies and with anti-antibody specific for said IgG antibodies for a time and under conditions sufficient to allow for formation of anti-antibody/IgM complexes and anti-antibody/IgG complexes; (b) adding an antigen to resulting anti-antibody/IgM complexes and resulting anti-antibody/IgG complexes for a time and under conditions sufficient to allow said antigen to bind to bound IgM and IgG antibody, respectively, said antigen comprising a mixture of a recombinant P29 antigen of *T. gondii* comprising SEQ ID NO:27, a recombinant fusion protein comprising a portion of the P30 antigen of *T. gondii*, said portion of said P30 antigen corresponding to amino acids 175–459 of SEQ ID NO:53, a recombinant fusion protein comprising a portion of the P35 antigen of *T. gondii*, said portion of said P35 antigen corresponding to amino acids 172–306 of SEQ ID NO:54, and a recombinant fusion protein comprising a portion of the P66 antigen of *T. gondii*, said portion of said P66 antigen corresponding to amino acids 173–575 of SEQ ID NO:55; and (c) adding a first conjugate to resulting anti-antibody/IgM/antigen complexes and a second conjugate to resulting anti-antibody/IgG/antigen complexes, said first conjugate comprising a composition comprising an anti-IgM monoclonal or polyclonal antibody attached to a signal-generating compound capable of generating a detectable signal and said second conjugate comprising a composition comprising an anti-IgG monoclonal or polyclonal antibody attached to a signal-generating compound capable of generating a detectable signal; and (d) detecting IgM and IgG antibodies which may be present in said test sample by detecting a signal generated by said signal-generating compounds.

* * * * *